US010905405B2

(12) United States Patent
Venkatraman et al.

(10) Patent No.: US 10,905,405 B2
(45) Date of Patent: Feb. 2, 2021

(54) OCCLUSION DEVICE FOR CLOSING ANATOMICAL DEFECTS

(75) Inventors: Subramanian Venkatraman, Singapore (SG); Yin Chiang Freddy Boey, Singapore (SG); Wei Wu, Singapore (SG); Yong-dan Tang, Singapore (SG); Wei Luen James Yip, Singapore (SG); Hong Duc Duong, Singapore (SG)

(73) Assignee: Nanyang Technological University, Singapore (SG)

( * ) Notice: Subject to any disclaimer, the term of this patent is extended or adjusted under 35 U.S.C. 154(b) by 152 days.

(21) Appl. No.: 13/516,065

(22) PCT Filed: Dec. 17, 2010

(86) PCT No.: PCT/SG2010/000476
§ 371 (c)(1),
(2), (4) Date: Sep. 13, 2012

(87) PCT Pub. No.: WO2011/075088
PCT Pub. Date: Jun. 23, 2011

(65) Prior Publication Data
US 2013/0046254 A1  Feb. 21, 2013

Related U.S. Application Data

(60) Provisional application No. 61/287,544, filed on Dec. 17, 2009.

(51) Int. Cl.
*A61B 17/00* (2006.01)
*A61B 90/00* (2016.01)
(52) U.S. Cl.
CPC ............ *A61B 17/0057* (2013.01); *A61B 2017/00243* (2013.01); *A61B 2017/00592* (2013.01);
(Continued)

(58) Field of Classification Search
CPC ...... A61B 17/0057; A61B 2017/00575; A61B 2017/00592; A61B 2017/00606;
(Continued)

(56) References Cited

U.S. PATENT DOCUMENTS 5,171,259 A * 12/1992 Inoue ........................ 606/213
5,853,422 A * 12/1998 Huebsch ............ A61B 17/0057
606/213
(Continued)

FOREIGN PATENT DOCUMENTS

WO  WO 96/01599 A1  1/1996
WO  WO 97/47254 A1  12/1997
(Continued)

OTHER PUBLICATIONS

Synonym: fold; http://www.thesaurus.com/browse/fold; Mar. 10, 2016.*
(Continued)

*Primary Examiner* — Tan-Uyen T Ho
*Assistant Examiner* — Chima U Igboko
(74) *Attorney, Agent, or Firm* — Alston & Bird LLP

(57) ABSTRACT

The present invention generally relates to the field of transcatheter device closure techniques for closing an opening in a tissue and more particularly, to occlusion devices for closing anatomical defects in tissue such as defects consisting of an opening connecting a front side and a back side of a tissue. More particularly the present invention relates to occlusion devices for closing septal abnormalities such as atrial septal defects and patent foramen ovale, delivering systems for such occlusion devices, kits comprising the occlusion devices and the delivering systems and to methods of closing an anatomical defect in a tissue consisting of an opening connecting a front side and a back side of a tissue.

40 Claims, 28 Drawing Sheets

(52) U.S. Cl.
CPC ............... *A61B 2017/00597* (2013.01); *A61B 2017/00606* (2013.01); *A61B 2017/00619* (2013.01); *A61B 2017/00623* (2013.01); *A61B 2090/3966* (2016.02)

(58) Field of Classification Search
CPC ........... A61B 2017/00623; A61B 2017/00619; A61B 2017/00597; A61B 2017/00615
USPC ........................................................ 606/213
See application file for complete search history.

(56) References Cited

U.S. PATENT DOCUMENTS

| | | | |
|---|---|---|---|
| 6,174,322 B1* | 1/2001 | Schneidt | 606/213 |
| 7,431,729 B2* | 10/2008 | Chanduszko | 606/213 |
| 2002/0111647 A1* | 8/2002 | Khairkhahan et al. | 606/200 |
| 2003/0036920 A1 | 2/2003 | Smith et al. | |
| 2004/0143291 A1* | 7/2004 | Corcoran et al. | 606/213 |
| 2005/0038470 A1* | 2/2005 | van der Burg | A61B 17/0057 606/213 |
| 2005/0273135 A1* | 12/2005 | Chanduszko et al. | 606/213 |
| 2006/0265004 A1* | 11/2006 | Callaghan | A61B 17/0057 606/213 |
| 2007/0073337 A1* | 3/2007 | Abbott et al. | 606/213 |
| 2007/0198060 A1 | 8/2007 | Devellian et al. | |
| 2007/0276415 A1* | 11/2007 | Kladakis et al. | 606/151 |
| 2008/0249562 A1* | 10/2008 | Cahill | 606/215 |
| 2009/0036920 A1 | 2/2009 | Preinitz et al. | |
| 2010/0137902 A1* | 6/2010 | Lee et al. | 606/213 |

FOREIGN PATENT DOCUMENTS

| | | |
|---|---|---|
| WO | WO 03/103476 A2 | 12/2003 |
| WO | WO 2004/086951 A2 | 10/2004 |
| WO | WO 2005/034738 A2 | 4/2005 |
| WO | WO 2005/087266 A1 | 9/2005 |
| WO | WO 2005/112779 A1 | 12/2005 |
| WO | WO 2008/079639 A1 | 7/2008 |
| WO | WO 2008/085235 A2 | 7/2008 |

OTHER PUBLICATIONS

Amplatzer™ Septal Occluder; Structural Heart Therapy; St. Jude Medical; Downloaded at http://www.sjmprofessional.com/Products/Intl/structural-heart-therapy/amplatzer-sept . . . on Apr. 9, 2012.

Mullen Michael J., et al.; BioSTAR Evaluation Study (BEST); A Prospective, Multicenter, Phase I Clinical Trial to Evaluate the Feasibility, Efficacy, and Safety of the BioSTAR Bioabsorbable Septal Repair Implant for the Closure of the Atrial-Level Shunts; 2006 American Heart Association; pp. 1962-1967.

Shellock, Frank G., et al; Septal Repair Implants: evaluation of magnetic resonance imaging safety at 3 T; Magnetic Resonance Imaging 23 (2005) 1021-1025.

Gore® Helex Septal Occluder; Leave Behind the Best; Performance by Design; Aug. 2010.

Spies, Christine, et al.; Patent Foramen Ovale Closure with the Intrasept Occluder: Complete 6-56 Months Follow-Up of 247 Patients After Presumed Paradoxical Embolism; Catheterization and Cardiovascular Interventions 71:390-395 (2008).

Premere™ PFO Closure System; Structural Heart Therapy; St. Jude Medical; Downloaded at http://www.sjmprofessional.com/Products/Intl/structural-heart-therapy/premere-pfo-cl . . . on Apr. 9, 2012.

Daehnert, Ingo & Gielen, Stephen; Congenital & Structural Interventions; PFO-Closure with the Solysafe Occluder (Leipzig Experience); Herzzentrum, University of Leipzig; Leipzig, Germany; Jul. 9-11, 2009.

Marshall A C, van der Velde M E, Tworetzky W, et al.; Creation of an atrial septal defect in utero for fetuses with hypoplastic left heart syndrome and intact or highly restrictive atrial septum; Circulation 2004;110(3):253-58.

Meissner I, Khandheria B K, Heit J A, et al.; Patent foramen ovale: Innocent or guilty? Evidence from a prospective population-based study. Journal of the American College of Cardiology 2006;47(2):440-45.

Krasuski R A.; When and how to fix a 'hole in the heart': Approach to ASD and PFO. Cleveland Clinic Journal of Medicine 2007;74(2):137-47.

Drighil A, El Mosalami H, Elbadaoui N, et al.; Patent foramen ovale: A new disease? International Journal of Cardiology 2007;122(1):1-9.

Kerut E K, Norfleet W T, Plotnick G D, et al.; Patent foramen ovale: A review of associated conditions and the impact of physiological size. Journal of the American College of Cardiology 2001;38(3):613-23.

Cuadrado M L, Pareia J A.; Patent foramen ovale and migraine: where is the connection? Neurologia 2008;23(8):475-83.

Mas J L, Arquizan C, Lamy C, et al.; Recurrent cerebrovascular events associated with patent foramen ovale, atrial septal aneurysm, or both. New England Journal of Medicine 2001;345(24):1740-46.

Ozdemir A O, Tamayo A, Munoz C, et al.; Cryptogenic stroke and patent foramen ovale: Clinical clues to paradoxical embolism. Journal of the Neurological Sciences 2008;275(1-2):121-27.

Meier B.; Paradoxical embolism through the patent foramen ovale—the elderly is where the money is. Catheterization and Cardiovascular Interventions 2008;72(7):971-72.

Nendaz M R, Sarasin F P, Junod A F, et al.; Preventing stroke recurrence in patients with patent foramen ovale: Antithrombotic therapy, foramen closure, or therapeutic abstention? A decision analytic perspective. American Heart Journal 1998;135(3):532-41.

Homma S, Sacco R L, Di Tullio M R, et al.; Effect of medical treatment in stroke patients with patent foramen ovale—Patent foramen ovale in Cryptogenic Stroke Study. Circulation 2002;105(22):2625-31.

Khairy P, O'Donnell C P, Landzberg M J.; Transcatheter closure versus medical therapy of patent foramen ovale and presumed paradoxical thromboemboli—A systematic review. Annals of Internal Medicine 2003;139(9):753-60.

Homma S, DiTullio M R, Sacco R L, et al.; Surgical closure of patent foramen ovale in cryptogenic stroke patients. Stroke 1997;28(12):2376-81.

Dearani J A, Ugurlu B S, Danielson G K, et al.; Surgical patent foramen ovale closure for prevention of paradoxical embolism-related cerebrovascular ischemic events. Circulation 1999;100(19):171-75.

Van de Wyngaert F, Kefer J, Hermans C, et al.; Absence of recurrent stroke after percutaneous closure of patent foramen ovale despite residual right-to-left cardiac shunt assessed by transcranial Doppler. Archives of Cardiovascular Diseases 2008;101(7-8):435-41.

Wahl A, Meier B.; Patent foramen ovale and ventricular septal defect closure. Heart 2009;95(1):70-82.

Bijl J M, Ruygrok P N, Hornung T S, et al.; Percutaneous closure of patent foramen ovale. Internal Medicine Journal 2005;35(12):706-10.

Kedia G, Tobis J, Lee M S.; Patent foramen ovale: Clinical manifestations and treatment. Reviews in Cardiovascular Medicine 2008;9(3):168-73.

Schwerzmann M, Windecker S, Wahl A, et al.; Percutaneous closure of patent foramen ovale: impact of device design on safety and efficacy. Heart 2004;90(2):186-90.

Luermans J, Post M C, Schrader R, et al. ; Outcome after percutaneous closure of a patent foramen ovale using the Intrasept (TM) device: A multi-centre study. Catheterization and Cardiovascular Interventions 2008;71(6):822-28.

Sorensen S G, Casterella P J, Muhlestein J B, et al.; Reduced adverse event rates after transcatheter closure of patent foramen ovale when using the Amplatzer-PFO (TM) compared to the CardioSeal (TM) device. 54th Annual Scientific Session of the American-College-of-Cardiology, New Orleans, LA, 2004. p. 377A-77A.

Hein R, Bayard Y, Taaffe M, et al.; Patent foramen ovale and left atrial appendage: New devices and methods for closure. 8th Pediatric Interventional Cardiac Symposium (PICS-VIII)/2nd Conference on Emerging New Technologies in Congenital Heart Surgery (ENTICHS-II), Chicago, IL, 2005. p. 234-40.

(56) References Cited

OTHER PUBLICATIONS

Jux C, Bertram H, Wohlsein P, et al.; Interventional atrial septal defect closure using a totally bioresorbable occluder matrix—Development and preclinical evaluation of the BioSTAR device. Journal of the American College of Cardiology 2006;48(1);161-69.
Krumsdorf U, Ostermayer S, Billinger K, et al.; Incidence and clinical course of thrombus formation on atrial septal defect and patient foramen ovale closure devices in 1,000 consecutive patients. Journal of the American College of Cardiology 2004;43(2):302-09.
Carminati M, Giusti S, Hausdorf G, et al.; A European multicentric experience using the CardioSEAL((R)) and Starflex double umbrella devices to close interatrial communications holes within the oval fossa. Cardiology in the Young 2000;10(5):519-26.
Suda K, Raboisson M J, Piette E, et al.; Reversible atrioventricular block associated with closure of atrial septal defects using the amplatzer device. Journal of the American College of Cardiology 2004;43(9):1677-82.
Cohn D, Salomon A F.; Designing biodegradable multiblock PCL/PLA thermoplastic elastomers. Biomaterials 2005;26(15):2297-305.
Tasaka F, Ohya Y, Ouchi T.; Synthesis of novel comb-type polylactide and its biodegradability. Macromolecules 2001;34(16):5494-500.
Gottschalk C, Frey H.; Hyperbranched polylactide copolymers. Macromolecules 2006;39(5):1719-23.
Kim J K, Park D J, Lee M S, et al.; Synthesis and crystallization behavior of poly(L-lactide)-block-poly(epsilon-caprolactone) copolymer. Polymer 2001;42(17):7429-41.
Qian H T, Bei J Z, Wang S G.; Synthesis, characterization and degradation of ABA block copoiymer of L-lactide and epsilon-caprolactone. Polymer Degradation and Stability 2000;68(3):423-29.
Huang M H, Li S M, Vert M.; Synthesis and degradation of PLA-PCL-PLA triblock copolymer prepared by successive polymerization of epsilon-caprolactone and (DL)-lactide. Polymer 2004;45(26):8675-81.
HiljanenVainio M, Karjalainen T, Seppala J.; Biodegradable lactone copolymers .1. Characterization and mechanical behavior of epsilon-caprolactone and lactide copolymers. Journal of Applied Polymer Science 1996;59(8):1281-88.
Nakamura T, Shimizu Y, Takimoto Y, et al.; Biodegradation and tumorigenicity of implanted plates made from a copolymer of epsilon-caprolactone and L-lactide in rat. Journal of Biomedical Materials Research 1998;42(4):475-84.
Ekholm M, Hietanen J, Lindqvist C, et al.; Histological study of tissue reactions to epsilon-caprolactone-lactide copolymer in paste form. Biomaterials 1999;20(14):1257-62.
Ge H X, Hu Y, Yang S C, et al.; Preparation, characterization, and drug release behaviors of drug-loaded epsilon-caprolactone/L-lactide copolymer nanoparticles. Journal of Applied Polymer Science 2000;75(7):874-82.
Sailynoja E, Koskinen M, Salonen J, et al.; Immobilization of a biologically active coating on a hydrophobic L-lactide-epsilon-caprolactone copolymer. Journal of Materials Science—Materials in Medicine 1999;10(12):703-05.
Lu X L, Cai W, Gao Z Y, et al.; Shape memory effects of poly(L-lactide) and its copolymer with poly(epsilon-caprolactone). Polymer Bulletin 2007;58(2):381-91.
Ray J A, Doddi N, Regula D, et al.; Polydioxanone (PDS), A Novel Mono-Filament Synthetic Absorbable Suture. Surgery Gynecology & Obstetrics 1981;153(4):497-507.
Xie J, Ihara M, Jung Y M, et al.; Mechano-active scaffold design based on microporous poly(L-lactide-co-epsilon-caprolactone) for articular cartilage tissue engineering: Dependence of porosity on compression force-applied mechanical behaviors. Tissue Engineering 2006;12(3):449-58.
Tan L P, Venkatraman S S, Sung P F, et al.; Effect of plasticization on heparin release from biodegradable matrices. International Journal of Pharmaceutics 2004;283(1-2):89-96.
Xie Y C, Yang Q F.; Surface modification of poly(vinyl chloride) for antithrombogenicity study. Journal of Applied Polymer Science 2002;85(5):1013-18.
Yang M C, Lin W C.; Surface modification and blood compatibility of polyacrylonitrile membrane with immobilized chitosan-heparin conjugate. Journal of Polymer Research-Taiwan 2002;9(3):201-06.
Zhu A P, Zhang M, Wu J, et al.; Covalent immobilization of chitosan/heparin complex with a photosensitive hetero-bifunctional crosslinking reagent on PLA surface. Biomaterials 2002;23(23):4657-65.
Kreitz M R, Domm J A, Mathiowitz E.; Controlled delivery of therapeutics from microporous membranes. II. In vitro degradation and release of heparin-loaded poly(D,L-lactide-co-glycolide). Biomaterials 1997;18(24):1645-51.
International Preliminary Report on Patentability and Written Opinion for Application No. PCT/SG2010/000476 dated Jun. 19, 2012.
International Search Report for Application No. PCT/SG2010/000476 dated Apr. 5, 2011.

\* cited by examiner

OCCLUSION DEVICE FOR CLOSING ANATOMICAL DEFECTS

RELATED APPLICATION

This application claims the benefit of priority of U.S. provisional application No. 61/287,544, filed Dec. 17, 2009, the contents of it being hereby incorporated by reference in its entirety for all purposes.

FIELD OF THE INVENTION

The present invention generally relates to the field of transcatheter device closure techniques for closing an opening in a tissue and more particularly, to occlusion devices for closing anatomical defects in tissue.

BACKGROUND OF THE INVENTION

Defects in tissue are often combined with an opening in a tissue such as in the blood vessel wall and organ tissues, like the septum in the heart of mammals, for example. There are two major types of septal abnormalities: atrial septal defect (ASD) and patent foramen ovale (PFO) as shown in FIG. 1. FIG. 1a shows normal septa between the right atrium (1) and the left atrium (2).

During the fetal development, the septum primum (3) starts to grow downward from the roof to divide the atria into two chambers, leaving a hole in the center called ostium secundum (4). A second septum, septum secundum (5), starts to develop on the right atrial side of the septum primum (3) and normally completely covers the ostium secundum (4) and, thereby resulting in a closed foramen ovale (6). However in some cases, incomplete coverage results in a hole (an opening) permitting blood flow in either direction (left-to-right or right-to-left), also known as an atrial septal defect. This atrial septal defect is also called secundum ASD (7). An example of such an atrial septal defect is shown in FIG. 1b. Even after normal formation of the septum secundum (5), an opening foramen ovale—remains between the septa in the fetus, functioning as a one-way (right-to-left) valve. This opening allows blood to follow from right atrium (1) to left atrium (2), bypassing the lungs in utero. At birth, changes in atrial pressures leads to apposition of the septa. Complete sealing of the opening happens within hours of birth. However, a patent foramen ovale, also called PFO (8), remains for about 25% of the total population. This situation is shown in FIG. 1c. ASD accounts for 25-30% of congenital heart defects that are diagnosed in adult hood, among which the majority are Secundum ASD (about 75%, located in the region of the fossa ovalis). The associated symptoms are most often exertional dyspnoea or fatigue and subsequent morbidity includes right ventricular dysfunction and failure, atrial tachyarrhythmias, or stroke. Clinical significance of PFO is still much debated; however, even a small, untreated patent foramen ovale can cause heart-related difficulties such as labored breathing or recurrent respiratory infections. Other medical conditions, such as migraine headaches, have also been associated with a PFO. PFO is also considered a possible risk factor for stroke and systemic embolism because of the potential formation of blood clots. These clots may form in veins and subsequently pass into circulation through the PFO, without being filtered in the lungs.

In general, treatment options include anticoagulant medication, surgical closure and transcatheter device closure. The anticoagulant therapy normally comprises the administration of aspirin, clopidogrel (Plavix), aspirin and clopidogrel together, and warfarin (Coumadin). Medication does not improve morbidity to a comfortable level and only reduces the risk of mortality. Surgical closure can be done safely and achieve extremely low mortality rate. But it does require open-heart surgery and an extracorporeal circulation system. Transcatheter closure is safe and effective for Secundum ASD and PFO. The entry is similar to a percutaneous cardiovascular intervention (PCI) procedure and is mostly done under the guidance of fluoroscope and transesophageal echocardiography (TEE). The minimum invasive surgery allows better patient compliance and faster recovery too.

The main current occluders for ASD and/or PFO closure are generally made of a metal frame (specifically made of Nitinol or Phynox) with synthetic fabrics (specifically made of polyester, Dacron or PTFE) or collagen matrix patches used as inserts. The metal frame usually has the form of an umbrella on each side of the opening combined by a metallic waist. The occluders are usually folded and inserted into a trans-luminal sheath, which is placed at the ASD/PFO location. Then the devices are deployed to seal the ASD/PFO under the instruction of fluoroscopy and/or echocardiography.

After the ASD/PFO defect is closed by an occluder, a layer of ingrown tissue will usually cover the device and will thus close the defect. Although elegant and smart device designs have been achieved owing to metal flexibility and excellent modulus, permanent presence of metal in the mammalian body is not desired due to allergy and long-term toxicity risk. Metal-rich devices are also related to problems like friction lesions, perforations, erosion and thromboembolism. Furthermore, these devices made of metal and synthetic fabrics may obstruct the trans-septal access for the left atrium, which is of significant importance for the future treatment of left-sided heart disease including percutaneous heart valve repair or replacement, arrhythmia studies, and therapies (e.g., pulmonary vein exclusion and left atrial appendage closure).

Considering the above comments, it is therefore among others an object of the present application to overcome at least some of the above-mentioned problems of existing occluders and to provide an alternative occlusion device for closing an opening in a tissue.

SUMMARY OF THE INVENTION

According to a first aspect of the present application, an occlusion device for closing an anatomical defect in tissue comprising an opening connecting a front side and a back side of a tissue is provided, wherein the occlusion device is adapted to be included into a sheath of a catheter. The occlusion device comprises:
(i) a scaffold comprising:
   a head tube positioned at an anterior end of the scaffold,
   a tail tube positioned at a posterior end of the scaffold; wherein the head tube and the tail tube are movable along the direction towards and away from each other, and
   an engaging means connected to the head tube and being adapted to be engagable at the tail tube, and
(ii) a foldable section comprising:
   a foldable head portion which is connected at one end to the head tube and being adapted to be disposed together with the head tube at the front side of the defect,
   a foldable tail portion which is connected to one end of the tail tube and being adapted to be disposed together with the tail tube at the back side of the defect, and a waist portion adapted to extend through the opening of the defect and being arranged between the foldable head portion and the foldable tail portion, wherein each of the foldable head portion and the foldable tail portion comprises two or more arms extending between the head tube and the waist portion and between the tail tube and the waist portion, respectively, wherein each arm comprises a folding segment.

According to a second aspect, a delivering system for an occlusion device of the first aspect is provided, wherein the occlusion device is adapted to be included into a sheath of a catheter. The delivering system comprises:

at least one first delivering means adapted to push the occlusion device through a sheath and to guide the head portion of the foldable section in a position at the front side of a tissue defect, and at least one second delivering means adapted to move the tail tube into the direction of the head tube to allow the tail tube to be moved against the back side of the tissue.

According to a third aspect of the application, a kit comprising an occlusion device of the first aspect and a delivering system of the second aspect is provided.

According to a fourth aspect of the application, a method of closing an anatomical defect in a tissue consisting of an opening connecting a front side and a back side of a tissue is provided. The method comprises the steps of:

providing the sheath into which the occlusion device according to the first aspect and the delivering system according to the second aspect have been inserted, pushing the occlusion device through the sheath to the site of the anatomical defect by using the first delivering means of the delivering system, pushing the head tube of the scaffold and the foldable head portion of the foldable section of the occlusion device out of the sheath through the defect to the front side of the tissue, folding the foldable head portion by pulling the delivering wire of the occlusion device to close the defect from the front side, withdrawing the sheath to release the waist portion and the tail portion of the foldable section of the occlusion device in the opening and at the back side of the tissue, respectively, and pushing the tail tube of the occlusion device against the back side of the tissue by means of the second delivering means of the delivering system to fold the foldable tail portion of the foldable section of the occlusion device and locking the occlusion device at the anatomical defect from the back side of the tissue.

Alternative embodiments as well as other aspects and features of the present invention are described in the dependent claims and will become apparent from the following description of specific embodiments and non-limiting examples of the present invention.

BRIEF DESCRIPTION OF THE DRAWINGS

The invention will be better understood with reference to the detailed description when considered it in conjunction with the non-limiting examples and the accompanying drawings.

FIG. 7a shows structure details of the occlusion device in the unfolded state but being provided with parts of a delivering system of the present invention. FIG. 7b shows a front view of the occlusion device of FIG. 7a in working structure and FIG. 7c shows a back view of the occlusion device in working structure. The disc in FIGS. 7b and c is an atrial septal defect/patent foramen ovale (ASD/PFO) model.

FIG. 9a shows the 100% strain of stress relaxation curve and FIG. 9b shows the 200% strain of stress-relaxation curve.

FIGS. 29a and b show the debubbling of an embodiment of the occlusion device described herein, wherein FIG. 29a shows a photo during the flushing with syringe and FIG. 29b shows the debubbled occlusion device and delivering system.

DETAILED DESCRIPTION OF THE INVENTION

Figure 1:
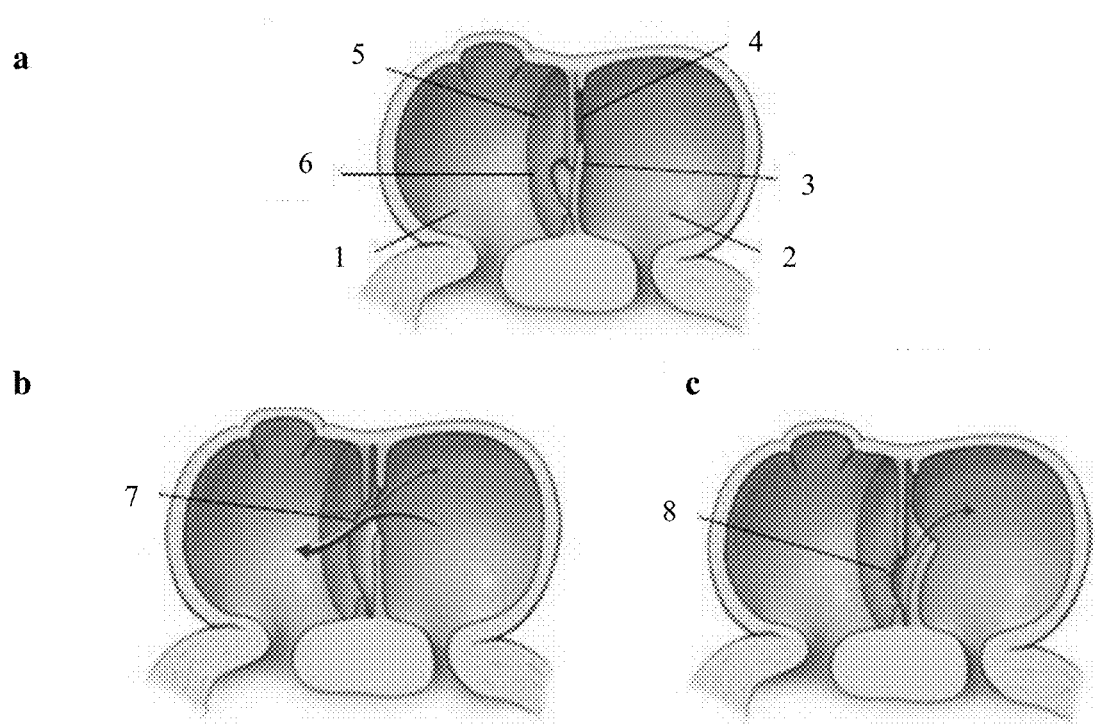
FIGS. 1a-c show (a) normal septa, (b) septa with an atrial septal defect (ASD) and (c) septa with patent foramen ovale (PFO).

According to a first aspect, the invention refers to an occlusion device for closing an anatomical defect in tissue which can be adapted to be included into a sheath of a catheter. In the context of the present invention, an occlusion device is a catheter-deliverable device that closes a hole in the wall of a tissue like a hole in the septa of a heart. Once in place the occlusion device is released on both sides of the defect from the sheath and folded in such a manner that pressure from both sides of the opening keeps it in place, thereby closing the opening from both sides. The occlusion device thus can function as a permanent implant that stays in the body after the procedure. The occlusion device can, however, also be used in in vitro methods for closing tissue defects outside the body, for example.

The occlusion device of the first aspect comprises (i) a scaffold and (ii) a foldable section.

In the following an embodiment of the scaffold is described. According to this embodiment, the scaffold can comprise a head tube positioned at an anterior end of the scaffold, a tail tube positioned at a posterior end thereof, wherein the head tube and the tail tube are movable along the direction towards and away from each other. The scaffold can further comprise an engaging means connected to the head tube and being adapted to be engageable at the tail tube.

The scaffold that means one or more of the head tube, the tail tube, and the engaging means can be made of a polymeric material. The polymeric material can be a non-biodegradable or biodegradable polymer or copolymer.

In the context of the present invention, the term "non-biodegradable polymer" refers to a polymer material comprising one or more polymer components that cannot be removed from a localized area by metabolic processes, i.e. by biodegradation. Various examples of non-biodegradable polymers can be selected from the group consisting of polyurethane, poly(ether urethanes), poly(ester urethanes), polyvinylchloride, polyalkylenes, polyethylene terephtalate polyvinyl acetate, poly ethylene-co-vinyl acetate and nylon.

In the context of the present invention the term "biodegradable polymer" refers to a polymer material comprising one or more polymer components that can be completely removed from a localized area by physiological metabolic processes such as resorption. A "biodegradable" compound can, when taken up by a cell, be broken down into components by cellular machinery, i.e. by biodegradation, such as lysosomes or by hydrolysis that the cells can either reuse or dispose of without significant toxic effect on the cells. Examples of biodegradation processes include enzymatic and non-enzymatic hydrolysis, oxidation and reduction. Suitable conditions for non-enzymatic hydrolysis, for example, include exposure of biodegradable material to water at a temperature and a pH of a lysosome (i.e. the intracellular organelle). The degradation fragments typically induce no or little organ or cell overload or pathological processes caused by such overload or other adverse effects in vivo.

Various examples of biodegradable polymer materials are known in the art, any of which are generally suitable for use in the occlusion device of the present invention. Examples of polymers that are considered to be biodegradable include aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, polycarbonates naturally-occurring biodegradable polymers such as chitosan, collagen, starch, and blends thereof. Examples of polyortho esters include a polylactide, a polyglycolide, a polycaprolactone, a polylactic acid, a biodegradable polyamide, a biodegradable aliphatic polyester, and/or copolymers thereof or with other biodegradable polymers such as those mentioned above. Illustrative examples of biodegradable polymers include, but are not limited to a polylactide such as poly(L-lactide) (PLLA), a polycaprolactone (PCL), a copolymer of polycaprolactone (PCL) and polylactic acid (PLA), or a copolymer of poly(lactide) and poly(glycolide) (PLGA). More specific examples of copolymers which can be used in the present invention include copolymers of polycaprolactone (PCL) and polylactic acid (PLA) having an glycolide content of about 5-60%, 5-55%, 5-50%, 10-50%, 15-50%, or 20-50%, or approximately 20%, 25%, 30%, 35%, or 50%, or a copolymer of poly(lactide) and poly(glycolide) (PLGA) having an glycolide content of about 5-50%, 10-50%, 15-50%, or 20-50%, or approximately 20%, 25%, 30%, 35%, or 50%, based on the copolymer composition.

The head tube can have an outer diameter of more than 1.0, 1.1, 1.2, 1.3, 1.4, 1.5, 1.6, 1.7, 1.8 mm and less than 3.0, 2.5, 2.4, 2.3, 2.2, 2.1, 2.0 mm, for example about 1.9 mm. The wall thickness of the head tube can be more than 0.1, 0.2, 0.3, 0.4, 0.5, 0.6 mm and less than 1.3, 1.2, 1.1, 1.0, 0.9, 0.8 mm, and for example about 0.7 mm. The length of the head tube can be between about 2-6, 2.5-5.5, 2.5-5, 2.7-4.5, 2.7-4.2, 3-4 mm.

The tail tube can have an outer diameter of more than 1.5, 1.6, 1.7, 1.8, 1.9, 2.0, 2.1, 2.2, 2.3, 2.4, 2.5, 2.6 mm and less than 4.0, 3.5, 3.4, 3.3, 3.2, 3.1, 3.0, 2.9, 2.8 mm, for example about 2.7 mm. The wall thickness of the tail tube can be more than 0.1, 0.2, 0.3, 0.4 mm and less than 1.2, 1.1, 1.0, 0.9, 0.8, 0.7, 0.6 mm, and for example about 0.5 mm. The length of the tail tube can be between about 2-6, 2.5-5.5, 2.5-5, 2.7-4.5, 2.7-4.2, 3-4 mm.

The head tube can be a cylindrical hollow tube and, in one embodiment, can have a threaded interior. The threaded interior can be adjusted such that a rod which is also threaded at the exterior surface of its tip can be attached to the head tube by means of a clockwise turn and can be detached off the head tube by anti-clockwise turn (cf. reference numeral 310 in FIG. 2). Alternatively, the threaded interior of the head tube can be adjusted such that rod can be attached to the head tube by an anti-clockwise turn and can be detached off the head tube by a clockwise turn.

In another embodiment, the head tube can be a cylindrical hollow tube and can have a tapered interior such that a rod can be attached by a pushing force and can be detached off the head tube by a pulling force of the rod. Thus, a rod can be attached to the head tube by means of a slip-fit mechanism, for example.

The tail tube can be a hollow tube similar to the head tube above. In an embodiment of the occlusion device described herein, the tail tube can have a threaded exterior surface (cf. reference numeral 190-1 in FIGS. 2 and 4). In this embodiment, a deployment tube can be attached to the tail tube by means of a clockwise turn and can be detached off the tail tube by means of an anti-clockwise turn. Alternatively, the threaded exterior of the tail tube can be adjusted such that the deployment tube can be attached to the tail tube by an anti-clockwise turn and can be detached off the tail tube by a clockwise turn.

Figure 6:
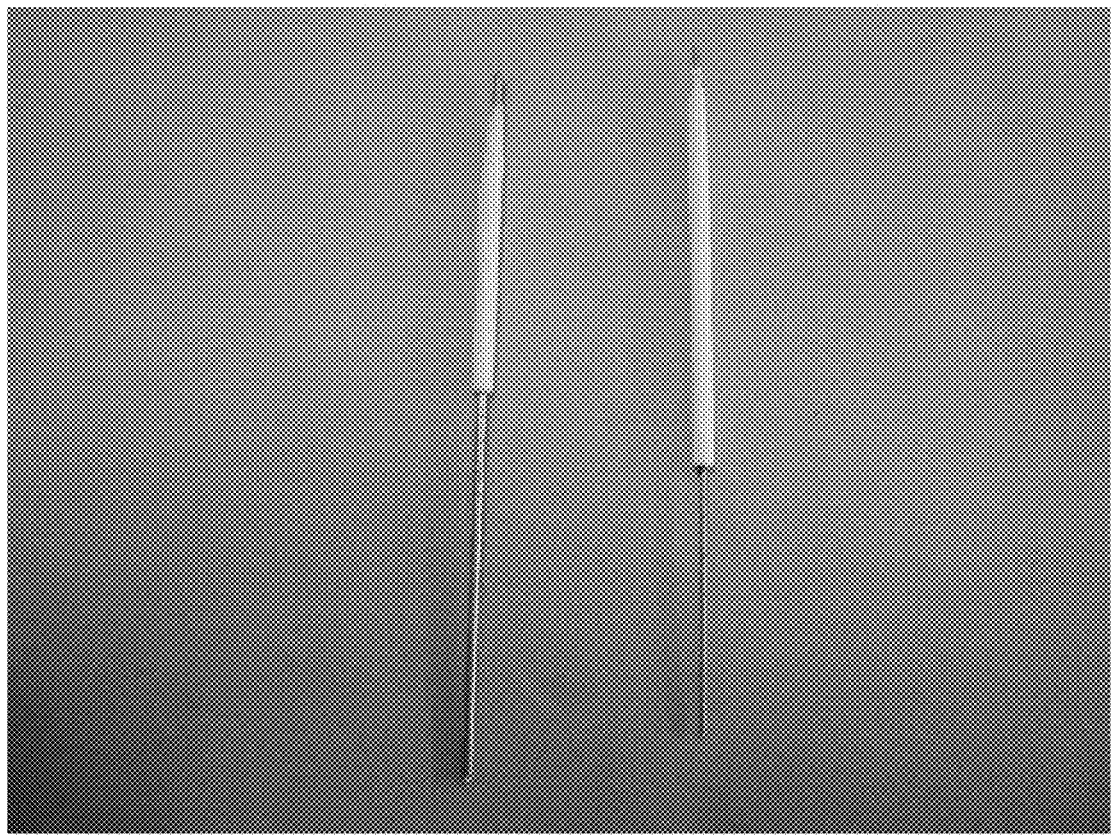
FIG. 6 shows tubes for the head tube or the tail tube of an embodiment of the occlusion device described herein, wherein the tubes have been produced by a dipping procedure.

The head and tail tubes can for example be prepared by dip casting of the polymeric material with metal wires, e.g. Nitinol wires, as the mandrel as shown in FIG. 6.

The engaging means is adapted to be engagable at the tail tube. The term "engageable" means in the context of the application that the engaging means can extend from the head tube to the tail tube and can be locked with its free end at the tail tube. In addition, the engaging means can be a rigid or flexible member such as a wire, a rod, a cantilever or the like as long as the engaging means can be engaged at the tail tube directly or by means of a lock behind the tail tube. The engaging means can be hollow or solid, can have a rectangular, circular, or elliptical cross section, and can have a smooth, notched or corrugated outer surface. The engaging means can be connected to the head tube of the scaffold, for example, by laminating, gluing, sewing or welding.

The engaging means can be made of the same polymeric materials as the head tube or the tail tube as described before. In an embodiment, the engaging means can be integrally formed with the head tube and can be of the same material as the head tube.

Figure 2:
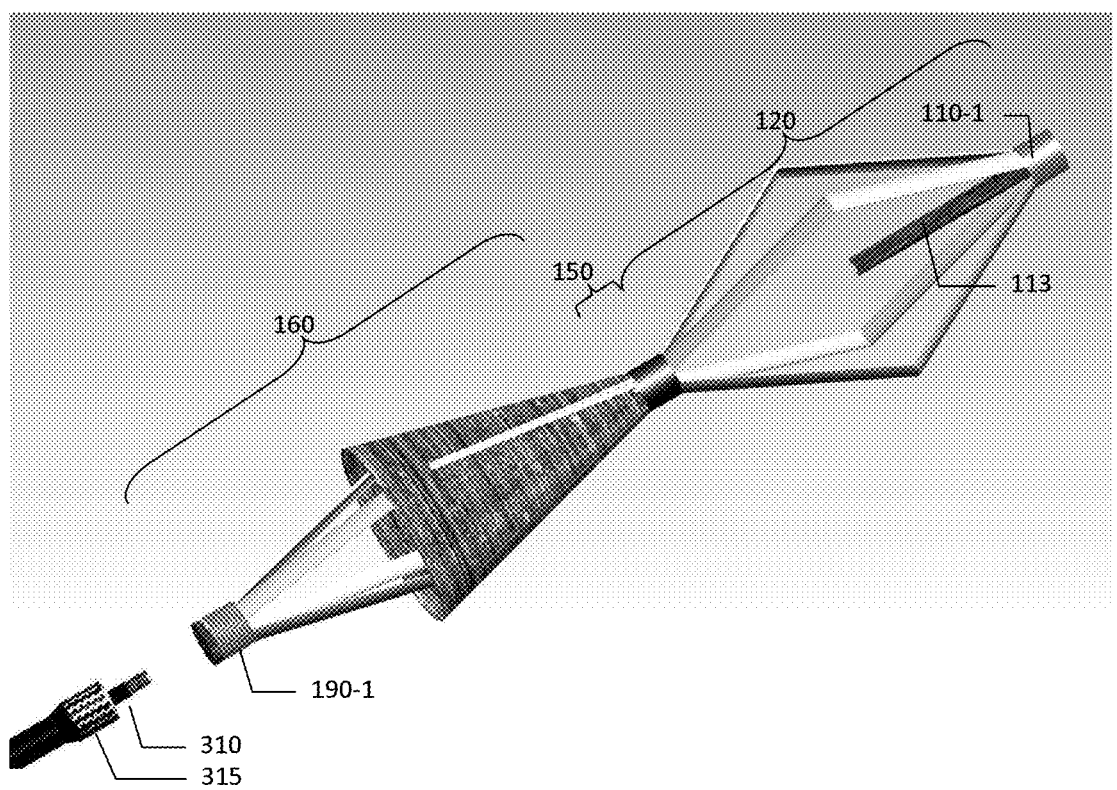
FIG. 2 shows an exploded perspective view of an embodiment of an occlusion device and components of a delivering system described herein.
Figure 3:
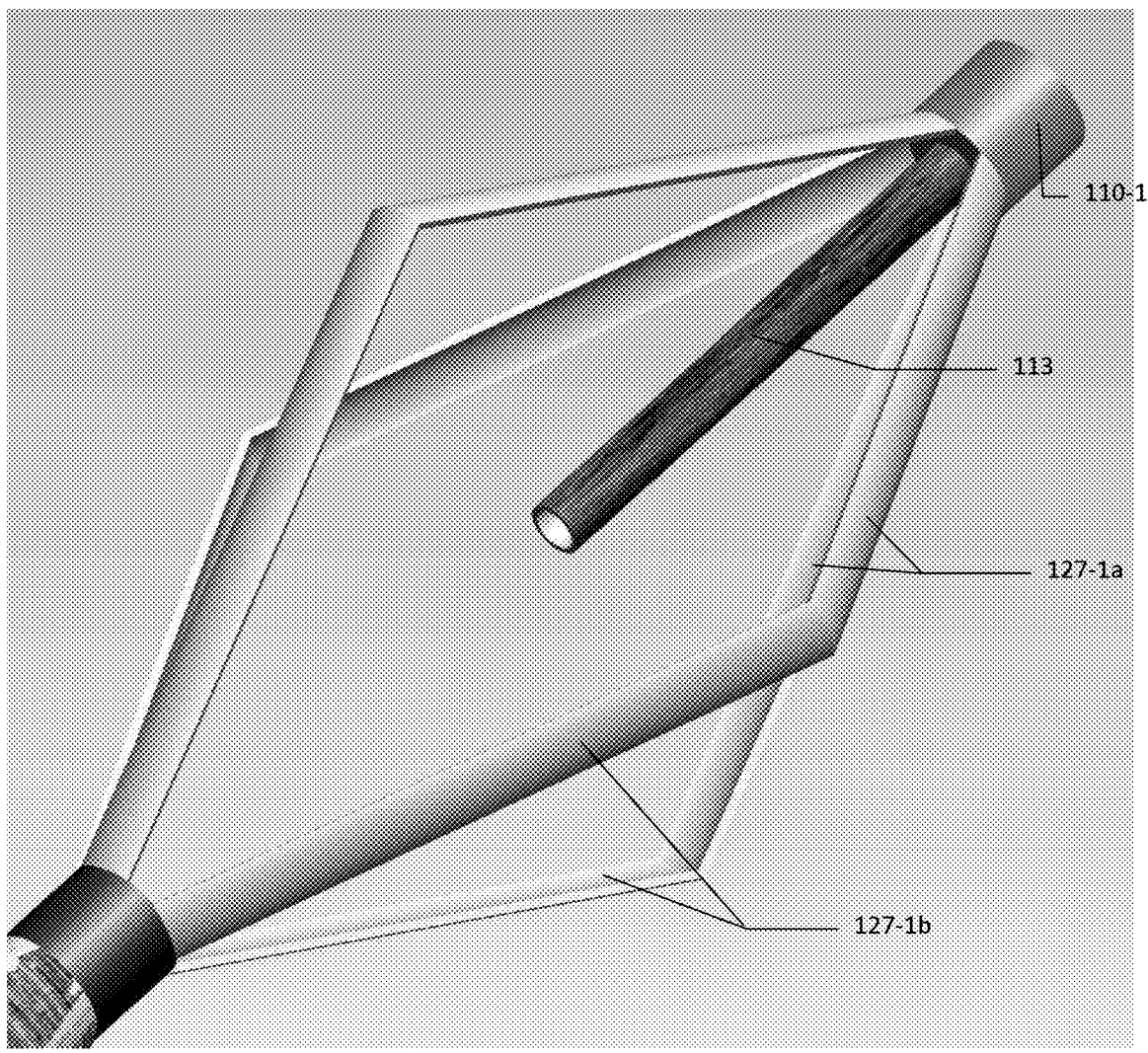
FIG. 3 shows an enlarged perspective view of the anterior portion of the occlusion device shown in FIG. 2.

The engaging means can in an exemplary embodiment have the form of a hollow cylindrical rod and can have an inner diameter of about 0.3-1.0 mm, 0.4-0.9 mm, 0.5-0.8 mm, 0.6-0.7 mm, especially about 0.65 mm. The outer diameter of the engaging means can be more than 0.4, 0.5, 0.6, 0.7, 0.8, 0.9, 1.0, 1.1, 1.2, 1.3, 1.4, 1.5 mm and less than 2.0, 2.1, 2.2, 2.3, 2.4, 2.5, 2.6, 2.7, 2.8, 2.9, 3.0 mm, and for example about 1.5-2.0, 1.6-1.9, 1.7-1.8 mm. The length of the engaging means as described herein can extend over a length in the direction of the tail tube which is about three quarters, two thirds, or half the length between the waist portion and the head tube in the unfolded form of the occlusion device as shown in FIG. 2 or 3.

In case the engaging means is a wire, it can be simultaneously function as a delivering wire to move the head tube into the direction of the waist portion by pushing or pulling at the delivering wire directly or via a further external delivering member as described in the second and fourth aspects of the present application. If the delivering wire is sewed to the head tube, the one end or both ends of the wire can be sewed on the head tube, for example by making a knot into the wire. In case both ends of the delivering wire are sewed to the head tube, then the delivering wire will have the form of a loop, which can extend in the direction of the tail tube. The sewing material can be any polymeric suture wire selected from non-biodegradable or biodegradable polymers wherein examples of non-biodegradable polymers for the use in occlusion devices are nylon or polyethylene terephtalate and examples of biodegradable polymers for the use in occlusion devices are PGA, PLA or polydioxanone. Of course other polymeric suture materials usually used in this field and as described for the delivering wire in the materials section can also be used as the suture material.

The delivering wire can be made of any surgical suture such as non-absorbable or absorbable sutures. Absorbable sutures are made of materials, which are broken down in tissue after a given period of time, which depending on the material can be from ten days to eight weeks. They are generally used therefore in many of the internal tissues of the body. Absorbable sutures were originally made of the intestines of sheep, the so called catgut. The majority of absorbable sutures are made of synthetic polymer fibers, which may be braided or monofilament. Exemplary polymeric materials of such synthetic absorbable sutures a various blends of polyglycolic acid, polylactic acid or caprolactone. Non-absorbable sutures are generally made of materials which are not metabolized by the body, and are used therefore either on skin wound closure, where the sutures can be removed after a few weeks, or in some inner tissues in which absorbable sutures are not adequate. This is the case, for example, in the heart and in blood vessels, whose rhythmic movement requires a suture which stays longer than three weeks, to give the wound enough time to close. Other organs, like the bladder, contain fluids which make absorbable sutures disappear in only a few days, too early for the wound to heal. There are several materials used for non-absorbable sutures. The most common is a natural fiber, silk, which undergoes a special manufacturing process to make it adequate for its use in surgery. Other non-absorbable sutures are made of artificial fibers, like polypropylene; polyester or nylon; these may or may not have coatings to enhance their performance characteristics.

In an embodiment of the occlusion device, the delivering wire can be made of synthetic absorbable surgical sutures, for example PDS II (Ethicon, manufactured from J&J) made from poly(p-dioxanone). The polymer has been found to be non-antigenic, con-pyrogenic and elicits only a slight tissue reaction during absorption. However, any other non-biodegradable or bio-degradable wire material as described above can be used.

The diameter of the delivery wire can be between 0.2 and 0.4, between 0.21 and 0.35, between 0.21 and 0.30 mm, for example about 0.29 (PDS II 3/0).

In an alternative embodiment, more than one delivering wire can be used, for example one, two, three, four, or more separate wires. In a particular embodiment the delivering wire comprises one wire which is in loop form. That means that two ends of a delivering wire can extend from the head tube and can form a loop which can end in a position between the head tube and the tail tube or at a position behind the tail tube, when looking from the head tube to the tail tube.

In a further embodiment, the delivering wire can be fixed with both free ends at the tail tube and can extend in the direction of the head tube to form a loop. In this embodiment, the loop crosses at least two eye-shaped members fixed to the head tube so that the loop-formed delivering wire can move the head tube in the direction of the tail tube by means of moving the end of the loop in the direction away from the head tube and in the direction to the tail tube. Thus, the part of the delivering wire between the tail tube and the head tube will be shorter with the time of moving the end of the loop in the direction away from the head tube.

In another embodiment, the engaging means can be engageable at the tail tube directly or by means of a lock. The lock can, for example, be a flexible end cap having two crossed slots in its center through which the engraining means extends in the folded state of the occlusion device described herein. The lock can be integrally provided at the posterior end of the tail tube or can alternatively be a separate member functioning to closely lock the engaging means to maintain the folded stat of the occlusion device described herein. The lock can, in a further embodiment, be positioned behind the tail tube and can be in the form of a tube which is movable along the direction towards and away from the tail tube. The lock tube can be provided behind the tail tube, i.e. at the posterior end of the tail tube, which is not connected to the foldable section. The lock tube can have a form of a tube and its tubular opening can be arranged perpendicular to the tubular opening of the tail tube. In an embodiment, the engaging means extends through a hole provided in the middle of the wall of the lock tube and extending perpendicular to the tubular opening of the lock tube. The lock tube can have a length of about 1-5, 1-4.5, 1-4, 1.5-4, 1.5-3.5, 2-3 mm and an outer diameter between 1-3, 1.5-2.5, 1.7-2.3, 1.8-2.2, 1.9-2.1 mm and more particularly of about 2 mm.

In the following the foldable section is described in detail. The foldable section according to an embodiment of the first aspect can comprise at least three portions. The first portion can be a foldable head portion, which is connected at one end to the head tube and being adapted to be disposed together with the head tube at the front side of the defect. The second portion can be a foldable tail portion, which is connected to one end of the tail tube and being adapted to be disposed together with the tail tube at the back side of the defect. The third portion can be a waist portion extending through the opening of the defect and being arranged between the foldable head, portion and the foldable tail portion. The waist portion, which is arranged between the head portion and the tail portion of the film(s) can be connected at one end to the end of the head portion not connected to the head tube and at the other end to the end of the tail portion not connected to the tail tube.

The foldable head portion can include, but is not restricted to, two or more arms; for example to two to eight arms, extending between the head tube and the waist portion wherein each arm comprises a folding segment. In one embodiment, two arms are provided. In another embodiment, three or more arms, such as for example, three to eight arms, that means three, four, five, six, seven, or eight arms, can be provided in the foldable head portion. Folding segment means in the context of the foldable portion that the arm is flexible enough at the folding segment to fold the part of the arm between the folding segment and the head tube in the direction of the part between the folding segment and the waist portion of the arm. This can, for example, be done by means of a thinner part of the arm or by using a more flexible material in that part of the arm to achieve a sufficient flexibility. In a further embodiment, the folding segment can be a flexible joint or a hinge made of the same or a different material as the material of the arm. In another embodiment, the arm can have two, three, four, or more different segments, each adjusted to fold a segment of each arm at least partly to allow the part of the arm next to the head portion being folded to the part of the arm next to the waist portion.

Any arm of the foldable head section can comprise the same number or different numbers of folding segments. In addition, the folding segments of each arm can have the same or a different functioning mechanism as long as the foldable head portion can be fixed at the front side of the defect.

The foldable tail portion can include, but is not restricted to, two or more arms, for example to two to eight arms, extending between the tail tube and the waist portion wherein each arm comprises a folding segment. In one embodiment, two arms are provided. In another embodiment, three or more arms, such as for example, three to eight arms, that means three, four, five, six, seven, or eight arms, can be provided in the foldable tail portion. The arms and the folding segments in the foldable tail portion can have the same structure and can be made of the same materials as the arms and folding segments of the foldable head portion.

In an embodiment of the occlusion device described herein, the arms comprised in the foldable head portion can have a sheet-like form. In this embodiment, two sheet-like arms can be arranged on each other in a manner that the engaging means is positioned between the two arms. In other words, one or more films formed in a sheet-like form are arranged between the head tube and the waist portion as shown, e.g., in the occlusion device shown in FIGS. 7a-c. The same configuration of the two arms can be present in the foldable tail portion of the occlusion device described herein.

In other words, the foldable section in this embodiment includes, but is not limited to, one or more films formed in a sheet-like form between the head tube and the tail tube and being connected to the head tube and the tail tube via a first end and a second end of the foldable section. The foldable section of the occlusion device can comprise one or more films formed in a sheet-like form between the head tube and the tail tube when the foldable section is unfolded. When the foldable section is folded, for example if the occlusion device is placed near or in the tissue of a patient for closing a defect, the films can be folded at specific parts thereof, namely the foldable head portion and the foldable tail portion, wherein the waist portion can maintain its form.

Figure 5:
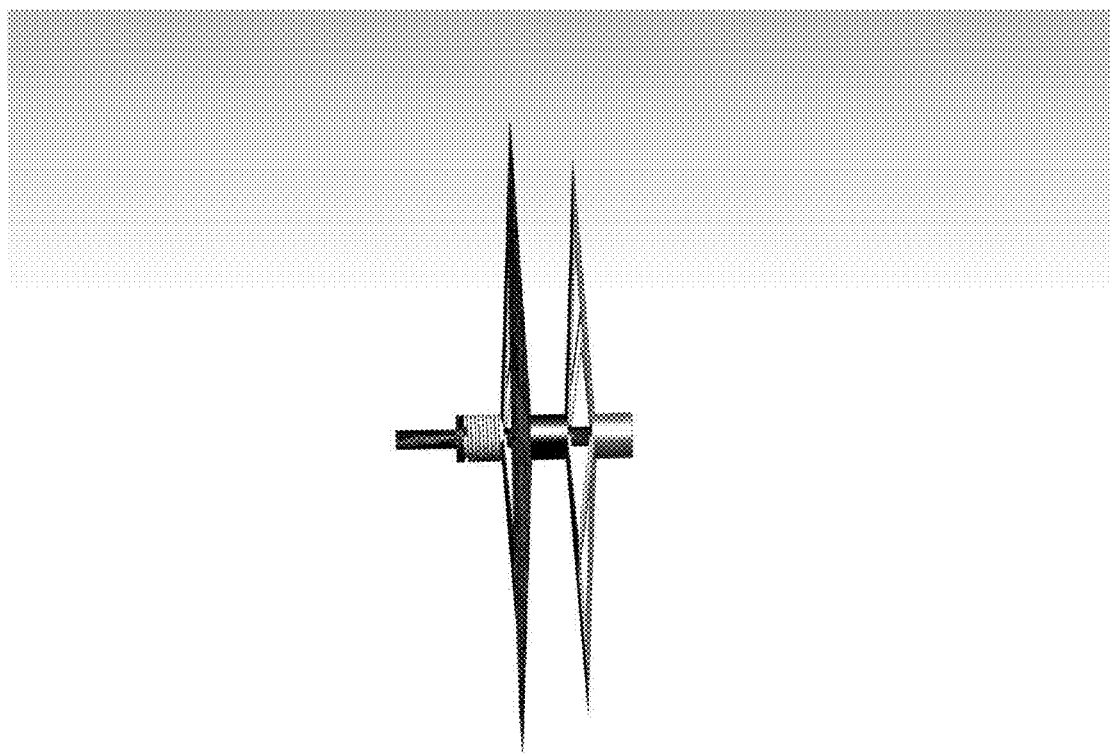
FIG. 5 shows the occlusion device shown in FIG. 2 in its folded state.
Figure 7:
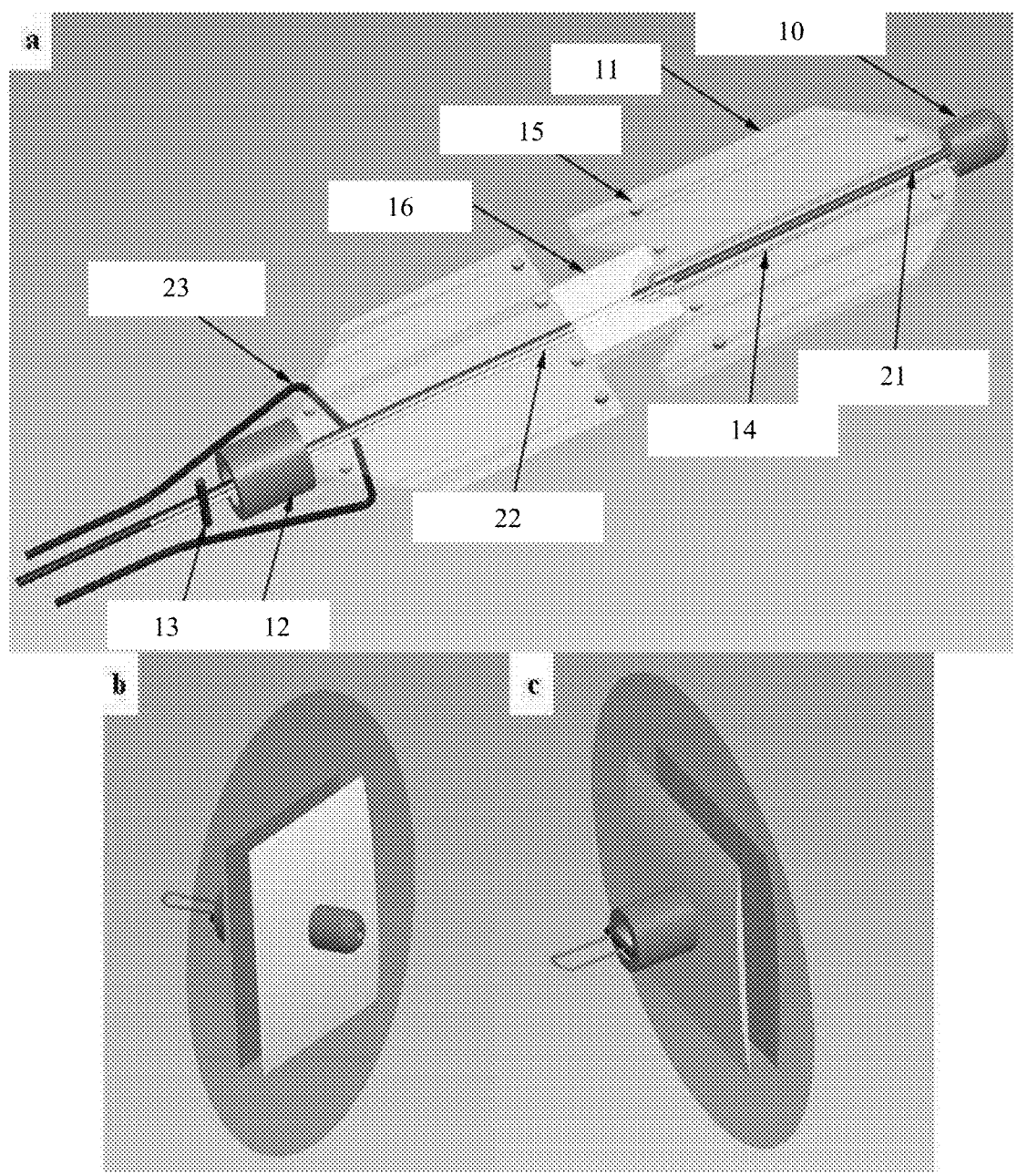
FIGS. 7a-c show schematic views of another embodiment of an occlusion device described herein.

In the context of the present invention, the "foldable section is folded" means that the foldable section or a part of it which is referred to be folded is present in a form as shown for example in FIG. 5 or in FIGS. 7b and c. In the following, this state is also called "working structure" of the occlusion device. The "foldable section is unfolded" means that the foldable section or part of it is in the form as shown in FIG. 2 or in FIG. 7a. In these Figures none of the parts of the foldable section is folded.

In another embodiment, the foldable head portion comprises three or more, e.g. three to eight, arms as described beforehand, wherein they are arranged in such a manner that the engaging means is positioned in the center of the three or more arms. That means that in the unfolded state of the foldable head portion, the arms can be arranged as shown in the embodiment having four arms within the foldable head portion which is shown in FIGS. 2 and 3. The same configuration of the three, four, five, six, seven, eight or more arms can be present in the foldable tail portion of the occlusion device described herein (cf. FIGS. 2 and 4).

In one embodiment, the foldable head portion and the foldable tail portion have each four arms, wherein each arm comprises one folding segment as shown in FIG. 2.

In the context of the application, the three portions of the foldable section, i.e. the foldable head portion, the foldable tail portion and the waist portion, can be made of three separate portions, which can be comprised of separate films being made of the same or different materials. The material suitable for the use in one, two, or all three portions of the foldable section can be a non-biodegradable or biodegradable polymer or copolymer as described above for the head and the tail tube.

For example, it can be suitable to prepare separate parts of the device from different polymeric materials to specifically adjust the required performance of the material. For instance, the waist portion of the foldable section can be made stiffer or more rigid than the foldable head and tail portions of the foldable section. Otherwise, it is also possible to form the three portions out of the foldable section from a continuous film or sheet, which is divided into the three portions by cutting out some film parts to form a head, tail or waist portion. This is particularly useful if the foldable head and tail portion each have two film-shaped arms.

In this embodiment of the occlusion device described herein and shown, in FIGS. 7a-c for example, the foldable section can comprise more than one film, for example, two, three, four, or even more films arranged on each other. Thus, two or more films can be used to form the foldable section. If two or four films are used, the engaging means can be positioned in the middle of the films, in the case of two films, the engaging means can be provided between the at least two films. If more than one film is used, for example, if two or more films are arranged on each other, the films can be welded together at their one end connected to the head tube and their second end connected to the tail tube and at the parts between the tail portion and the head portion and/or the tail portion, respectively. As an alternative to the welding of the two or more films, the films can be glued, laminated at specific portions, or sewed.

In case, two or more films are arranged on each other, the welding connections are usually not provided in the middle of the two films, i.e. in the middle line between the head and the tail tube, such that the engaging means can be positioned between the two or more films. That means that the engaging means can be inserted between the upper and the lower films in the middle line between the head and the tail tube as shown for example in the embodiment shown in FIG. 7a.

In addition, the connections are generally not provided in those parts of the foldable head and tail portions where folds are provided to allow the folding of the foldable portions. The waist portion can be made such that this portion is not foldable. This can, for example, be achieved, by using a sufficiently thick material, a sufficiently rigid material, or by using additional films arranged at the waist portion and being fixed thereon.

In another embodiment, in which the foldable head portion can comprise three or more arms, e.g. three to eight arms, the folding segment of each arm in the foldable head portion can be located in the portion between the waist portion and the middle of the arm. In addition, the arm can comprise a film portion extending between or spanned over at least a portion of the three or more arms such that the film covers at least the portion between the waist portion and the folding segment of each of the arms. This optional film portion can be used to cover the tissue and to close the defect at least from the front side of the defect.

Figure 4:
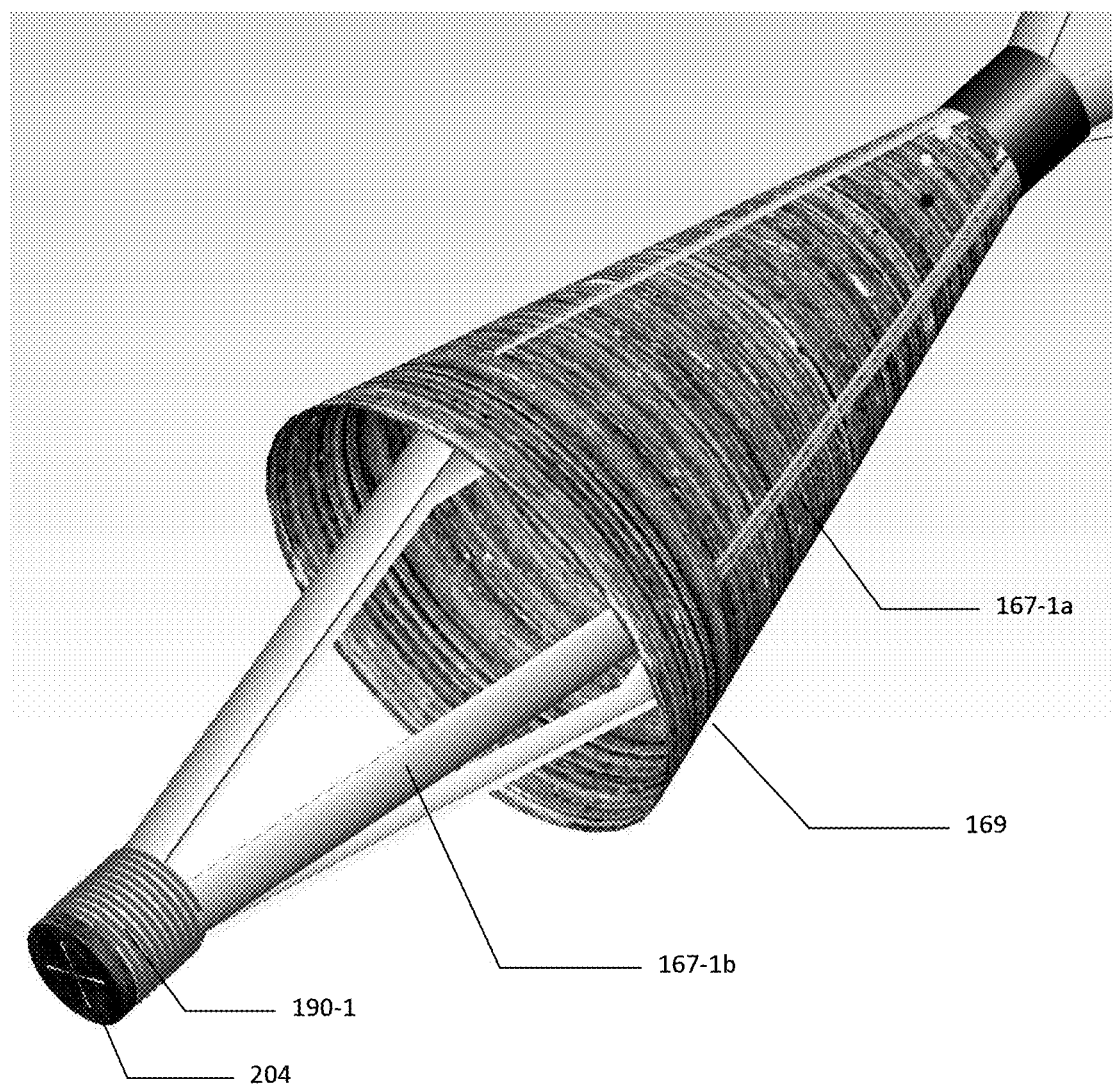
FIG. 4 shows an enlarged perspective view of the posterior portion of the occlusion device shown in FIG. 2.

Analogously, in another embodiment, in which the foldable tail portion can comprise three or more arms, e.g. three to eight arms, the folding segment of each arm in the foldable tail portion can be located in the portion between the waist portion and the middle of the arm. In addition, the arm can comprise a film portion extending between or spanned over at least a portion of the three or more arms such that the film covers at least the portion between the waist portion and the folding segment of each of the arms. This optional film portion can be used to cover the tissue and to close the defect at least from the back side of the defect. This film portion 169 is schematically shown in FIG. 4 for the tail portion. In this Figure the film portion 169 slightly extends over the folding section to enlarge the tissue covering effect.

In addition, in which the foldable head portion and the foldable tail portion can comprise three or more arms, e.g. three to eight arms, the folding segment of each arm in the foldable tail and the foldable head portion can be located in the portion between the waist portion and the middle of the arm. Like in the two embodiments described above, the arm can comprise a film portion extending between or spanned over at least a portion of the three or more arms such that the film covers at least the portion between the waist portion and the folding segment of each of the arms, i.e. in the foldable head and the foldable tail portion. These optional film portions can be used to cover the tissue and to close the defect from the front side and the back side of the defect. If the film portions extend over the folding section, the area to be covered by the respective foldable head or tail portion can be enlarged.

In alternative embodiments of the occlusion device described herein, the film portion can be provided or spanned also over the waist portion. That means that the film portion can cover a part of or the entire waist portion and additionally can cover a part of or the entire head and/or tail portion. Alternatively, in case the film portion is provided at the site of the tail portion, the film portion can cover a part of or the entire tail portion and additionally can cover a part of or the entire waist portion. Of course, as a further alternative, in case the film portion is provided in the head portion and the tail portion, the film portion can be provided to cover also the waist portion. The film portion provided in any of the head, tail or waist portion can be used to enhance endothelialization.

In an embodiment of the occlusion device described before, the film portion can be comprised of a flexible or elastically deformable material. As can be derived from the FIG. 4, during the folding procedure of the foldable section, the film portion near the folding segments will be much more stretched as the film portion near the waist portion. Thus, a sufficient high flexibility of elasticity of the film portions material is needed to avoid any damaging of the film portion during the folding procedure. Of course, the material strength can be adjusted within the film portion such that the flexibility is higher at the end of the film portion which is near the folding segments and which is lower at the end of the film portion which is near the waist portion. For example, this could be done by decreasing the thickness of the material of the film portion from the waist portion to the folding segment.

The size and the form of the foldable head and tail portions can be freely adjusted depending on the size of the defect to be closed. In addition, the dimensions of the foldable head portion and of the foldable tail portion of the occlusion device can be adjusted so that the device can be placed in and pushed through a catheter sheath and has a working size (diameter) of the folded portions in the working structure, i.e. in their folded states, which is sufficient for closing the opening, for example in the septum. Such a transcathether-closeable defect usually has a diameter of up to 40 mm. The diameters of the occlusion devices, i.e. the diameter of the folded portions of the head and the tail portions in their folded states, can be about 70 mm, 60 mm, 50 mm, 40 mm, 30 mm, 20 mm, or can be provided in a size of about 10-16 mm. In one example, the foldable head portion has a diameter of about 12 mm and the foldable tail portion has a diameter of about 16 mm. The size of the folded head portion and the size of the folded tail portion can be adapted such that a defect can sufficiently be closed. Sufficiently closed means in the context of the present invention that after insertion of the occlusion device into an opening, the liquid flow from the back side to the front side and the liquid flow from the front side to the back side of the closed opening can no longer be observed, for example by echocardiography or any other method used in the art to measure the liquid flow through an opening.

The thickness of the arms and of the film portions, if present, of the foldable head and tail portions of the foldable section of the occlusion device can be at least about 10, 20, 30, 40, 50, 60, 70, 80, 90, 100, 110, 120 µm, but below about 500, 450, 400, 350, 300, 250, 200, 190, 180, 170, 160, 150 µm as long as the material has a suitable stiffness to maintain the structure of the arms and a suitable flexibility to be folded during the deployment procedure.

In one embodiment of the occlusion device according to the first aspect described herein, the waist portion can be a cylindrical, hollow tube, such as a polymeric tube. To this tube, one end of the foldable head portion and one end of the foldable tail portion can be fixed, for example by welding or gluing the arms to the waist portion. In an alternative embodiment, the waist portion can be a sheet-like tube, if two arms in sheet form are laid on each other. The hollow tube can receive the deployment means and the engaging means during the deployment procedure of the occlusion device described herein.

The waist portion can be formed to extend through the opening of the defect and can, thus, be adapted to the tissue thickness at the opening or can be elastic enough to accommodate different opening thicknesses. The elasticity can be adjusted by common methods such as the material elasticity, the material thickness, the wall thickness of the tube, and the like. The waist portion can have a length of between about 1 and 10 mm, for example, about 1, 2, 3, 4, 5, 6, 7, 8, 9, or 10 mm. The waist portion can be a tube having an inner diameter of at least about 0.5, 0.6, 0.7, 0.8, 0.9, 1.0, 1.1, 1.2, 1.3, 1.4, 1.5 mm but not more than about 2.0, 2.1, 2.2, 2.3, 2.4, 2.5, 2.6, 2.7, 2.8, 2.9, 3.0 mm, and for example about 1.5-2.0, 1.6-1.9, 1.7-1.8 mm. The wall thickness of the tube, if the waist portion is in the form of a cylindrical tube, can be between about 0.05 and 0.50 mm, for example, about 0.05, 0.06, 0.07, 0.09, 0.11, 0.13, 0.15, 0.17, 0.19, 0.21, 0.23, 0.25, 0.27, 0.29, 0.30, 0.35, 0.40, 0.45 or 0.50 mm. If the waist portion is in the form of a sheet-like tube, the thickness of the wall directly depends on the one or more films used in this part of the foldable section.

In the occlusion device of the first aspect, it can be suitable to prepare separate parts of the foldable section of the occlusion device from different polymeric materials to specifically adjust the required performance of the material. For instance, the waist portion of the occlusion device can be made stiffer or more rigid than the foldable head and tail portions or the film portions of the foldable section. Otherwise, it is also possible to form all parts of the foldable section or of the entire occlusion device from the same material but having specific thicknesses such that each part has the flexibility or stiffness required for its function. For example, in one embodiment the support structures or the waist portion can be stiffer than the foldable head and tail portions of the device. Using different polymeric materials can also serve to alter the biodegradability of different portions of the occlusion device to result in a sequential degradation of different parts of the occlusion device. For example, the material used for the waist portion can be manufactured of a polymeric material which degrades faster than the material used for the proximal and distal support structure. This could result in a closure of the defect without risking a further passage of body fluid from one side of the defect to the other.

In one embodiment of the occlusion device of the first aspect, the entire occlusion device can be made of a polymeric material, like a biodegradable polymer to provide a fully bio-degradable occlusion device. That means that the materials of the above described scaffold and foldable section can be made of a bio-degradable material, particularly of bio-degradable polymers. In this embodiment, the material of the device can be fully biocompatible and can, for example, be desorbed by the body within short time of a view years to several months, such as 10, 9, 8, 7, 6, 5, 4 or 3 months.

Approved by US FDA for other vascular applications, biodegradable polyesters are the most commonly used and promising bio-degradable materials of choice for blood contacting implants. They are biocompatible and can be tailored to degrade within a wide range of time frames. However, the loading and deployment of the occlusion devices usually involve drastic deformation and the polymers behave differently in terms of mechanical properties (e.g., much lower modulus, stress relaxation, and the like) compared with metals. In order to completely replace metal in the occluder design, the polymers need to be carefully selected according to their mechanical behaviors. Meanwhile design should be taken out in a way to make full advantage of the material properties. In a biodegradable ASD/PFO occluder according to the first aspect the material should be adjusted to the specific pull-and-fold mechanism. Therefore, the foldable section of the occlusion device can generally be made of any biodegradable polymer having sufficient physical and mechanical properties for being foldable. Such a polymeric base material can be selected from the group consisting of polycaprolactone (PCL), polylactic acid (PLA), polycaprolactone-polylactic acid copolymer (PCL-PLA copolymer), polyglycolide (PLGA), poly-L-lactide (PLLA), poly-D-lactide (PDLA), polygluconate (PGA), polylactide-polygluconate copolymer (PLGA), polylactic acid-polyethylene oxide copolymers, polyhydroxybutyrate, polyanhydride, polyphosphoester, poly(amino acids), polydioxanone, cellulose, collagen, chitosan and copolymers thereof.

Most bioabsorbable polymers available today, namely polylatic acids (PLA), polycaprolactone (PCL) and polylactic-co-glycolic acid (PLGA) however display a very similar mechanical behavior, with a high Young's modulus and rather low elongation at break values. Sometimes these polymers seem in a pure form inappropriate for this clinical application where highly flexible biodegradable materials are required because of the huge expansion ratio before and after deployment. One of the most practical strategies for tuning the properties of polymers is blending with another polymer or copolymerization. Copolymerization facilitates a broad range of properties, including good mechanical strength, biocompatibility, biodegradability, and processability, which makes them excellent materials for medical application. PCL is for example a good candidate to toughen PLA which may increase the flexibility of PLA chain. The random copolymer of PCL and PLA (PCL-co-PLA) degrades faster than either homopolymers. The rate of degradation increases with the increase of PLA content in the copolymer. The fastest degradation rate is obtained when PLA-PCL is about 70:30, but the degradation rate is still within an suitable range within PLA:PCL of about 90:10-50:50, more particular of about 80:20-60:40. Furthermore, PLA-PCL copolymer has good mechanical and biocompatible properties.

A list of exemplary candidate polymers is shown in the following Table 1. The respective glass transition temperature (Tg) and melting temperature (Tm) have been determined by differential scanning calorimetry (DSC).

TABLE 1

Examples of bio-degradable polymers and their thermal properties

| Materials | Tg (° C.) | Tm (° C.) |
|---|---|---|
| PLA IV2.38 (Purac) | 60 | 175 |
| PLGA 80/20 IV1.7-2.6 (Purac) | 52 | 120 |
| PCL Mw 80K (Aldrich) | −60 | 62 |
| PLA-PCL Copolymer 70/30 IV1.62 (Purac) | 15 | 112 |

In case pure PLA is too stiff, it can be blended into the PLA-PCL copolymer at certain ratios to adjust the Young's modulus within about $1\times10^4$ to about $1\times10^7$ Pa at 37° C., more particularly more than about $1\times10^4$, $2\times10^4$, $3\times10^4$, $4\times10^4$, $5\times10^4$ and less than about $1\times10^7$, $5\times10^6$, $1\times10^6$, $5\times10^5$, $1\times10^5$. If the modulus is too low and a higher modulus is desired, blends with other monomers or filler occlusion (such as, e.g., metal oxides, metal salts such as sulfates, chlorides or the like, organic fillers etc.) are useful, although the degree of stress relaxation is greater than the pure PLA-PCL copolymer. For certain circumstances such as the film portions or the folding segments where low stiffness and high flexibility are required, the pure copolymer can be a good option. Therefore, the physical parameters of the polymeric material can be adjusted to the specific use of the occluder part by general methods outlined above. The skilled person knows mechanical tests for testing the stress relaxation of the respective polymeric materials as it is, for example, shown in FIGS. 4 and 5 and described in Example 7.

For adjusting the performance of the polymers, plasticizers could be used. In the context of the present invention, "plasticizer" generally means a substance added to a polymer material to soften it and to improve flexibility. More particularly, the plasticizer which can be used in the occluder of the present invention can preferably lower the glass transition temperature, Tg, the modulus, i.e. increases the elongation at break, or changes the crystalline behavior of a polymer material or can adjust the melting temperature, Tm. Any known plasticizer can be used in the polymer layer as long as the plasticizer provides the polymer with the above-mentioned properties. The plasticizer may also be biocompatible, especially non-toxic. However, due to the small amount of plasticizer used compared to the entire body mass of a patient, use of a plasticizer that may have some adverse effects on the human body is also within the scope of the invention. Some illustrative examples of plasticizer that can be used in the present invention include, but are not limited to triethyl citrate (TEC), polyalkylene glycols such as polyethylene glycols (PEG) or polypropylene glycols, propylene glycol (PG) glycerol, di-2-ethylhexyladipate (dioctyladipate), di-2-ethylhexylphthalate (dioctylphthalate), dicyclohexylphthalate; diisononyladipate; diisononylphthlate; n-butyl benzyl phthalate, 1,3-butylene glycol/adipic acid polyester (1700-2200 MW) containing 16 weight percent terminal myristic, palmitic and stearic acid ester functionality. Other examples of plasticizers include epoxidized butyl esters of linseed oil fatty acid, epoxidized linseed oil or epoxidized soya oil. Examples of polyalkylene glycols include low molecular weight (MW) compounds having an MW of about 60-about 8000, or about 100-6000, about 100-5000, about 100-4000, or about 150-2000. Illustrative examples include diethylene glycol, triethylene glycol, dipropylene glycol, or tripropylene glycol, too name only a few.

The amount of plasticizer is not limited but is generally adjusted such that the biodegradable polymer material maintains mechanical integrity during its use, including for example, during the storage and upon deployment. In some embodiments of the invention, the plasticizer can be contained in one or all of the polymer materials in an amount of about 1-about 30 wt %, or about 1-25 wt %, about 2-25 wt %, about 3-25 wt %, about 4-25 wt %, about 5-25 wt %, about 6-25 wt %, about 2-20 wt %, about 3-20 wt %, about 4-20 wt %, or about 5-20 wt %, based on the dry weight of the polymer material. In line with the above, the amount of plasticizers can for example be about 1, 2, 3, 4, 5, 6, 7, 8, 9, 10, 12, 15, 17, 19, 21, 23, 25, 27, or 29 wt %, based on dry weight of the respective polymer material.

In an alternative embodiment of the occlusion device of the first aspect, one or more elements selected from the head tube, the tail tube, the engaging means and the foldable section can be made of a material comprising a therapeutically active agent or a mixture of therapeutically active agents.

In the context of the present invention, the term "therapeutically active agent" generally means a therapeutic or pharmaceutical agent, which can be mixed into the polymer composition, or impregnated or incorporated into the tube, films, engaging means and wire structures to provide drug-containing tubes, films, engaging means or wires. The drug can be any therapeutic or pharmaceutical agent suitable for use in drug-containing materials for occluders. Various examples include, but are not limited to, antiproliferative/antimitotic agents including natural products, such as vinca alkaloids (e.g. vinblastine, vincristine, and vinorelbine), paclitaxel, epidipodophyllotoxins (e.g. etoposide, tenipoxide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiproliferative/antimitotic alkylating agents such as nitrogen mustards (such as mechlorethamine, cyclophosphamide and analogs, melphalan, chlorambucil), ethylenimines and methylmelamines (hexamethylmelamine and thiotepa), alkyl sulfonates-busulfan, nirosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase); antiplatelet (such as aspirin, dipyridamole, ticlopidine, clopidogrel, abciximab); antimigratory; antisecretory (such as breveldin); antiinflammatory: such as adrenocortical steroids (cortisol, cortisone, fludrocortisone, prednisone, prednisolone, 6-alpha-methylprednisolone, triamcinolone, betamethasone, and dexamethasone), non-steroidal agents (such as salicylic acid derivatives e.g. aspirin); para-aminophenol derivatives (e.g. acetaminophen); indole and indene acetic acids (such as indomethacin, sulindac, and etodalac), heteroaryl acetic acids (such as tolmetin, diclofenac, and ketorolac), arylpropionic acids (such as ibuprofen and derivatives), anthranilic acids (such as mefenamic acid, and meclofenamic acid), enolic acids (such as piroxicam, tenoxicam, phenylbutazone, and oxyphenthatrazone), nabumetone, gold compounds (such as auranofin, aurothioglucose, gold sodium thiomalate); immunosuppressive (such as cyclosporine, tacrolimus (FK-506), sirolimus (rapamycin), azathioprine, mycophenolate mofetil); angiogenic such as vascular endothelial growth factor (VEGF), fibroblast growth factor (FGF); nitric oxide donors; anti-sense oligo nucleotides and combinations thereof.

The therapeutically active agent can particularly be selected from a drug, an antibiotic, an anti-inflammatory agent, an anti-clotting factor, a hormone, a nucleic acid, a peptide, a cellular factor, a growth factor, a ligand for a cell surface receptor, an anti-proliferation agent, an anti-thrombotic agent, an antimicrobial agent, an anti-viral agent, a chemotherapeutic agent, or an anti-hypertensive agent or any combination thereof to improve the sealing effect, the healing process, or preventing thrombi, for example. However, the agent is not limited to these examples. Heparin is well known for anticoagulation and has been used to prevent clotting in many cardiovascular applications. In an alternative embodiment, for example, heparin can be included as an anti-clotting factor, for example by blending or impregnating it into the surface of the polymeric material to provide a better blood biocompatibility.

In some embodiments of the invention, the anti-thrombotic drug can, for example, be selected from small organic molecules such as clopidogrel, triflusal, or analog salicylic acid derivatives or a protein such as hirudine or thrombin or any combination thereof. Illustrative examples of an anti-restenotic drug are sirolimus, also called rapamycin paclitaxel, and evolimus.

Another example of a therapeutically active agent that may be used in the polymeric material is the compound known as elarofiban (b-[[[(3R)-1-[1-oxo-3-(4-piperidinyl) propyl]-3-piperidinyl]carbonyl]amino]-3-pyridinepropanoic acid, (bS)-(9CI), RWJ-53308) and elarofiban analogs that are described in International patent application WO2005/087266.

In this context, it is noted that the therapeutically active agent (drug) to be incorporated into one or more polymeric materials of the occlusion device described herein can be a small organic molecule, a protein or a fragment of the protein, a peptide or a nucleic acid such as DNA or RNA. The term "small organic molecule" as used herein typically denotes an organic molecule comprising at least two carbon atoms, but preferably not more than 7 or 12 rotatable carbon bonds, having a molecular weight in the range between 100 and 2000 Dalton, or between 100 and 1000 Dalton, that optionally can include one or two metal atoms. The term "peptide" as used herein typically refers to a dipeptide or an oligopeptide with 2-about 40, 2-about 30, 2-about 20, 2-about 15, or 2-about 10 amino acid residues. The peptide may be a naturally occurring or synthetic peptide and may comprise—besides the 20 naturally occurring L-amino acids—D-amino acids, non-naturally occurring amino acids and/or amino acid analogs. With "protein" is meant any naturally occurring polypeptide that comprises more than 40 amino acid residues. The protein can be a full length protein or a truncated form, for example, an active fragment. Illustrative examples of proteins include, but are not limited to antibodies or other binding proteins with antibody like properties (for example, affibodies or lipocalin muteins knows as "Anticalins®") for selected cell receptors, growth factors such as VEGF (Vascular Endothelial Growth Factor) and similar factors for transmitting signals, cardiovascular therapeutic proteins or cardiac hormones and active fragments thereof or prohormones or preprohormones of such cardiac hormones (these hormones or the prohormones can either be peptides as defined herein, if they have less than 40 amino acid residues of a protein, should there polypeptide sequence contain more the 40 amino acid residues). Further examples for cardiovascular therapeutic agents can be peptides or DNA such as the DNA for nitric oxide. Examples of nucleic acid molecules include sense or anti-sense DNA molecules (if expression of a target gene is to be controlled) or the coding sequence (either alone or in gene-therapy vector, for example) of a therapeutically active protein that is to be produced. In such a case, the nucleic acid may code for a protein that promotes wound healing as described in International patent application WO 97/47254, for example.

All drugs or therapeutically active agents mentioned above can be used alone or in any combination thereof in the polymer material of this embodiment of the invention. If a therapeutically active agent is contained, the agent can be incorporated into the polymer material by admixing, impregnating, or the like, wherein the agent does not necessarily need to be uniformly distributed within the polymer material.

The amount of the therapeutically active agent (or 2 or more therapeutically active agents together) in the polymeric material is not limited and can be as high as wanted as long as the physical properties of the polymer material, especially the glass transition temperature and the melting temperature, are not adversely affected. In some embodiments, the amount of the therapeutically active agent, based on the dry weight of the polymer material that contains the therapeutically active agent, may be up to about 35 wt %. The therapeutically active agent may be present in an amount of 0.1 to 35 wt %, 1 to 35 wt % or 1 to 10, 15, 20, 25 or 30 wt % based on the dry weight of the polymer material that contains the agent. In this context, it is again noted that it is possible to include more than one therapeutically active agent of the same or different type into a polymer material of the films, arms, engaging means or wires, for example, an anti-restenotic drug and an anti-inflammatory drug or two anti-thrombotic drugs.

In a further embodiment of the occlusion device described herein one or more elements of the head tube, the tail tube, the engaging means or the foldable section can comprise a radiopacifier deposited at its surface and/or blended in the material the elements comprise. For example, the radiopacifier can be comprised in the head tube, in the tail tube, or in the arms and film portions of the foldable section.

The radiopacifier can for example be a material including, but not limited to, metals, metal oxides, metal salts, such as gold particles, bariums salts or bismuth glasses, for example. In the present embodiment, $BaSO_4$ can be used for radio-opacity. In the films, the radiopacifier can be incorporated into the polymeric material by solution casting in an amount of more than 0.1, 0.2, 0.3, 0.4, 0.5, 1.0, 1.5, 2.0, 2.5, 3.0, 3.5, 4.0% (w/w) to less than 50, 45, 40, 35, 30, 25, 20, 15, 10, 9, 8, 7, 6, 5% (w/w) as long as the films are provided with radio-opacity for making the device visible by means of fluoroscopy, for example, during the deployment procedure. In the film portions or the sheet-like arms, the radiopacifier can often be less concentrated compared to the head tube or the tail tube to avoid any affecting of the physical properties of the polymers or copolymers. In other parts of the occlusion device, for example in the waist portion of the foldable section, the amount of radiopacifier can be increased because a higher stiffness of the film is suitable and the visibility of the occlusion device can simultaneously be improved. For example, the films of the head and the tail portion can be solution casted with about 4% (w/w) $BaSO_4$. The $BaSO_4$ also enhances stiffness and non-stickiness. The waist portion can, for example, be made of a copolymer with about 40% (w/w) $BaSO_4$ for providing good radio-opacity.

It is also possible to use additional films in the waist portion, especially, if the waist portion is made of a sheet-like tube comprised of two overlaying films, to provide the occlusion device with radio-opacity. These films are called waist markers and they can be provided with a high amount of radiopacifiers, for example about 40% $BaSO_4$, while the other parts of the occlusion device are not provided with a radiopacifier or provided with a lower amount of radiopacifier.

In the following the delivering system according to the second aspect of the application will be described in detail. In the context of the application, the term "delivering system" means a system which is suitable to deliver the occlusion device of the first aspect to the desired place in the body of a subject, like a mammal (including, e.g.; primates including humans, rodents such as mice and rats, and ungulates such as pigs and the like) to be treated.

The delivering system can be adapted to be included into a sheath of a catheter and comprises at least one first delivering means and at least one second delivering means. The first delivering means can be adapted to push the occlusion device through the sheath and to guide the head portion of the foldable section in a position at the front side of an opening, like a tissue defect, for example. The second delivering means can be adapted to move the tail tube into the direction of the head tube to allow the tail tube to be moved against the back side of the tissue.

In one embodiment of the delivering system according to the second aspect, the first delivering means can be a delivering rod extending through the tail tube towards the head tube of the occlusion device and being removably connected to the head tube. Thereby the delivering rod can guide the head tube of the occlusion device through the sheath to the target site. The delivering rod can be made of a polymer or metal rod. The material can be a shape memory material such as a metal like a Ni—Ti alloy (e.g., Nitinol), Cu—Zn alloy, Fe—Ni—Al alloy or a shape memory polymer so that the head tube together with the head portion of the foldable section can be guided along the sheath to the target site. The delivering rod can have a diameter of about 0.3-1.0 mm, 0.4-0.9 mm, 0.5-0.8 mm, 0.6-0.7 mm, especially about 0.65 mm, which is used to push the entire device into the sheath and to reach the opening to be closed.

In an embodiment of the first delivering means, the delivering rod can have a threaded exterior surface at its end facing the tail tube. The thread at its end enables a safe engagement into a threaded interior surface of the head tube. The threads are adjusted such that the delivering rod can be attached to the head tube by means of a clockwise turn and can be detached off the head tube by an anti-clockwise turn of the delivering rod. Alternatively, the threads can be adjusted such that the delivering rod can be attached to the head tube by means of an anti-clockwise turn and can be detached off the head tube by means of a clockwise turn of the delivering rod.

In another embodiment of the delivering system described herein, the delivering rod can be removably connected to the head tube by means of a slip-fit mechanism. That means that the end of the delivering rod and the interior of the head tube are adjusted such that they fit into each other and the delivering rod can be pressed into the head tube by means of a short pushing force of the delivering rod into the direction of the head tube and can be released from it by means of a short pulling force of the delivering rod into the backwards direction away from the head tube. Thereby, the hollow cylindrical head tube can have a conical shape such that its cross section at the opening towards the tail tube is bigger than the cross section at the tip of the head tube showing away from the tail tube. Of course, to improve the fitting mechanism, the end of the delivering rod can also have a conical shape such that it fits to the conical shape of the interior of the head tube. In addition to the above conical shape or instead of this shape, the interior of the head tube or the exterior of the tip of the delivering rod or both can have a notched surface to increase the friction force between the both surfaces.

The second delivering means can, for example, be a deployment tube. The deployment tube can be made of a polymeric material which is not hazardous for the patient. However, any other of the afore-mentioned non-biodegradable or biodegradable polymer materials could be used for the deployment tube. The material of the deployment tube can be any material if it is flexible enough to be inserted into a sheath of a catheter. The tube can be a cylindrical hollow polymeric tube, usually made of a biostable polymer, such as a PTFE tube having an outer diameter of about 1.0-2.0 mm, 1.2-1.9 mm, 1.4-1.8 mm, 1.6-1.7 mm, especially about 1.65 mm and having an inner diameter of about 0.4-1.1 mm, 0.5-1.0 mm, 0.6-0.9 mm, or 0.7-0.8 mm. The tube can simultaneously be used as an housing of the first delivering means.

In an embodiment of the second delivering means, the deployment tube can have a threaded interior surface at its end facing the tail tube. The thread at its end could be used to removably connect the deployment tube to the tail tube, if the tail tube has at its exterior surface a respective thread. Thus, the threads are adjusted such that the deployment tube can be attached to the tail tube by means of a clockwise turn and can be detached off the tail tube by an anti-clockwise turn of the deployment tube. Alternatively, the threads can be adjusted such that the deployment tube can be attached to the tail tube by means of an anti-clockwise turn and can be detached off the tail tube by means of a clockwise turn of the deployment tube.

The delivering system according to another embodiment can further comprise a deployment wire removably connected to the delivering wire of the occlusion device, if the engaging means is in the form of a delivering wire. The deployment wire can be housed in the deployment tube of the delivering system.

The deployment wire can be in a linear form or can be in a loop form. If the delivering wire is in loop form, it can be adapted to be removed from the deployment tube, for example, by pulling at one end of the deployment wire. The deployment wire can be any surgical suture as described above for the delivering wire. The diameter of the deployment wire can be between 0.2 and 0.4, between 0.21 and 0.35, between 0.21 and 0.30 mm, for example 0.22 mm (e.g. a Nylon wire like PDS II 4/0 suture).

The delivering system according to a further embodiment of the second aspect of the application can further comprise a retrieval wire anchored at the tail tube of the scaffold of the occlusion device and/or the tail portion of the foldable section of the occlusion device. Such a retrieval wire could, for example be used, if the deployment tube has no thread in its interior. Alternatively, the retrieval wire can also be anchored at the foldable tail portion of the foldable section of the occlusion device. For example, in one embodiment, the retrieval wire can form a loop running through the tail portion of the foldable section of the occlusion device. The retrieval wire can be a metal wire or can be made of any polymeric material as discussed above for the head or tail tube of the occlusion device of the first aspect of the application.

The wires of the delivering system such as the deployment wire or the retrieval wire, if present, can be made of any surgical suture such as non-absorbable or absorbable sutures described above for the delivering wire. In an exemplary embodiment the retrieval wire can be a Nylon wire of a PDS II 2/0 suture. The diameter of the metal wires or of the polymer sutures of the retrieval wire can be in the range of about 0.2-0.5 mm, 0.25-0.45 mm, 0.3-0.4 mm, especially about 0.36 mm.

The delivering system according to the second aspect can further comprise a sheath adapted to include at least the occlusion device of the first aspect and the first and second delivering means of the delivering system.

In a third aspect, the present application relates to a kit comprising the above described occlusion device of the first aspect and the above described delivering system of the second aspect. The kit can be preloaded in a sheath or can be prepared for preloading the occlusion device and the delivering system. Generally, the kit is provided in a package which can be sterilized. The sterilization can be carried out by any conventional process as long as the package with the kit is sufficiently sterilized. An example of such conventional sterilization processes is ethylene oxide (ETO) sterilization in a standard ETO sterilization pouch. The kit is sealed in a package and then over at least 6 hours purged with ETO at about 37° C., usually followed by additional ETO purging of ETO gas at ambient temperatures. The additional purging step can be 5 hours or more, such as 6, 7, 8, 9, 10, 12, 14, 16, 18, 20, 22, 24 hours, especially about 16 hours. Therefore, in one embodiment of the third aspect, the kit is provided in a sterilized package.

In the kit of the third aspect, the deployment tube can house the first delivering means such as the above described delivering rod or the second delivering means such as the above described deployment tube. In addition, the above described retrieval wire can be housed in the deployment tube to prevent that the rods or wires are entangled during the deployment procedure of the occlusion device.

According to a fourth aspect, a method of closing an anatomical defect in a tissue comprising an opening connecting a front side and a back side of a tissue is provided. In this context, the term "closing an anatomical defect" can mean a surgical treatment of a patient in need of such a treatment or can be an in vitro method where defects at tissues outside the patient can be treated. The method of this aspect of the invention comprises the steps of providing a sheath into which an occlusion device according to the first aspect and a delivering system of the second aspect or a kit of the third aspect have been inserted, pushing the occlusion device through the sheath to the site of the anatomical defect by using the first delivering means of the delivering system, pushing a head tube of a scaffold of the occlusion device and a foldable head portion of the foldable section of the occlusion device out of the sheath and through the front side of the tissue, folding the foldable head portion by moving the head tube of the occlusion device in the direction of the front side of the tissue by means of the first delivering means to close the defect from the front side, withdrawing the sheath to release the waist portion in the opening and the foldable tail portion at the back side of the tissue, and moving the tail tube of the occlusion device against the back side of the tissue by means of the second delivering means of the delivering system to fold the foldable tail portion and locking the occlusion device at the anatomical defect from the back side of the tissue.

In the step of pushing a head tube of a scaffold of the occlusion device and a foldable head portion of the foldable section of the occlusion device out of the sheath and through the front side of the tissue, it is either meant that the sheath passes through the opening while the foldable head portion and the head tube are pushed out of the sheath or the sheath is at the front side of the defect while the foldable head portion and the head tube are pushed out of the sheath.

In an embodiment of the method of this aspect, the method can optionally comprise steps of retrieving the delivering system out of the sheath of the catheter. The step of retrieving the delivering system can comprise the steps of withdrawing the first delivering means removably connected to the head tube of the occlusion device and removing the second delivering means by withdrawing it out of the catheter.

In another embodiment of the method of the fourth aspect, a repositioning of the occlusion device can be carried out if, for example, the foldable tail portion of the foldable section has accidentally been released or has been released wrongly during the deployment procedure. The reposition procedure can be used, for example, if the foldable head portion of the films is released wrongly in the front side of the opening. In this case, the method can comprise a re-anchoring step, for example, wherein the sheath and the optional retrieving wire are held in position, the first delivering means is moved forward to unfold the folded head portion and then re-anchoring is performed by folding the foldable head portion of the foldable section of the occlusion device again. In an alternative embodiment of the re-anchoring procedure, the unfolding step can be combined with holding the tail tube by means of the second delivering means in position. This could be done if the second delivering means is a deployment tube having a thread at its tip and the deployment tube is connected via this thread to the threaded tail tube. In this case, a retrieving wire is not necessary.

In the retrieving procedure, a correction of the sealing procedure can be carried out, wherein the method of the fourth aspect further comprises a correction step of the sealing procedure. In this correction step, the first delivering means is held in position and the second delivering means or the retrieving wire, if present, is used to unfold the entire occlusion device and to pull back the foldable tail portion of the occlusion device into the sheath again and repeating the folding procedure referred above. If no retrieving wire is present, the second delivering means can be a deployment tube having a thread at its tip. Then, the deployment tube could be connected via this thread to the threaded tail tube to unfold the entire occlusion device by moving the tail tube and backwards. This procedure could also be used to pull the entire occlusion device back into the sheath if the closing procedure need to be interrupted or a new occlusion device needs to be used.

It is also within the above definition of the method to use the occlusion device of the first aspect and the delivering system of the second aspect or the kit of the third aspect in a transcatheteral closure of an anatomical defect in tissue like a septal defect or shunt in the heart or the vascular system. Septal defect can be in this context any defect including, but being not limited to, atrial septal defects, ventricular septal defects, patent ductus arteriosus, or patent foramen ovale.

In an embodiment of the method of the fourth aspect, the method can be used for facilitating the closure of a patent foramen ovale. In this embodiment, the same procedure as described before can be used, wherein the head portion of the foldable section is anchored at least at a portion of the septum primum in the left atrium of the heart and another portion of the head portion of the foldable section is anchored against the septum secundum of the heart.

Figure 10:
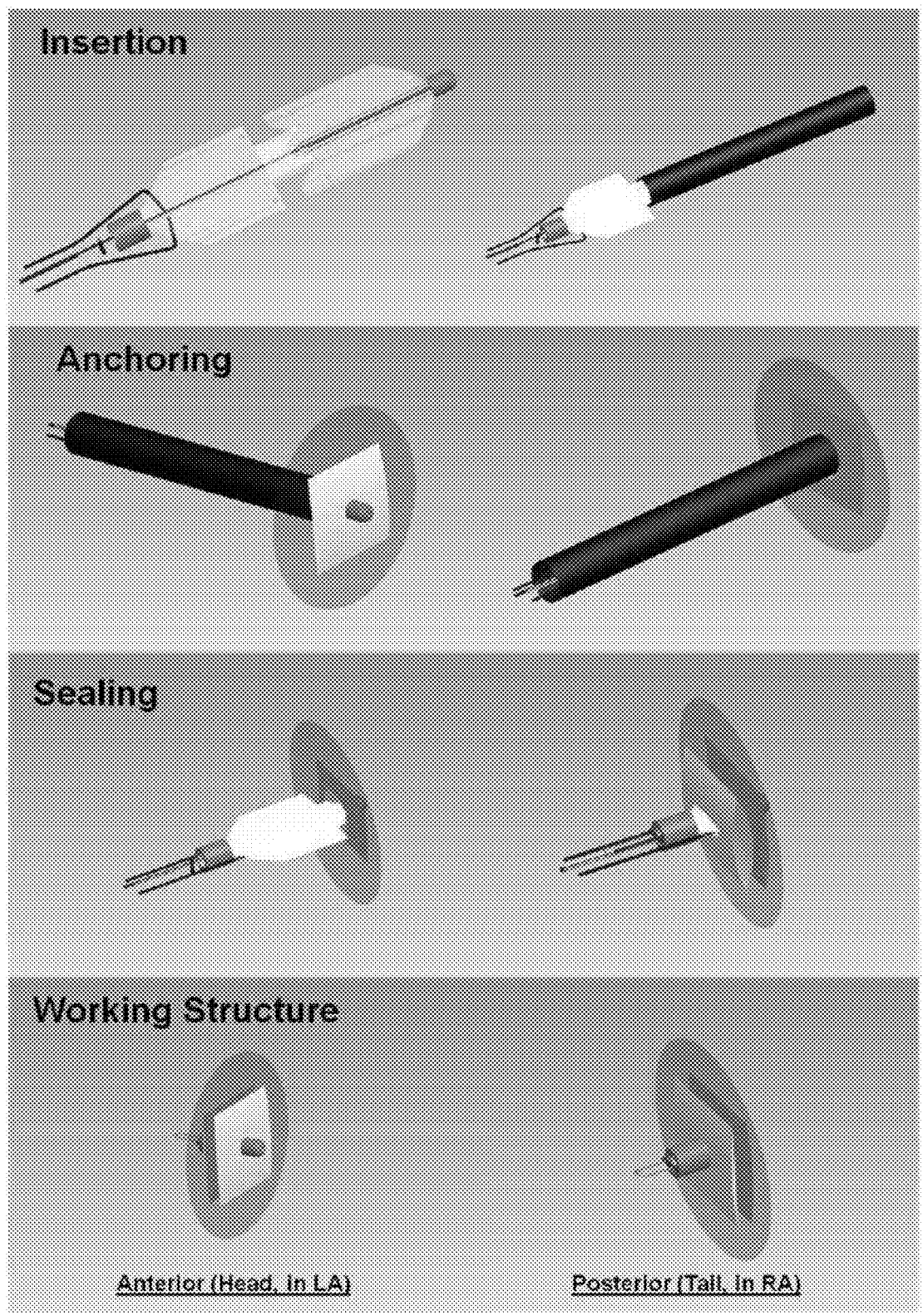
FIG. 10 shows the construction and the functioning of one particular embodiment of an occlusion device of the present invention by schematic views of each of the deployment steps as well as the final working structure of the occlusion device from the front side (Anterior or head portion, positioned in the left atrium (LA) of the heart) and the back side (Posterior or tail portion, positioned in the right atrium (RA) of the heart) of the tissue. The disc in the working structures is an atrial septal defect/patent foramen ovale (ASD/PFO) model.

The deployment procedure covered by the fourth aspect of the present invention comprises in a particular embodiment the following steps. This embodiment is shown in FIG. 10 for facilitating the understanding of the general concept of the present invention. The method comprises the steps of insertion, anchoring, optionally reposition, sealing, optionally retrieval of the occlusion device of the first aspect by means of the delivering system of the second aspect, and then the retrieval of the delivering system. In the FIG. 10, the procedure is described on the basis of an in vitro method, which is made on an ASD/PFO. As occlusion device an occluder described herein is used which has two sheet-like arms in each of the foldable head portion and the foldable tail portion and has a delivering wire as engaging means. The method generally comprises the following steps:

1) Device Preparation

The occlusion device can be assembled with the delivering system as described above or can still be provided in a preloaded state, for example in the form of a kit according to the third aspect. At first the first delivering means, e.g. a delivering rod, can be removably connected to the head tube of the occlusion device. In a second step, a deployment wire and/or a retrieving wire can be housed inside the second delivering means, which is in this embodiment a deployment tube having an inner diameter large enough for housing the respective wires.

2) Insertion

By pushing the delivering rod alone, the occlusion device can be inserted into a catheter sheath, for example a sheath usually used for heart catheter applications like an 11F sheath. The occlusion device can be guided by the delivering rod to the end of the sheath which is shortly behind the opening.

3) Anchoring

The occlusion device utilizes a "pull-fold" mechanism to achieve anchoring and sealing at the front side of the septum. More particularly, when the sheath crosses over the septum, the delivering rod can be pushed forward so that the foldable head portion appears out of the sheath. Then, the film or the films of the foldable head portion can, if necessary, be allowed to unfold at the front side of the tissue, for example in the left atrium (LA), for about 30 s, for example, to totally unfold the head portion of the films. This unfolding of the films can be accomplished, for example, by means of shape memory properties or the rigidity of the film material. If the films are totally unfolded, the sheath and the deployment tube can be held in position and the delivering wire, optionally via the deployment wire, can be pulled back to fold the foldable head portion such that the films of the head portion anchor against the septum.

4) Reposition

If the head portion of the foldable section were released wrongly in the left atrium (LA) or the position of the occlusion device should be repositioned due to another reason, the sheath and the retrieving wire, optionally via the deployment wire, can be held in position and the delivering rod can be pushed forward to unfold the head films. The re-anchoring step (step 3) of the occlusion device can be performed again.

5) Sealing

If the anchoring is satisfactory, the delivering rod can be held in position, the sheath can be slightly withdrawn to release the foldable tail portion whereby the waist portion of the film stays in the hole or defect. The films of the foldable tail portion can, if necessary, be allowed to unfold in the right atrium (RA) for about 30 s, for example. The delivering rod and the delivering wire, optionally via the deployment wire, can be held in position. Then the second delivering means, for example a deployment tube, can be pushed to move the tail tube into the direction of the head tube. Thereby, the films of the foldable tail portion of the foldable section are folded into the working structure. As shown in FIG. 6, optionally a lock tube is simultaneously pushed forward, if the tail tube has no looking mechanism, so that the delivering wire can be engaged at the tail tube or alternatively at a lock tube. Due to this engagement of the delivering wire, the working structure shown in the bottom of the FIG. 6 can be maintained even if the delivering system and the catheter have been withdrawn.

6) Device Retrieval

If the foldable tail portion has, for example, accidently been released in the left atrium in step 5, the delivering rod can be held in position and the retrieving wire can be pulled back to unfold the entire device. Then, the films of the foldable tail portion of the foldable section of the occlusion device can be pulled back into the sheath again and the sealing procedure of step 5 can be repeated again. This retrieval step can be repeated until the sealing is successful.

7) Retrieval of Delivering System

If step 5 results in a satisfactory positioning of the device, the deployment wire and the retrieving wire can be retrieved, for example, by pulling at one end of the looped deployment wire and pulling it out. Afterwards the deployment tube, the delivering rod and the sheath can also be pulled back to retrieve all parts of the delivering system and to leave the occlusion device in its folded working structure locked by means of the engagement of the delivering wire at the tail tube, optionally via the lock tube.

In the following the present invention is described in detail by the following non-limiting Working Examples and Examples. In the Working Examples, the structural concept of the occlusion device of the first aspect is described at hand of several particular embodiments. Of course the present invention is not limited to these embodiments and the skilled person knows several modifications and equivalent embodiments of the occlusion device when considering the above detailed description of the invention.

Working Example 1

In the embodiment shown in the FIGS. 2 to 5, an occlusion device of the first aspect is shown which can be adjusted for the use as an ASD/PFO occluder. The occlusion device of this embodiment comprises a head tube, a tail tube and a tube-like engaging means integrally provided with the head tube as scaffold. The foldable section comprises in the foldable head portion four sheet-like arms extending from the head tube to the waist portion, wherein each arm has one folding segment in the middle of the length between the head tube and the waist portion. The foldable tail portion similarly comprises four sheet-like arms extending from the waist portion to the tail portion and each having one folding segment (the folding segment is shown in FIG. 4). In addition to the four arms, the foldable tail portion of the foldable section comprises a film portion spanned over the four arms in a tube-like form and extending from the waist portion to the folding segment of each arm, wherein the film portion can extend a little bit over the folding segments as it is shown in FIG. 4, for example.

The occlusion device of this embodiment is composed of head (for the left atrium), waist and tail (for the right atrium) portions, which will be positioned into the left atrium (LA), ASD/PFO tunnel (the "opening" or "defect") and right atrium (RA), respectively. The arms will be folded into the working structure (as shown in FIG. 5) to seal the ASD/PFO (not shown).

In FIG. 2, an exploded perspective view of the occlusion device of the first aspect of the present invention and components of the delivering system according to the second aspect of the present invention are shown. A left atrial patch (120) for closing the defect from the front side of the tissue comprises a head tube (110-1), and a foldable head portion consisting of four separate arms which can be differentiated into half-front left atrial films (127-1*a*) and half-back left atrial films (127-1*b*) (see the enlarged view of the components of the left atrial patch in FIG. 3). The films of the arms are made from a polymeric material and have a folding segment in the middle of the arms to separate the arms into the half-front and half-back left atrias films (127-1*a,b*). The folding segment is made of the same polymeric material, but the material in the folding segment is thinner as in the other parts of the arms. The head tube has a hollow interior with a thread therein so that the deployment rod (130) as first delivering means of the delivering system, which is also threaded at the end, can be attached to the head tube (110-1) with a clockwise turn and be detached off the head tube (110-1) by an anti-clockwise turn of the deployment rod (130).

The right atrial patch (160) for closing the defect from the back side of the tissue comprises a tail tube (190-1), and a foldable tail portion consisting of four separate arms which can be differentiated into half-front right atrial films (167-1*a*) and half-back right atrial films (167-1*b*) and a right atrial film portion (169) (see the enlarged view of the components of the right atrial patch in FIG. 4). The tail tube has a hollow cylindrical tube shape and has a threaded exterior surface so that the deployment tube (315) as second delivering means of the delivering system, which also has a threaded interior at its end, can be attached to the tail tube (190-1) with a clockwise turn and be detached off the tail tube (190-1) by an anti-clockwise turn of the deployment tube (315).

The occlusion device described herein in greater detail further comprises a hollow tube (113) made from a polymeric material as engaging means which is integrally provided with the head tube (110-1). The engaging means is further adapted to be engageable at the lock (204) integrally provided with the tail tube (190-1). As shown in FIG. 4, the lock is made of a flexible material and has two crossed slots. The engaging means can be put through the crossed slots to be fastened after the occlusion device has been folded into its working structure as is shown in FIG. 5.

The deployment tube (315) can be used, as it is shown in this embodiment of the occlusion device of the present invention, as a rod housing and as a second delivering means. The deployment tube (315) is flexible enough for pushing the occlusion device along the sheath (not shown) as well as pulling back the occlusion device to the sheath when a retrieval of the occlusion device is needed.

Working Example 2

In the embodiment shown in the FIGS. 7*a-c*, an occlusion device of the first aspect is shown which can be adjusted for the use as an ASD/PFO occluder. The occlusion device of this embodiment comprises two copolymer films of about 12 mm×50 mm in its unfolded structure. The occlusion device of this embodiment is composed of front (for the left atrium), waist and tail (for the right atrium) portions, which will be positioned into the left atrium (LA), ASD/PFO tunnel (the "opening" or "defect") and right atrium (RA); respectively. The films will be folded into the working structure (as shown in FIGS. 3b and c) to seal the ASD/PFO.

In FIG. 10, several deployment steps are shown for the occlusion device shown in FIGS. 7a-c including the folding of the foldable head portion of the foldable section at the front side of the tissue and anchoring the occlusion device at the front side of the tissue by means of pushing the foldable head portion and the head tube out of the sheath and folding it by moving the head tube backwards, i.e. in the direction of the tail tube. Then, the foldable tail portion of the foldable section at the backside of the tissue can be deployed from the sheath and folded by means of moving the tail tube in the direction of the head tube, thereby sealing the opening from both sides by means of the folded films. At the bottom of FIG. 10, the occlusion device according to this particular embodiment is shown in its final working structure from the front side in the left picture and the backside in the right picture. Also, the occlusion device is not restricted to this particular embodiment, but several modifications of the design of the foldable sheets or the scaffold parts can be derived from the general description of the occlusion device and the exemplified embodiments described above.

The construction of the scaffold and the foldable portions of the occlusion device are shown in the FIGS. 7a-c in greater detail. In the following, the technical function of each part of the occlusion device of this working example will be explained.

FIG. 7a shows structural details of the occlusion device in its unfolded state. As can be seen from FIG. 7a, the head tube (10) is positioned at the anterior part of the occlusion device. In this embodiment, the delivering rod (21) which is the first delivering means of the delivering system of the second aspect can be removably arranged at the head tube (10). At the head tube (10), one or more films (11) of the foldable section can be connected. In the embodiment as shown in FIG. 7a, two films (11) extend in a sheet-like form from the head tube (10) to the tail tube (12) where they are respectively connected at their ends, for example, by laminating, gluing, sewing or welding.

In FIG. 7a are also shown elements of the delivering system of the second aspect. In this embodiment, the first delivering means of the delivering system is adapted to push the occlusion device through a sheath and to guide the head portion of the foldable section in a position at the front side of the tissue. The first delivering means is in this embodiment a delivering rod (21) extending through the tail tube of the occlusion device and towards the head tube of the occlusion device and being removably connected to the head tube. The delivering rod can be inserted/connected into/to the head tube (10) by a slip fit connection as used in the present embodiment. That means that the delivering rod (21) can be inserted into the head tube (10), which can also be a cap closed at its tip and can easily be removed from of the head tube (10) by pulling it away from the head tube. To remove the delivering rod (21) from the head tube the position of the head tube should be fixed. This can for example be achieved by pulling the delivering rod (21) away from the head tube (10) while the head tube is hold in position at the anterior side of the defect after it has been anchored at the anterior side of the defect. Anchored means that the foldable head portion has been folded at the anterior side of the defect and, thus, the head tube cannot be pulled back through the opening of the defect.

During the deployment procedure, the foldable head portion of the occlusion device can be anchored at the anterior side of the tissue defect. The delivering rod (21) of the delivering system can be arranged in the occlusion device, as it is shown in the embodiment shown in FIG. 3a, for example, between the two sheet-like films of the foldable section of the occlusion device and can extend through the tail tube (12) while it can optionally also extend over the lock tube (13) which can be arranged, if provided, behind the tail tube (12).

The occlusion device of the embodiment shown in FIGS. 7a-c comprises in its scaffold a delivering wire (14) in loop form ("loop wire") which is connected with both ends at the head tube (10). The delivering wire (14) does not need to extend all the way down to the tail tube (12) in the unfolded state of the occlusion device. However, in the working structure shown in FIGS. 7b and c, that means after the occlusion device has been folded in its working structure, the delivering wire (14) can extend through the tail tube (12) and the optional lock tube (13) which can be arranged behind the tail tube (12). When extending through the tail tube (12) and optionally the lock tube (13) the delivering wire (14) can be engaged directly at the tail tube (12) or optionally at the lock tube (13) as it is shown in the FIG. 7c. Thus, the folded structure can be locked by engaging the delivering wire (14) at the tail tube (12).

In the embodiment shown in FIG. 7a, the delivering wire (14) is connected to a a deployment wire (22), which can also be in a loop-form in the unfolded state of the occlusion device. The deployment wire can facilitate the deployment procedure. The deployment wire can removably be connected to the delivering wire of the occlusion device and can, thus, extend the delivering wire such that the delivering wire can be made so short that it can be engaged at the tail tube, but need not be cut after the deployment of the occlusion device. This embodiment allows an easy way of releasing the deployment wire from the delivering wire by pulling at one end of the deployment wire. Thus, the deployment wire can easily be removed from the occlusion device. The deployment tube houses the delivering wire and/or the deployment wire and optionally the retrieval wire.

The tail tube (12) can be moved into the direction of the head tube (10) to allow the tail tube (12) to be moved against the back side of the tissue over the delivering wire (14) during the deployment procedure by means of the second delivering means (not shown in the FIG. 7a) of the delivering system used.

The delivering rod (21) as the first delivering means, the optional deployment wire (22) and the optional retrieval wire (23), all of which are means of the delivering system and not of the occlusion device, can be removed through the catheter. They are shown in the embodiment of FIG. 7a and can easily be drawn out of the sheath (not shown) because they are removably connected to the head tube, the delivering wire as engaging means and the foldable tail portion of the occlusion device, respectively.

Working Example 3

In this embodiment, the occlusion device has the same structure as described in Working Example 2, except that the occlusion device has, as the engaging means, a delivering wire (14) which is not in a loop form, but extends over the tail tube (12) and goes through the sheath. In such a case, a deployment wire is not necessary.

After the occlusion device has been brought into the correct position and has been folded into the working structure, the delivering wire can be cut with a cutter. However, in this alternative embodiment, a separate cutter has to be introduced into the sheath. Such a cutting means is not necessary when working with two crossing wires which are both in a loop form as described in the Working Example 2, because the deployment wire (22) can then easily be drawn out by pulling at one end, while the delivering wire (14) can remain as the engaging means in the body.

Working Example 4

In an alternative embodiment to the embodiment described in Working Example 2, the deployment wire of the delivering system may be removably connected to the delivering wire of the occlusion device by a specific knot which allows the removing of the deployment wire after a specific motion of the respective wires, for example.

Working Example 5

In an alternative embodiment to the embodiment described in Working Example 2, the occlusion device can be provided with a good visibility in fluoroscopy for example. For providing at least partly radiopacity, two small waist marker films can be pasted onto the waist portion (16) of the foldable section of the occlusion device (please see FIG. 7a). Thereby, the strength or rigidity of the waist portion of the foldable section can be increased and radiopacity can be provided to the occlusion device.

Alternatively, also the other portions of the films could be made of a material comprising a radiopacifier to make the device visible during the deployment procedure.

Working Example 6

When preparing the head tube of the occlusion device according to the first aspect by dip coating (cf. FIG. 6), the mandrel can have the same diameter as the delivering rod used in the deployment procedure as first delivering means. Thereby the inner diameter of the head tube can be adjusted such that a slip fit connection of the delivering rod to the head tube is provided. The diameter of the mandrel used for preparing the tail tube can generally be a little bit larger than the diameter of the head tube because the inner diameter needs to be adjusted such that the delivering rod, the delivering wire and optionally the deployment wire can freely be passed through the hollow tube without blocking.

Example 1

1) Fabrication of Films

Figure 11:
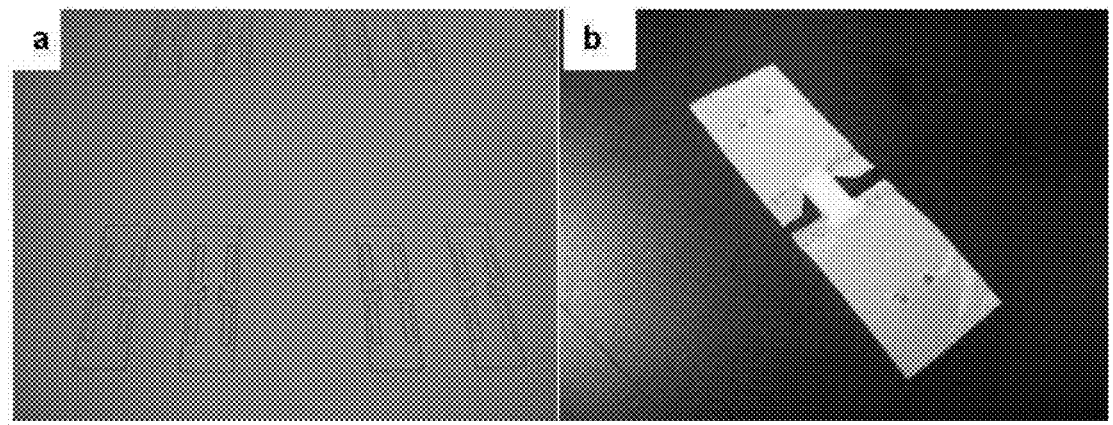
FIGS. 11a and b show the fabrication process of the films of the foldable section of an embodiment of the occlusion device of the present invention: (a) Film cutting template and (b) welded films.

Rectangular films (4% BaSO$_4$, 50 mm long, 12 mm wide, 200 μm thick) were placed on a template to cut out the intricate design as shown in FIG. 11a. The rectangles in the template mark the welding points. Two cutted films were ultrasonically welded. Two small marker films with 40% BaSO$_4$ (5 mm×5 mm×200 μm) were welded to the waist location to strengthen the structure and provide visibility under fluoroscopy (FIG. 11b).

2) Incorporation of Tubes

Figure 12:
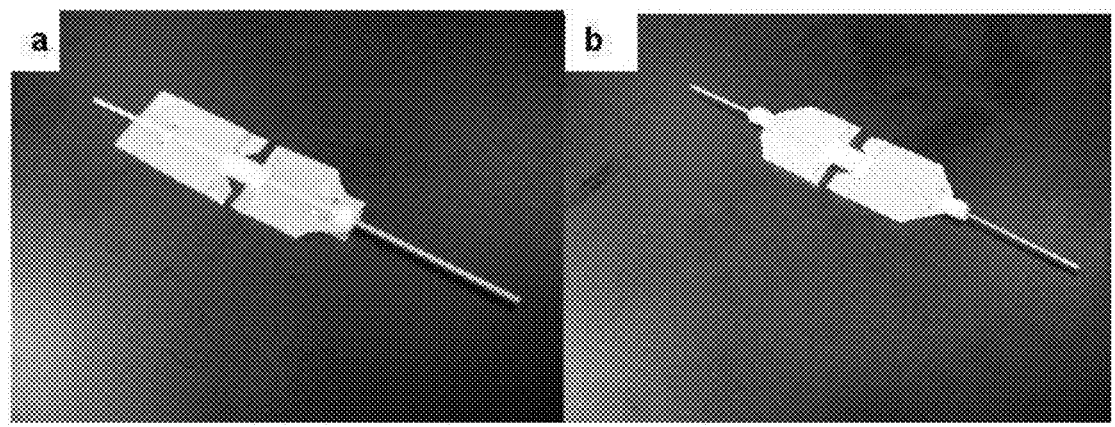
FIGS. 12a and b show further steps of the fabrication process of the embodiment of the occlusion device shown in FIGS. 11a and b: (a) The tail tube is welded onto the films and (b) the head tube is welded to the films.

The tail tube was first welded between the back ends of the films (8a). After welding, the excess films were cut for easy-folding as shown in FIG. 12a. Then a similar procedure was performed for the head tube (FIG. 12b).

3) Suturing of Device

Figure 13:
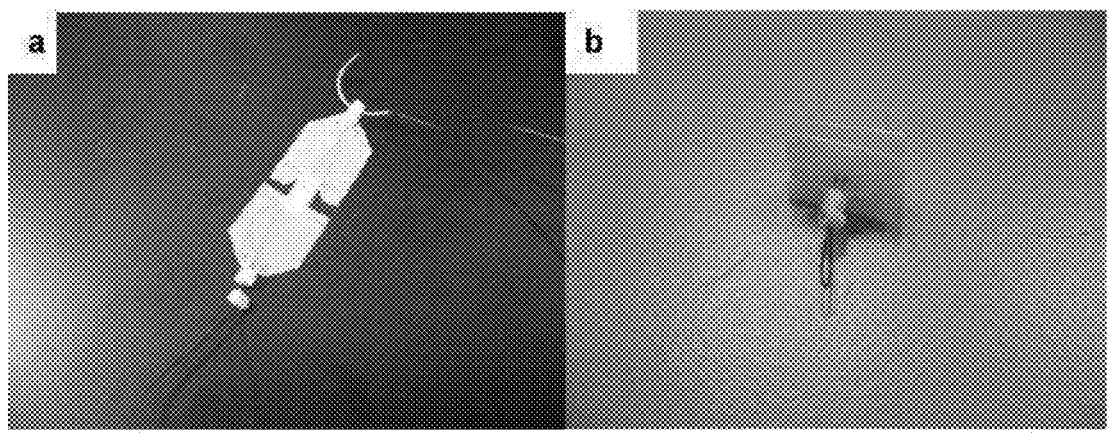
FIGS. 13a and b show the next steps of the fabrication process of the embodiment of the occlusion device shown in FIGS. 13a & b: (a) Suture (3-0) went through the tubes, films and lock tube; (b) shows the back view of the folded device structure.

Into the delivering wire (3-0 suture) was tied a knot. Then the delivering wire went through the head tube and one film, exited out of the tail tube, then went through the lock tube. After that, the delivering wire went a reverse way through the lock tube, the tail tube and another film to form a loop (FIG. 13a). It was tied a knot on the other side of the head tube.

The finished device was then folded into the working structure for heat treatment as shown in FIG. 13b.

4) Heat Treatment of Device

Figure 14:
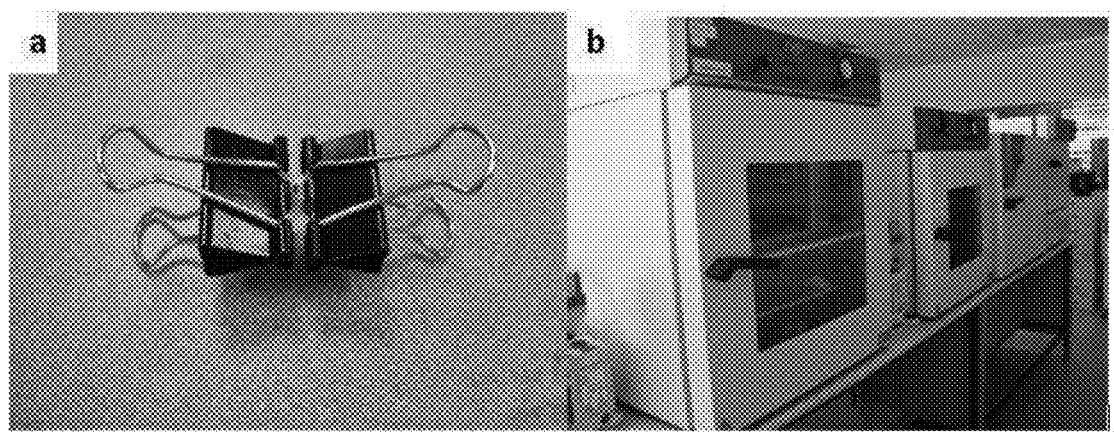
FIGS. 14a and b show the final steps of the fabrication process of an occlusion device according to an embodiment of the occlusion device shown in FIGS. 14 a and b: (a) The device films were compressed by two clips and (b) vacuum oven for a heat treatment of the fixed device.

The heat treatment was applied to the folded device to release stress and record a "shape memory" effect for the folded/working structure. The flaps of the device were pressed with 2 clips (FIG. 14a). A Teflon paper was inserted between contact of device and clip to ensure cleanness. Heat treatment was done in a vacuum oven at 55° C. for 24 hours (FIG. 14b). Then the device was able to fold easily into the correct position once the occlusion device was deployed out of the sheath.

The heat treated occlusion device was then prepared for being provided with the delivering system to prepare a kit of the occlusion device and the delivering system which will generally be distributed as one unit.

Example 2

Figure 15:
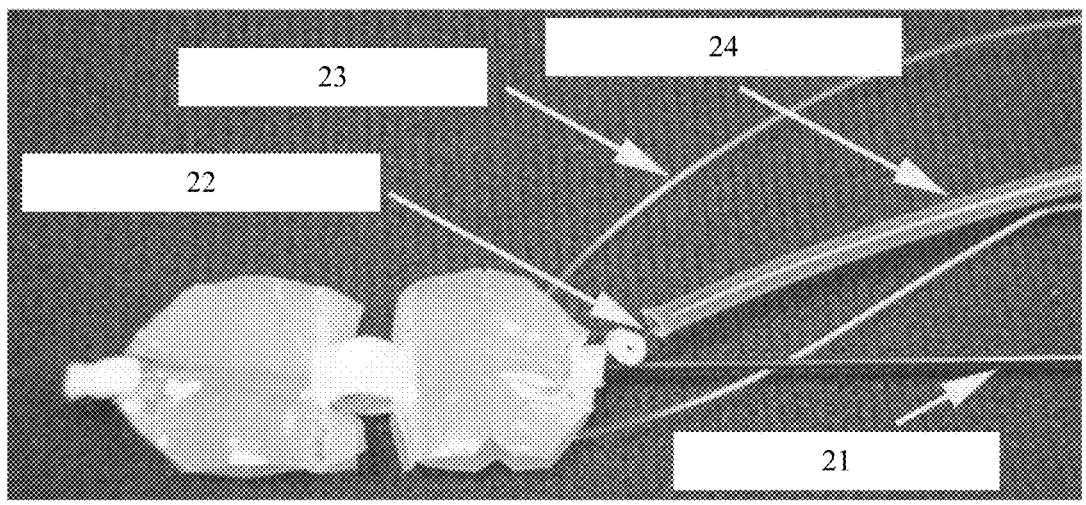
FIG. 15 shows one embodiment of a delivering system for an occluder described herein.

The delivering system consisting of a sheath (not shown), delivering rod (21), deployment tube (24) and retrieving wire (23) were attached to the occlusion device prepared in Example 1 as shown in the FIG. 7a and in FIG. 15. The delivering rod was a stainless wire of ⌀0.65 mm. The retrieving wire was a bio-degradable suture (PDS II 2/0) of ⌀0.36 mm. The deployment tube was a PTFE tube of ⌀1.65 mm with the deployment wire and the retrieval wire going through.

The delivering system was connected to the occlusion device prepared in Example 1 such that the kit of the present invention was prepared. Using the kit comprising an occlusion device and the delivering system of the present invention, the occlusion device can be retrieved completely when the device was not deployed in the correct position.

Example 3

Ethylene oxide (ETO) sterilization of the devices and associated surgical tools was done at Tan Tock Seng Hospital, Singapore. Devices and relevant delivering systems were sealed in the form of the kit of the present invention comprising the occluder and the delivering system in a standard ETO sterilization pouch. The sterilization procedure was conducted at 37° C. for six hours followed by purging of the ETO gas for another continuous 16 hours.

Post-sterilization cell culture conducted both in house and at a contract research lab shows that the procedure complies with relevant standards.

Example 4

In Vitro Testing and Degradation

In Vitro Degradation

Polycaprolactone (PCL Mw 80,000, Aldrich) and PLA-PCL copolymer (IV 1.62, Purac) were studied in vitro for their degradation behavior. Four configurations of films were tested: Pure PCL (200 μm thick); pure copolymer (200 μm thick); PCL with 30% BaSO$_4$ (200 μm thick) and copolymer with 30% BaSO$_4$ (200 μm thick). Films were prepared by solution casting and all films were tested on a thermogravimetric analyser (TGA) to ensure that the solvent content was less than 1% (w/w) before the in vitro tests. Then, 1×1 cm casted films are immersed in phosphate buffer solution (PBS) and stored in an incubator at 37° C. for 12 weeks. Sampling was conducted in duplicate at different time intervals: week 0, week 1, week 4, week 8, and week 12.

Scanning Electron Microscope (SEM) Examination

Figure 16:
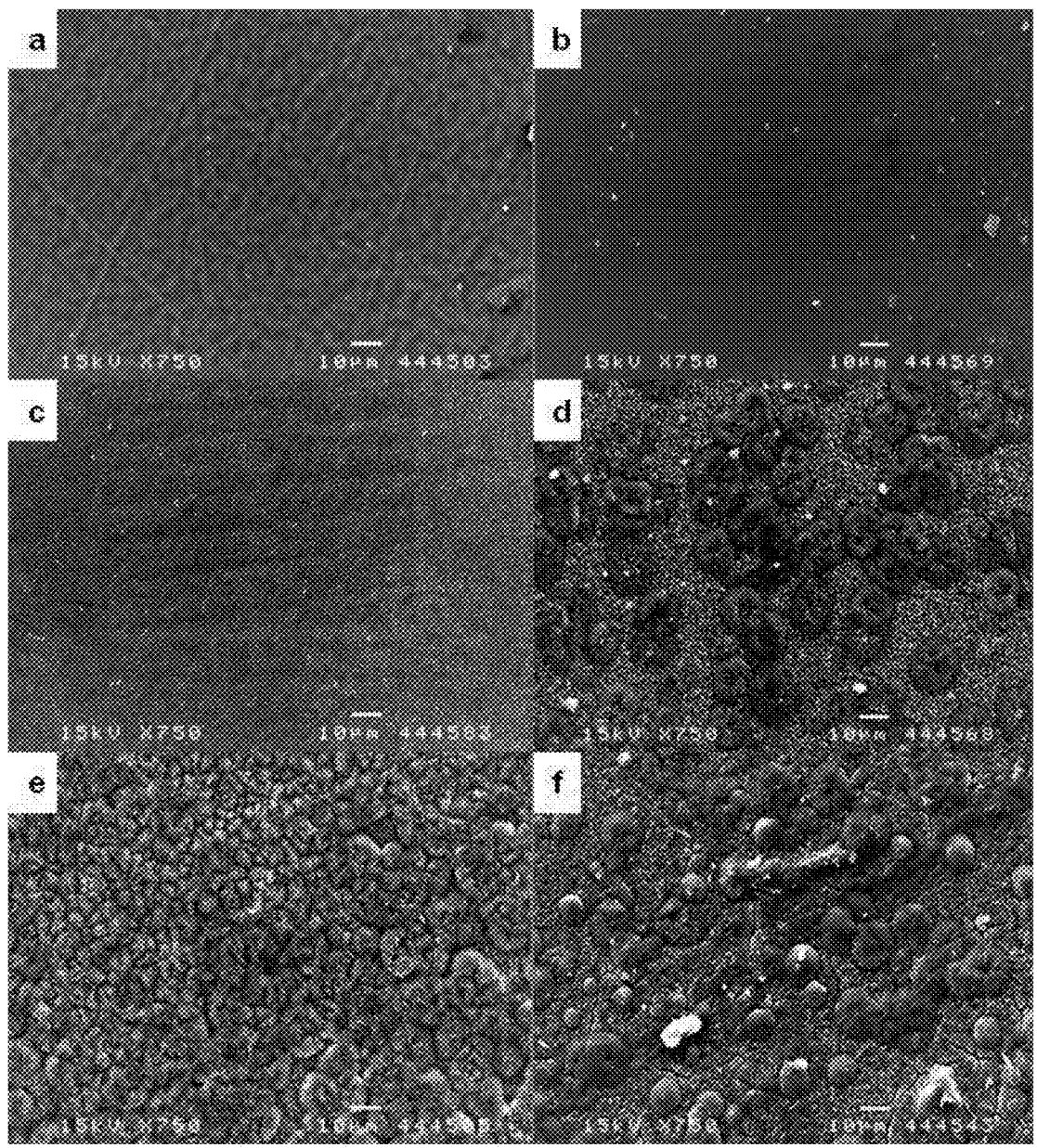
FIGS. 16a-f show the degradation of pure copolymer: (a) original; (b) 0 week; (c) 1 week; (d) 4 weeks; (e) 8 weeks; (f) 12 weeks (the scale bar is 10 µm).

FIGS. 16a-f show the degradation of pure copolymer. The original copolymer is shown in FIG. 16a. Even after 1 day of immersion, the film surface became smooth (FIG. 16b). After one week, the film was rough again (FIG. 16c). From then on, there occurred many large hilly lumps on the film surface (FIG. 16d) and the lumps were reduced and increased with degradation (FIG. 16e). After 12 weeks, the large lumps occurred again and between them many cracks can be seen (FIG. 16f).

Figure 17:
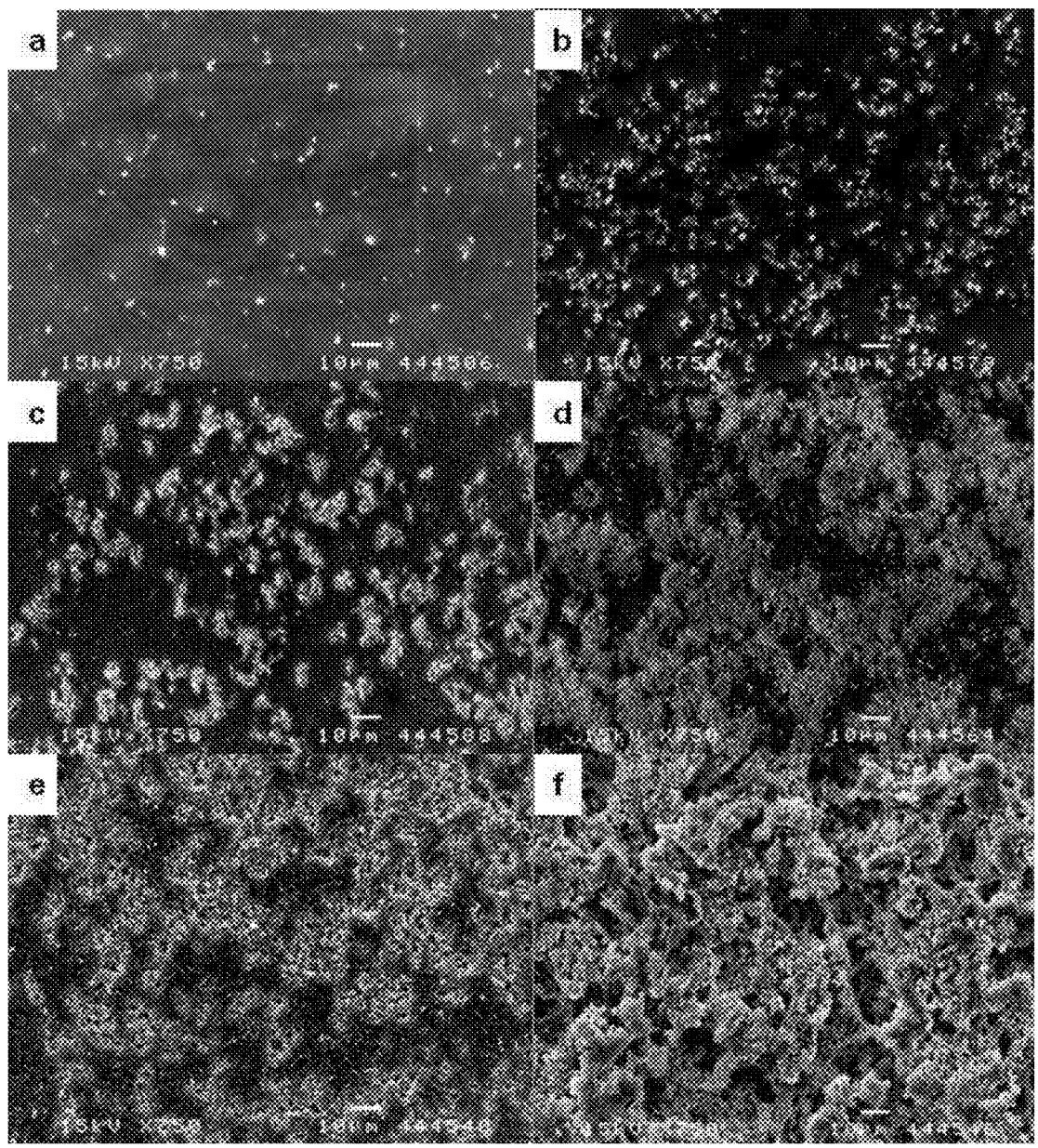
FIGS. 17a-f show the degradation of copolymer+30% $BaSO_4$: (a) original; (b) 0 week; (c) 1 week; (d) 4 weeks; (e) 8 weeks; (f) 12 weeks (the scale bar is 10 µm).

FIGS. 17a-f show the degradation of copolymer+30% BaSO$_4$. The BaSO$_4$ particles can be clearly seen on the surface of the original film (FIG. 17a). During one week of degradation, the BaSO$_4$ particles were more and more segregated on the surface (FIGS. 17b & c) when the copolymer degraded. Then the particles began to leave the polymer surface, leaving many holes on the film surface (FIG. 17d). Newer BaSO$_4$ particles then appeared on the surface when the degradation continued (FIG. 17e). After 12 weeks, the surface was filled with deep holes (FIG. 17f).

Figure 18:
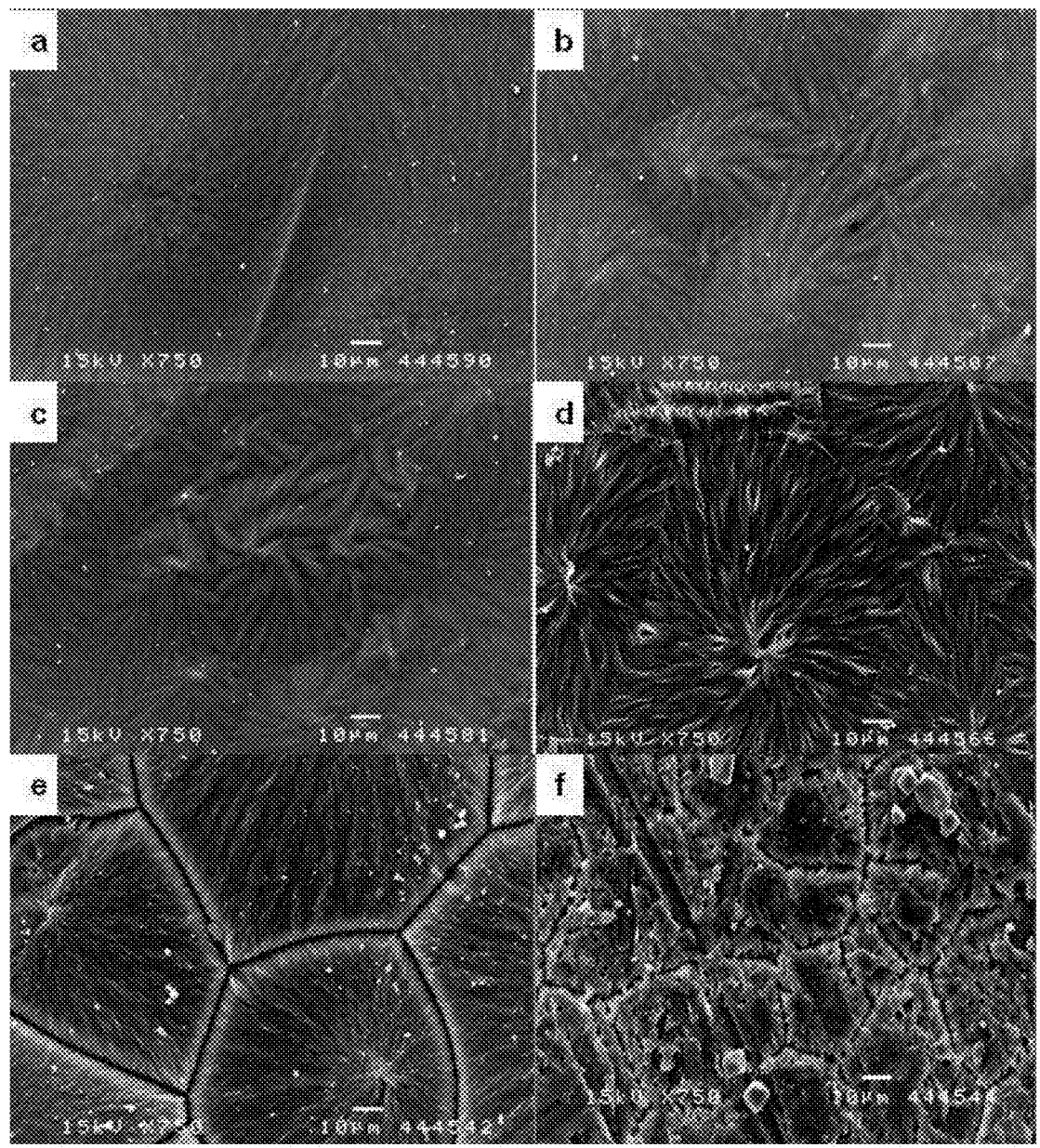
FIGS. 18a-f show the degradation of PCL: (a) original; (b) 0 week; (c) 1 week; (d) 4 weeks; (e) 8 weeks; (f) 12 weeks (the scale bar is 10 µm).

FIGS. 18a-f show the degradation of pure PCL. The film surface remained almost intact for one week. Figures a-c show the surface in the original state, after 0 week and after 1 week. After 4 weeks the surface was composed of large chrysanthemum-like "cells" with clear margins between them (FIG. 18d). The margins became deep and widen with degradation and the cells were separated from each other like the classic crystal structure (FIG. 18e). At 12 weeks, the large cells disappeared and were divided into many smaller cells (FIG. 18f).

Figure 19:
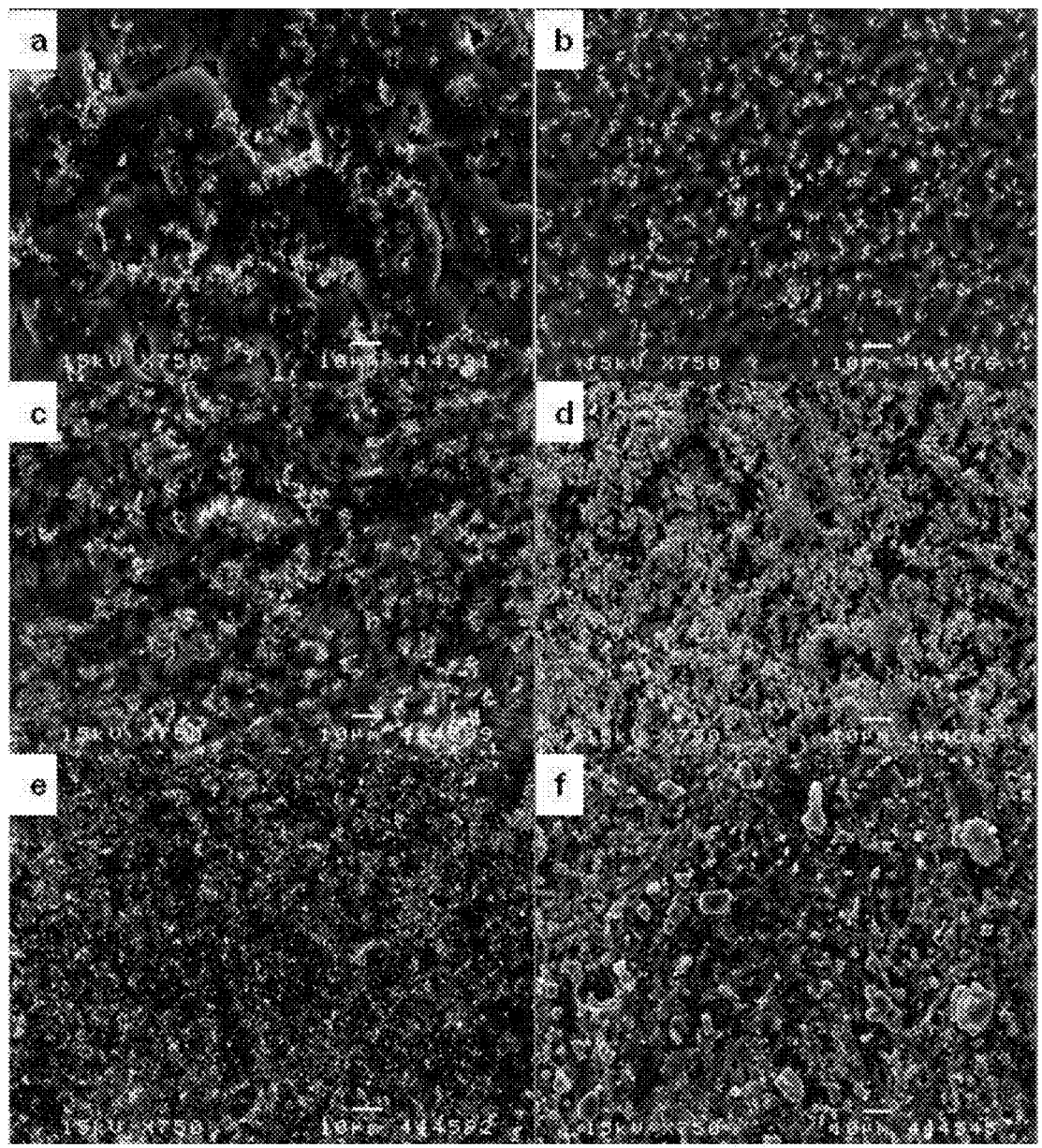
FIGS. 19a-f show the degradation of PCL+30% BaSO$_4$: (a) original; (b) 0 week; (c) 1 week; (d) 4 weeks; (e) 8 weeks; (f) 12 weeks (the scale bar is 10 μm).

FIGS. 19a-f show the degradation of PCL+30% BaSO$_4$. It can be seen that the BaSO$_4$ particles were more dispersed than in the copolymer matrix in the original state (FIG. 19a). The degradation process was similar to that of the copolymer+30% BaSO$_4$. The BaSO$_4$ particles became more and more segregated until they eluted out of the film, leaving many tiny pores on the surface. FIGS. 19b-d show the respective surface state after 0, 1 and 4 weeks. Then new BaSO$_4$ particles surfaced with degradation (FIG. 19e). After 12 weeks the film surface were filled with tiny holes but were not as deep as that on the copolymer matrix (FIG. 19f).

Molecular Weight Loss

The molecular weight (Mw) of each sample collected from time points was tested on gel permeation chromatography (GPC).

Figure 20:
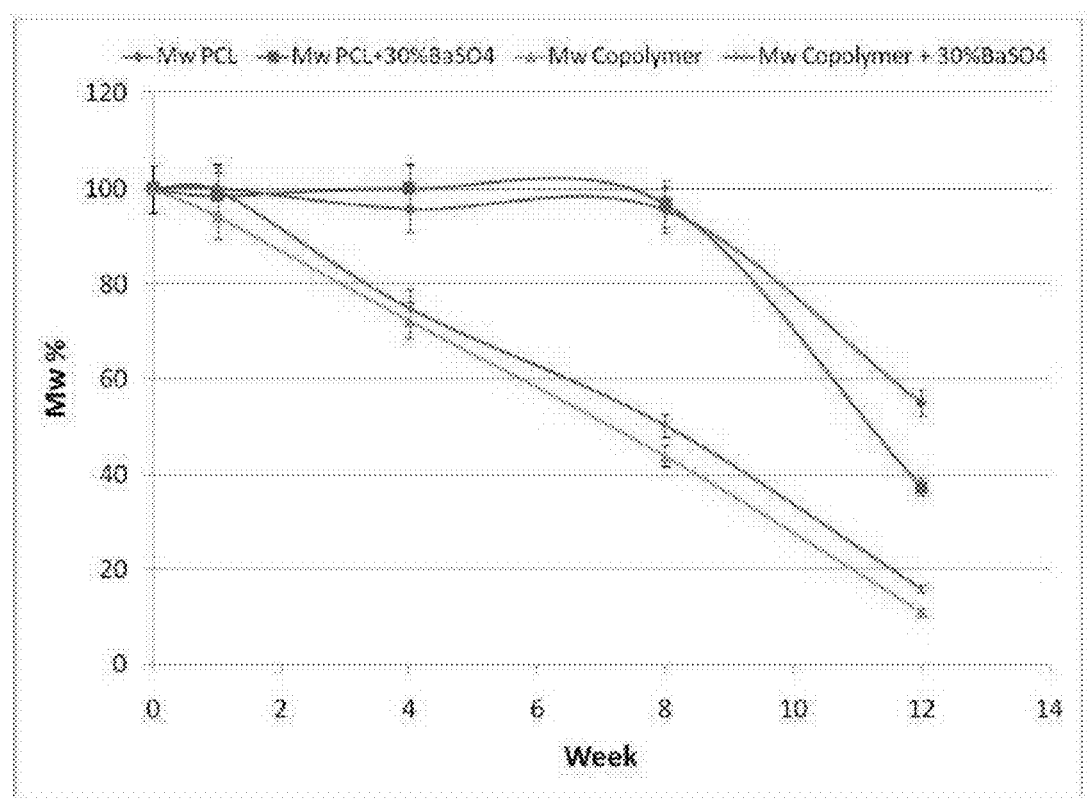
FIG. 20 shows the molecular weight (MW) loss during 12 weeks of degradation of some polymer candidates to be used in occlusion devices of the present invention.

Mw loss of four types of films was plotted in FIG. 20. Copolymer degrades generally faster than PCL as expected up to week 12. PCL starts to show rapid degradation after week 8, while copolymer displays steady chain shortening pattern from week 1 onwards. PCL starts to accelerate on degradation rate after week 8, while copolymer shows a linear Mw loss throughout 12 weeks. And BaSO$_4$, as the physical inclusion, does not seem to impact significantly on the degradation pattern of the polymers.

Mass Loss

The mass loss of films after each time point was measured after the samples were recovered from the PBS and freeze dried.

Figure 21:
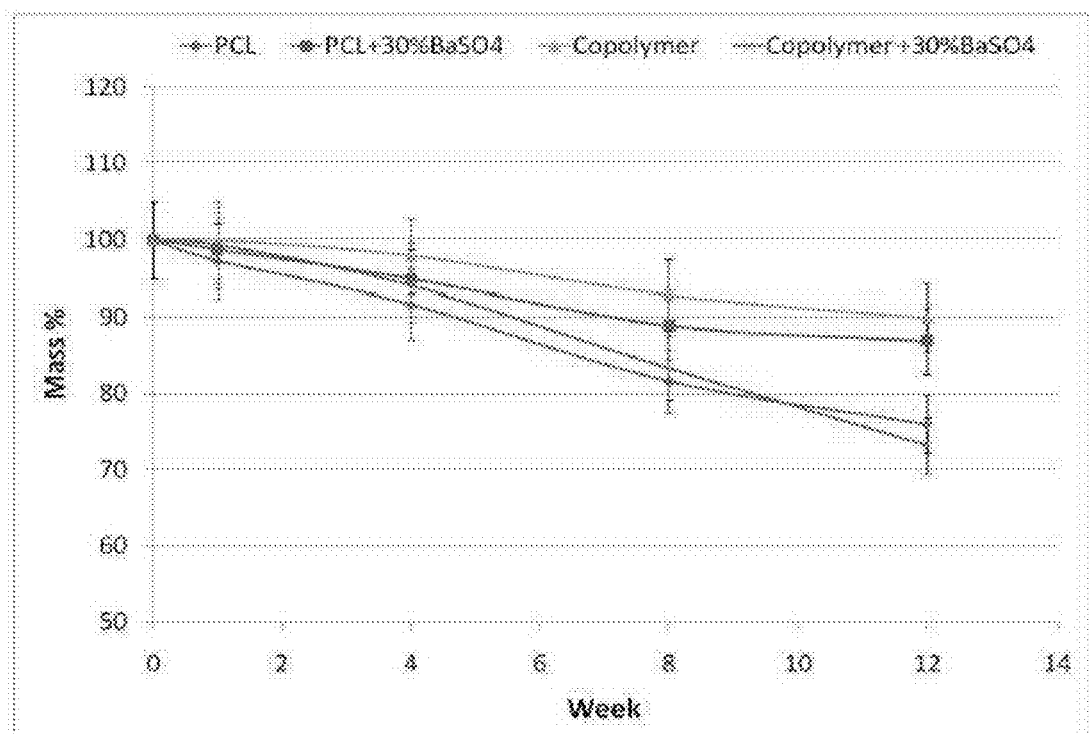
FIG. 21 shows the mass loss during 12 weeks of degradation of the polymer candidates used for the measurements of FIG. 20.

An increase in mass loss for the PCL films was observed as degradation continues. (FIG. 21). And copolymer films show a more steady and linear trend.

Modulus Change

DMA test for storage modulus change was also conducted at each time point at 37° C. All samples were immersed in deionized water for 20 min prior to loading on DMA. DMA runs were performed at Multi Frequency Strain mode from 25° C. to 100° C. for copolymer based films and 25° C. to 60° C. for PCL based films.

Figure 22:
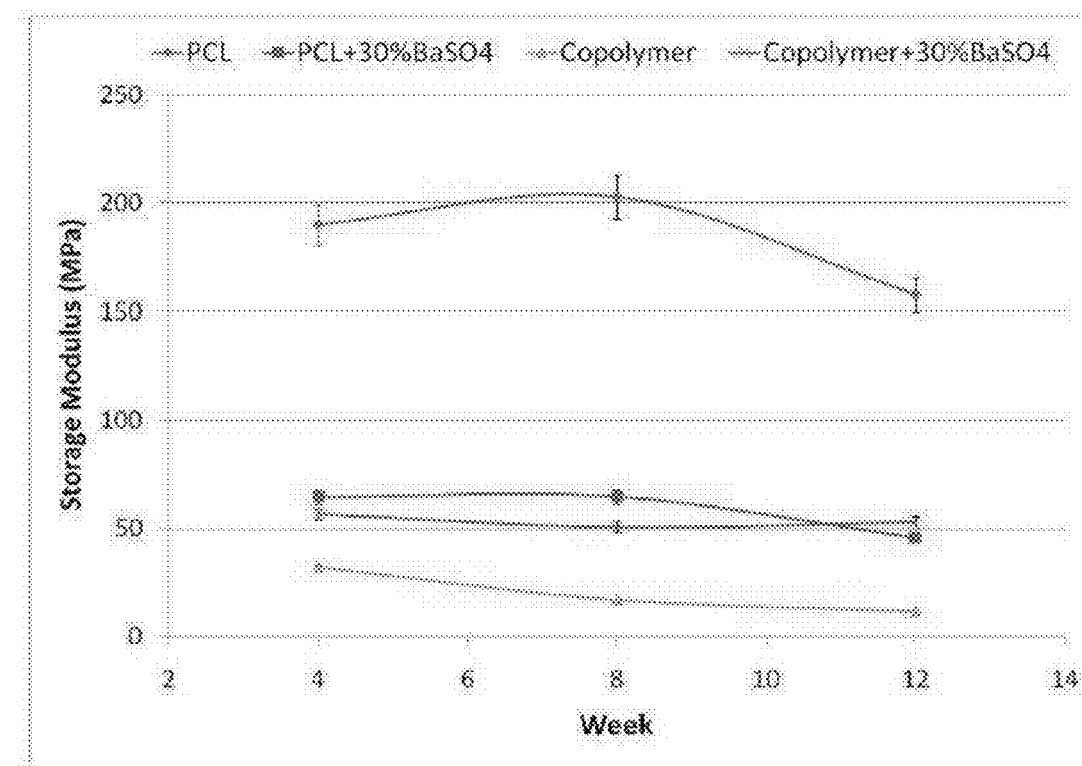
FIG. 22 shows the storage modulus variation at 37° C. during 12 weeks of degradation of the polymer candidates used for the measurements of FIG. 20.

The mechanical property is closely linked with the molecular weight of a (co)polymer. As degradation progresses, molecular weight loss should result in modulus loss of the polymers. However, modulus change surprisingly did not match the degree of molecular weight loss. This is shown in FIG. 22. Most likely, the molecular weight loss occurs in the amorphous region, and is not substantial enough to decrease modulus, which may be dominated by crystallinity for PCL; for the copolymer, some loss in modulus can be seen in FIG. 18. However, it did match with the in vivo results as after one-month implantation (swines have higher metabolism so comparable to three months in humans) the polymers retain good integrity and enough load bearing quality for its function.

Example 5

In Vitro Deployment Test

Figure 23:
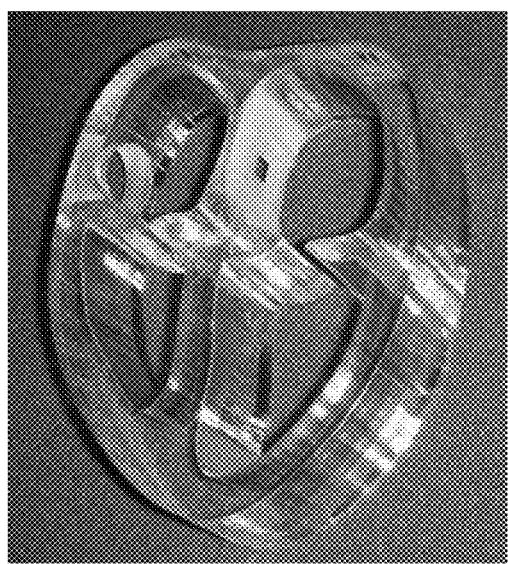
FIG. 23 shows an atrial septal defect/patent foramen ovale (ASD/PFO) model for in vitro deployment tests.

This test aims to verify the folding and sealing mechanism of the design based on a polycarbonate (PC) septal defect model which is shown in FIG. 23. The in vitro ASD/PFO model has two holes of Ø16 mm on the right atrium wall and atrial septum, respectively. The former provides access for the device to the right atrium; and the latter as the base for a thin copolymer film (200 μm) with a 5×5 mm window as the ASD/PFO model.

Figure 24:
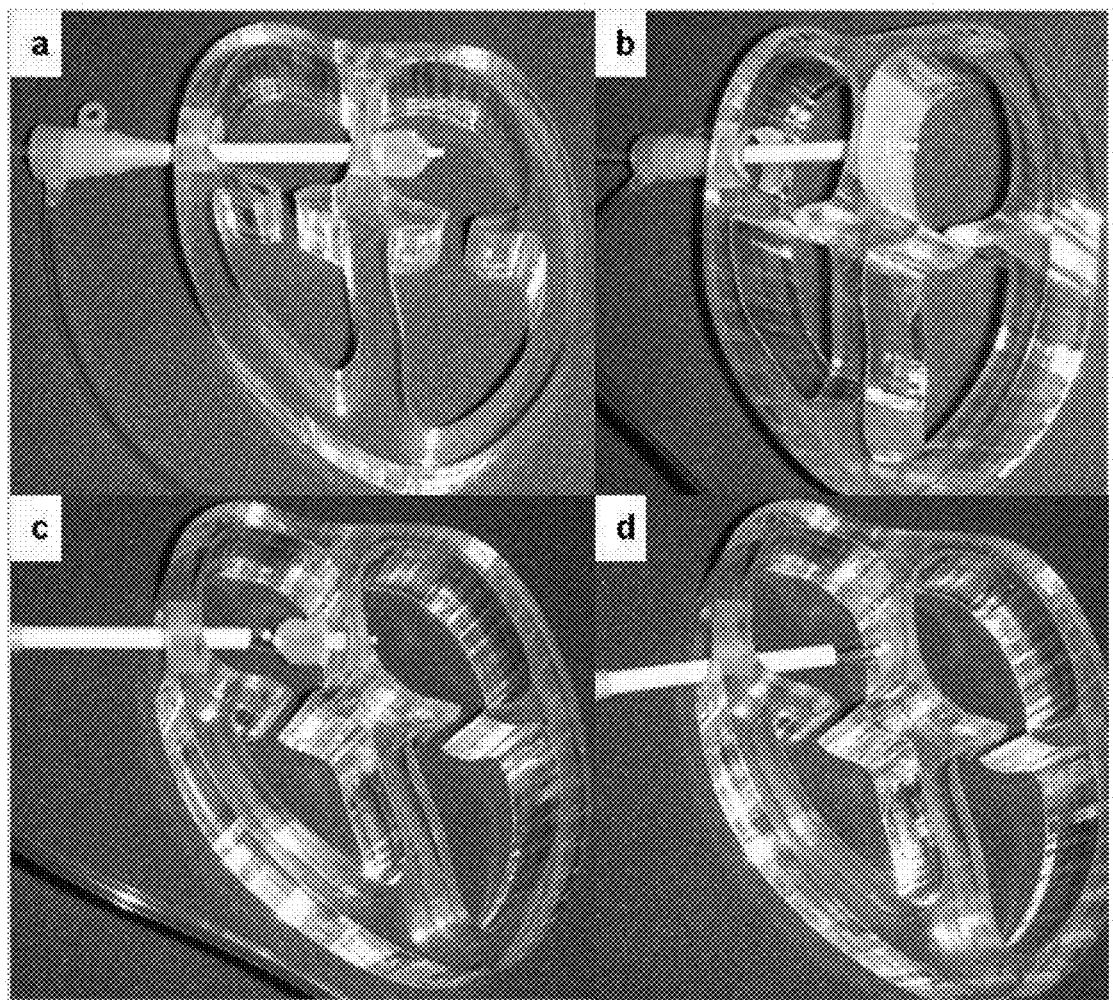
FIGS. 24a-d show several steps of the in vitro testing of an embodiment of the occlusion device deployment at the atrial septal defect/patent foramen ovale (ASD/PFO) model.

The occlusion device of the first aspect was first inserted into an 11F sheath, which went through the right atrial wall of the ASD/PFO model. Afterwards the front part of the compressed films was pushed out of the sheath and allowed to unfold in the left atrium (FIG. 24a). The flattened films were then folded by pulling back the deployment wire and sat against the septum model (FIG. 24b). The remaining part of the device was also released from the sheath and unfolded in the right atrium (FIG. 24c), which could be folded again and sealed against the other side of the septum model by pushing the deployment tube and holding the deployment wire (FIG. 24d). The occluder design shows easy foldability and satisfactory recovery speed. The pull-and-fold mechanism works effectively.

Figure 25:
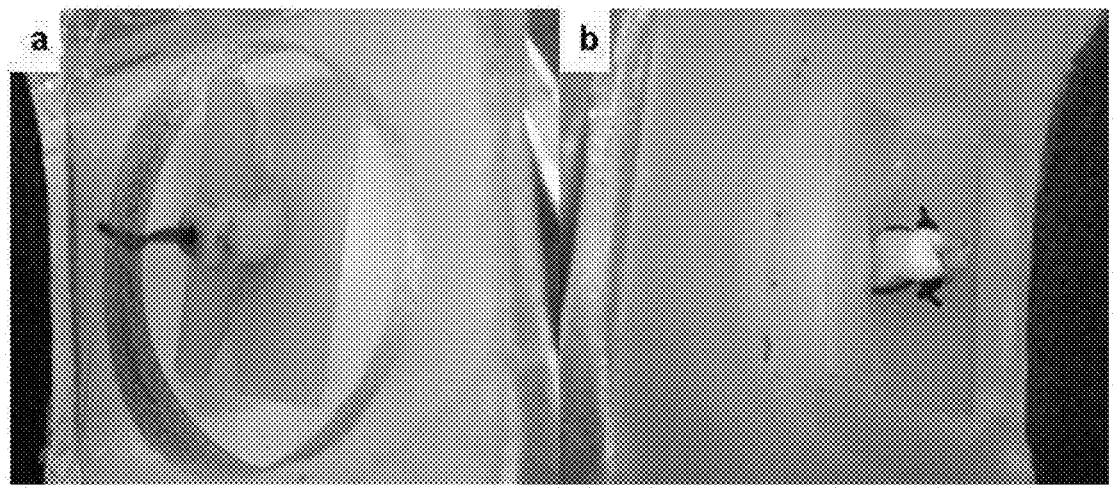
FIG. 25a shows a photo of an embodiment of an occluder in the working structure at the right atrium side in the in vitro testing and FIG. 25b shows a photo of the occluder in the working structure at the left atrium side in the in vitro testing.

After the delivering system retrieval, the device positioned well at the defect location as shown in FIGS. 25a and b. The photo (FIGS. 25a and b) shows a good sealing result from the right left atrium side as well as from the left atrium side.

Radiopacity Test

X-ray visibility of the occluder of the first aspect was tested on a fluoroscope (GE, Innova) at National University Hospital, Singapore. A standard acrylic plate (8 mm thickness) plus a slice of pork (with skin and fat on, about 5 cm thick) were used as the phantom on top of the PC ASD/PFO model. A normal examination procedure was performed and X-ray videos/images were taken.

The occluder show remarkable radiopacity even when being covered by two layers of phantom and inside the sheath. Clear device profiles have been captured under the X-ray, owing to high loadings of $BaSO_4$ (40%) at the occluder's tip (head tube), waist and lock tube. Good X-ray visibility ensures good maneuverability during deployment.

Figure 26:
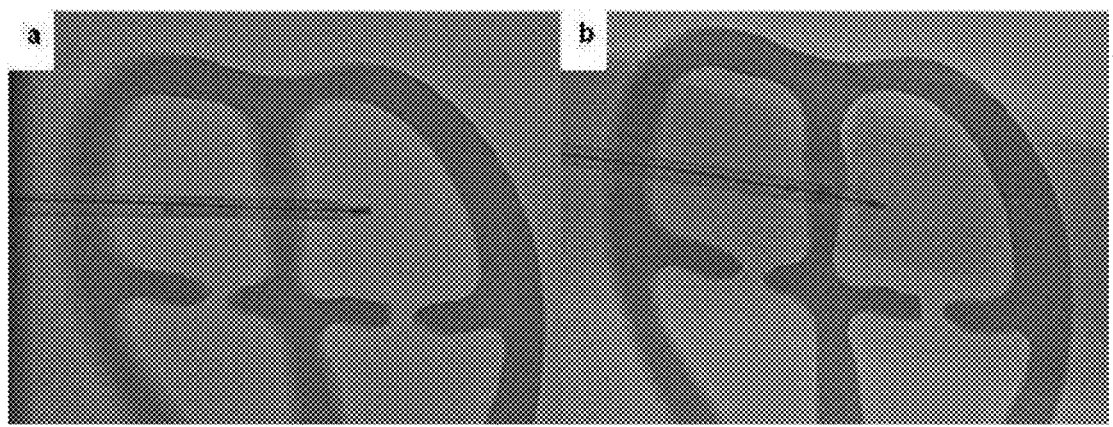
FIGS. 26a and b show. X-ray images of an embodiment of an occluder of the present invention in sheath (FIG. 26a) and partly unfolded (FIG. 26b).

FIG. 26 shows the X-ray images of the occluder device of the first aspect. In FIG. 26*a* the occluder is in the sheath which is already placed in the hole of the model. FIG. 26*b* shows the occluder which is partly deployed in the left atrium during the step of folding the foldable head portion of the occluder, thereby closing the opening from the left atrium side.

Example 6

In Vivo Tests

Animal Selection

The animals selected were male Yorkshire swines, approximately 50-60 kg weight, because of the similar heart size to humans. The animals were from Innoheart Pte Ltd, a pre-clinical contract research organization in Singapore. The study protocol was approved by the IACUC of Innoheart Pte Ltd. Three similar occluders according to the first aspect of the application were tested, namely "CL1", "CL2", "CL3". CL stands for Chinese Lantern design occluder because the folded structure looks similar to such a Chinese Lantern. However, the swine with "CL1" died due to puncture of aorta during creation of the ASD/PFO model.

Creation of ASD/PFO Model

Pre-Medication Administration

The animals were kept for at least two days before the procedure at the facility and pre-medicated with Aspirin (400 mg) 3 days prior to surgery. They were also fasted overnight from 6 pm one day before surgery.

Surgical Preparation

The animals were sedated with 0.5 mg/kg IM TKX cocktail. After sedation, they were brought to the animal preparation room where an IV drip line was inserted into one ear vein and they were then intubated. The surgical site was shaved with electrical shaver and was cleaned with wet gauze and hibiscrub. The animals were placed on the ventilator throughout the duration of the surgery.

Surgical Procedure

Antibiotics (Ampicillin 10 mg/kg) was administered IM at the start of the procedure. ECG, heart rate, respiratory rate, transcutaneous oxygen saturation, tidal volume, and end-tidal $CO_2$ were monitored throughout the procedure. For cardiac catheterization of femoral artery, the femoral artery was exposed through an incision made on the inner thigh. The muscle layers were carefully separated until the femoral artery was exposed. The distal portion of the artery was ligated and a 7F sheath was inserted into the vessel. A proximal ligature was made to secure the sheath. The sheath advanced into the aorta, following which a bolus of heparin were injected.

For atrial access, the second and third ribs were identified and an incision was made. The right atrium of the heart (30) was exposed. A purse-string suture (31) was made before atrial puncture to secure hemostasis after insertion of an 11F sheath (32) as shown in FIG. 27.

Figure 27:
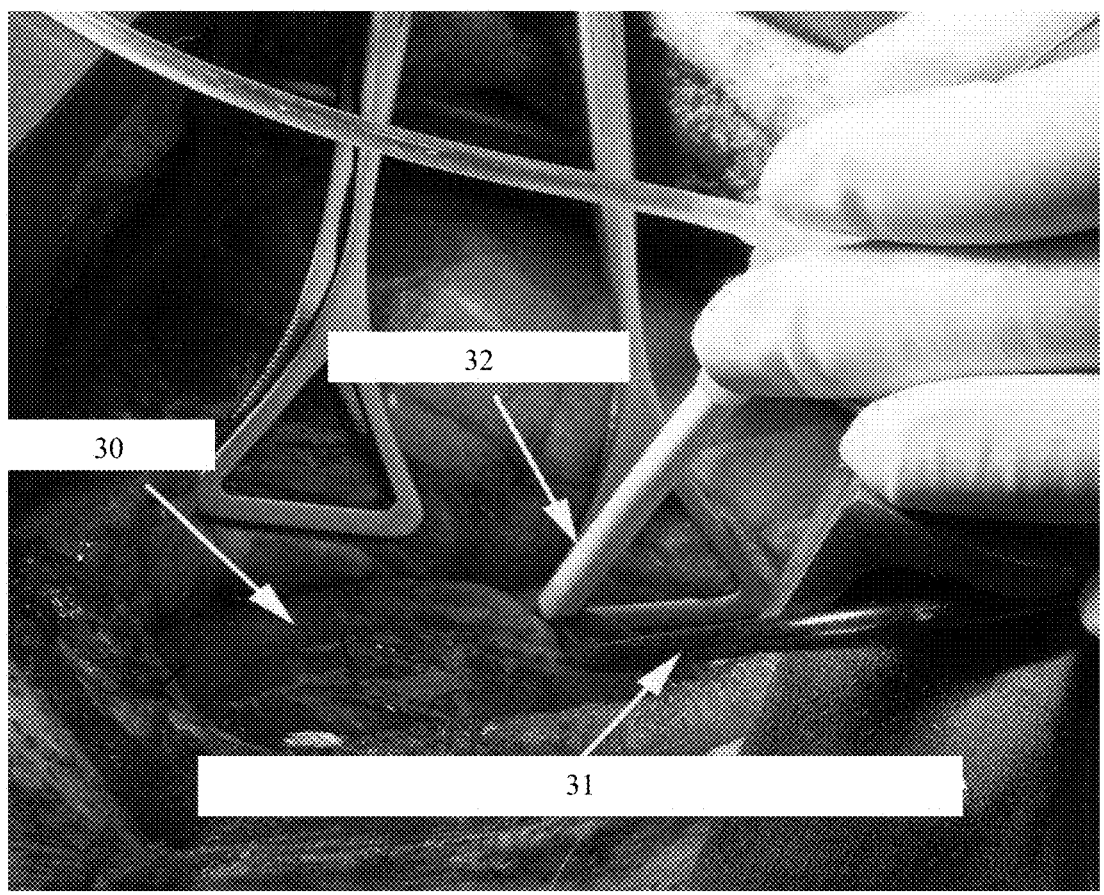
FIG. 27 shows a photo of a puncture of the right atrial wall of an animal during surgery.

The right atrium wall was punctured by a dilator of an 11F sheath, followed by the sheath (32) as shown in FIG. 27. After the sheath went into the right atrium, contrast media was injected to confirm the location of atrial septum, which was then punctured by a long puncture needle. The needle was moved forward careful to avoid free wall puncture and/or aortic puncture. The dilator of the 11F sheath was then gently advanced, after which the needle was removed and a guide wire was introduced into the left atrium. The PFO model was then created by pushing the 11F sheath across the septum, therefore estimated size of PFO was about 4.0 mm. After confirmation of the PFO model on fluoroscopy (FIG. 28), the guidewire and dilator were retrieved, leaving the 11F sheath at the location of created PFO for the occluder deployment.

Operational Procedure and Results

Device Preloading

Figure 29:
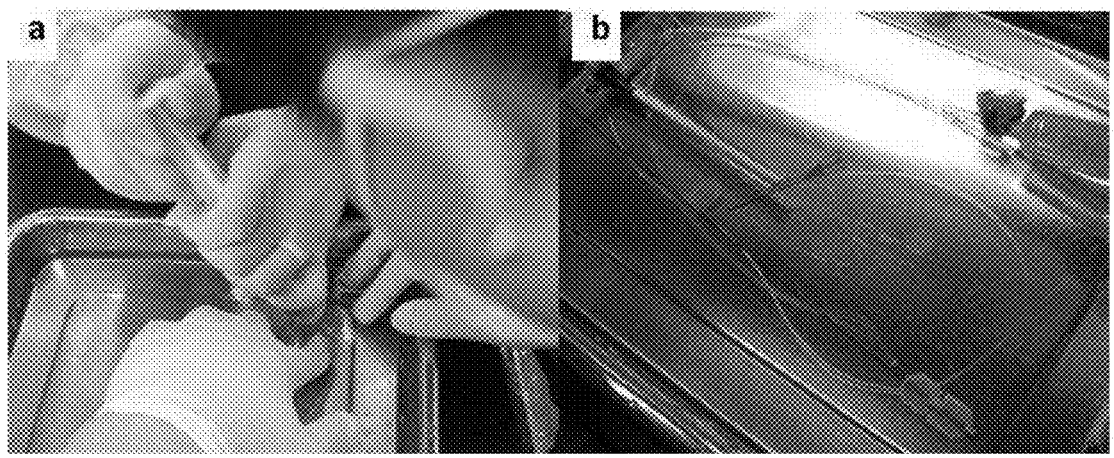

The occlusion device and delivering system were taken out of the sterilized package (FIG. 29*a*) and immersed in saline solution. After checking the structure integrity of the device, the surfaces of the films and tubes were flushed continuously using a syringe in the saline to ensure the bubbles attached were completely removed. The 9F sheath and introducer were also flushed in the saline as well. FIG. 29*b* shows the debubbling procedure.

Figure 30:
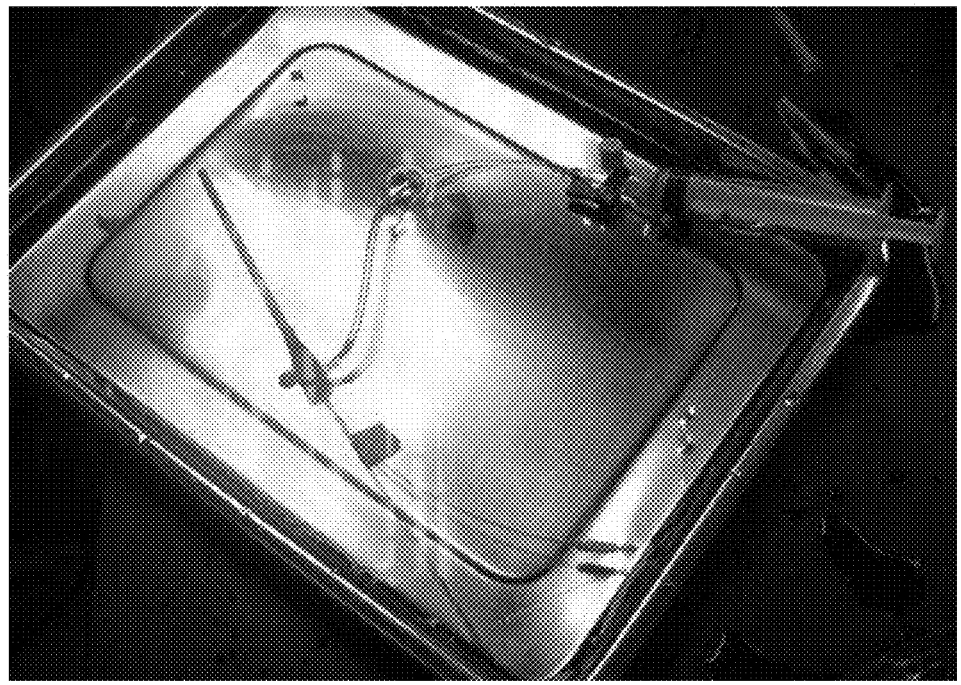
FIG. 30 shows a photo of the preloaded device.

After debubbling, the device was pushed gently into the 9F sheath using the delivering wire through the introducer, and then the delivering wire was kept moving until the head tube reached the distal end of the 9F sheath (FIG. 30). The sheath and device in it were flushed again using the syringe. During preloading, the films were squeezed in to conform to the space of the sheath.

Device Deployment

Figure 28:
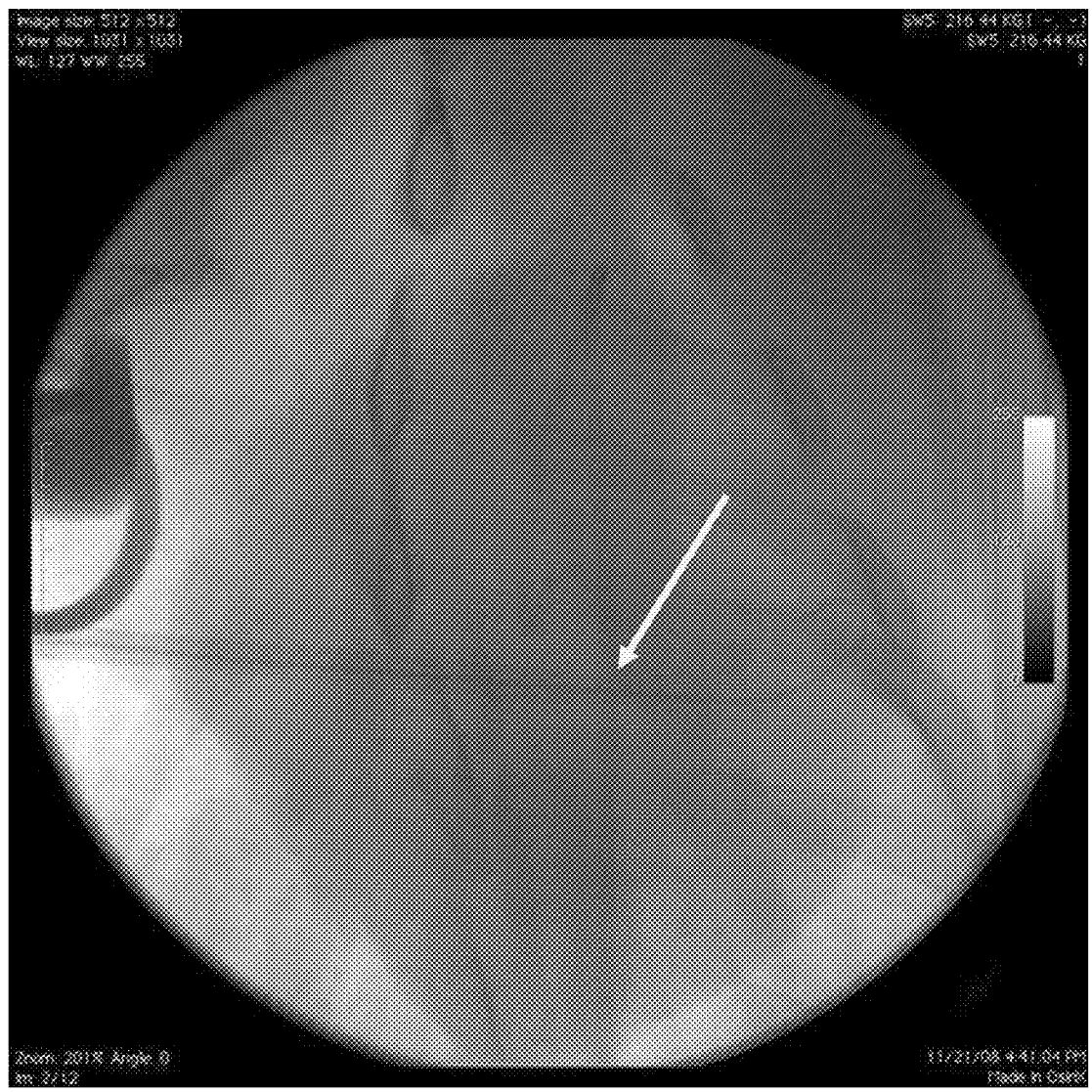
FIG. 28 shows a fluoroscopy picture of the guidewire, dilator and the 11F sheath across the septum (please see arrow). It means that the model of PFO was successfully created. After retrieving the guidewire and dilator, the occlusion device can be deployed through the 11F sheath.

The 9F sheath was taken out of the saline solution (with the occlusion device inside) and inserted directly into the 11F sheath which had been positioned previously across the ASD/PFO model which is shown in FIG. 28. The device was pushed into the 11F sheath from the 9F sheath and then the 9F sheath was removed.

Figure 31:
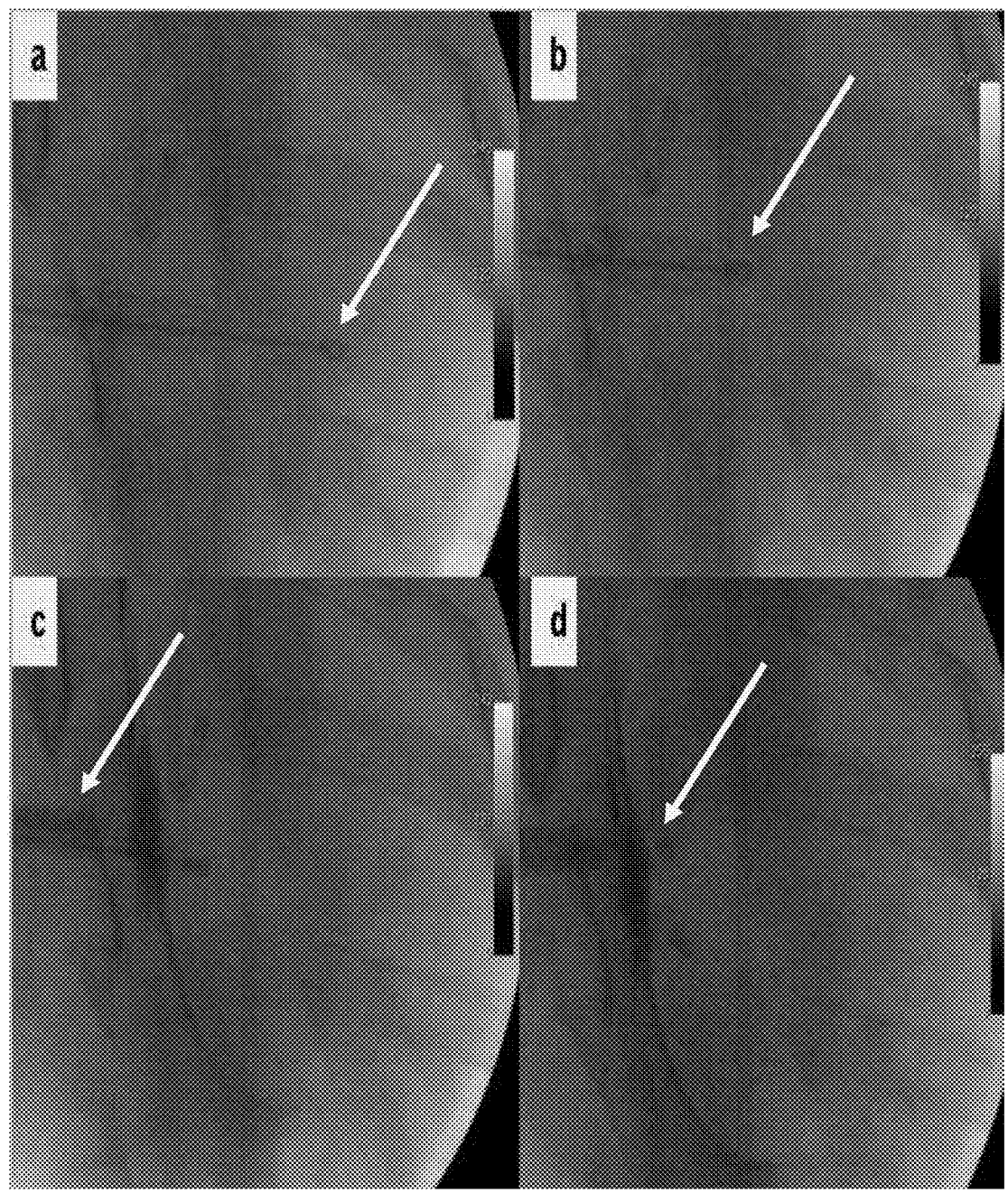
FIGS. 31a-d show fluoroscopy pictures of the deployment procedure of an embodiment of an occlusion device described herein: (a) Firstly, the anterior portion of the occlusion device (please see arrow) was pushed out of the 11F sheath and located in the left atrium; (b) secondly, the anterior portion was folded and anchored to the left atrium wall (please see arrow); (c) the 11F sheath (please see arrow) was pulled back to release the posterior portion of the occlusion device and it was then folded; (d) The deployment was succeeded and, thus, the 11F sheath and all of the delivery apparatus were retrieved back. The deployment was completed and the deployed and folded occlusion device (please see arrow) was anchored to the septal defect.

Under the fluoroscopic guidance, the device was pushed forward in the 11F sheath until the head tube and the foldable head portion of the occluder was out of the sheath and in the left atrium. The position of the front part was confirmed by the radiopaque marker on the film waist (FIG. 31*a*). Deployment was paused for 5 seconds, allowing the film to recover to its unfolded shape by means of the shape memory function of the films. Thereafter, the films of the foldable head portion (LA films) were folded again to their working structure (the first half of the Lantern) by withdrawing the delivering wire (FIG. 31*b*).

The device was then anchored against the atrial septum by withdrawing the delivering wire and pulling the sheath at the same time, which can be felt manually and also observed under fluoroscopy (injecting contrast medium). With tension on the delivering wire, the sheath was pulled back and the foldable head portion together with the head tube was released in the right atrium. After 5 seconds of film recovery time for complete deployment by means of the shape memory function of the films, the tail and the lock tubes were advanced by pushing the deployment tube, thereby folding the films of the foldable tail portion into the working structure. The lock tube was advanced until maximum resistance was felt, which indicated that the films were folded to their maximum and "clipped" the PFO firmly. A gentle "to and fro" motion with the delivering wire assured a secure position across the PFO model, which was also displayed under fluoroscopy (FIG. 31*c*).

If the device placement was unsatisfactory, the device could be retrieved by performing the following steps: Hold the retrieving wire, and then push the delivering rod to unfold the films. Push the sheath forward (with holding the retrieving wire) to retrieve a part or all the films into the sheath and redeploy or replace with a new device.

When the deployment was satisfactory, the delivering system was withdrawn in the following sequence: retrieval wire first, followed by delivering rod, deployment wire and lastly deployment tube. The final fluoroscopic test is shown in FIG. 31d with no shunting across the septum.

After the device deployment, the animals were allowed to recover as per protocol. Painkiller (Ketorolac 1 mg/kg) was administered IM. For the three animals, the first one ("CL1") died during PFO model creation because of the puncture of aorta. The deployment for the other two ("CL2" and "CL3") were successful. For "CL2", the 11F sheath had once gone too deep into the left atrium where the entire device had been released, so a retrieval and redeployment procedure was performed smoothly and successfully.

One Month Follow-Up and Sacrifice

Figure 32:
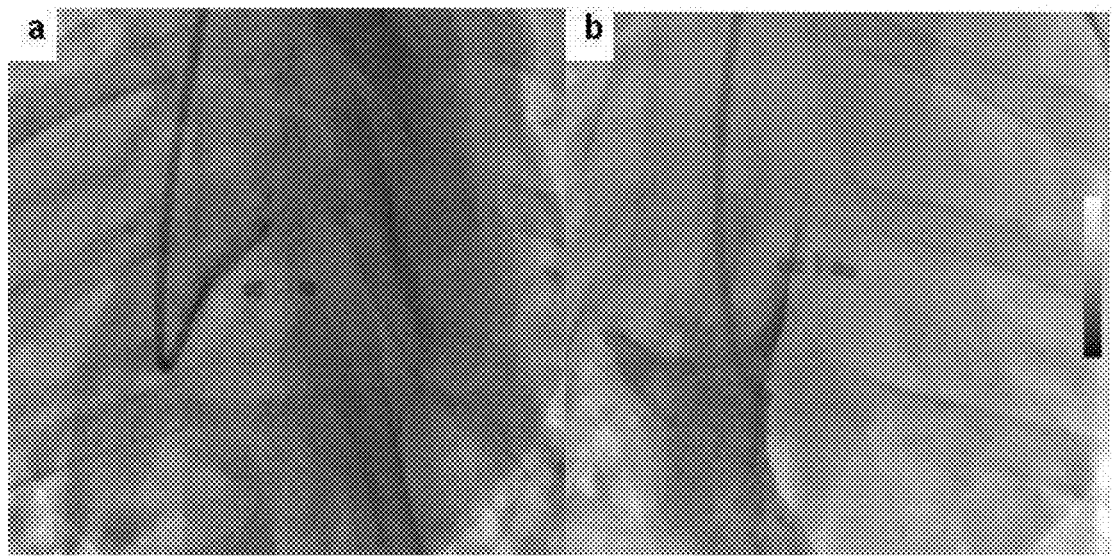
FIGS. 32a and b show fluoroscopic tests of two embodiments of occlusion devices described herein after one month: (a) occluder "CL2" and (b) occluder "CL3".

After a month of follow up, both animals were well and gained weight. Before sacrifice, the animals were anaesthetized and the device position and leakage was checked by fluoroscopy and contrast injection in the left atrium. Residual shunting was also assessed by transthoracic echocardiography (TTE) in combination with an agitated saline contrast medium injection (bubble test). FIG. 32 shows that both devices were intact and the PFO models were well sealed.

Figure 33:
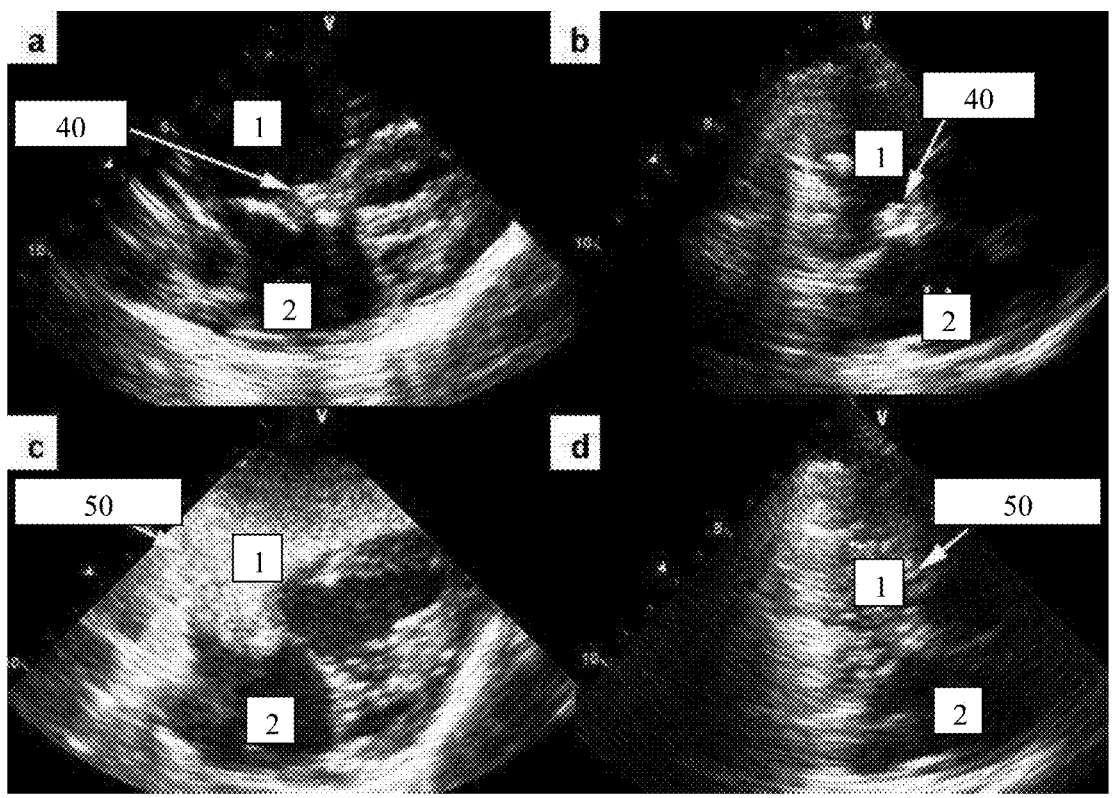
FIGS. 33a-d show transthoracic echiocardiography (TTE) images of the TTE bubble test of the occlusion devices "CL2" and "CL3": (a) and (b) TTE image after one month's implantation for "CL2" and "CL3", respectively; (c) and (d) bubbles in the right atrium (RA) for "CL2" and "CL3", respectively.

The bubble test results are shown in FIG. 33. Both "CL2" and "CL3" (40) can be seen clearly under TTE (FIG. 33a and FIG. 33b, respectively). When contrast medium was injected, dense bubbles (50) were seen in the right atrium (1), and no bubble in the left atrium (2), proving no right-to-left shunting (FIG. 33c for "CL2" and FIG. 33d for "CL3").

After a lethal injection of euthanasia solution Valabarb, complete autopsy was performed in both animals. The hearts and adjacent vessels were explanted and reviewed for the gross appearance of the device.

Device Macroscopic and Histological Examination

Macroscopic Examination Results

The gross pathology for "CL2" and "CL3" is shown by macroscopic examination of the occlusion devices implanted: (FIG. 34a) back part films (folded tail portion) of "CL2" in septum contacting RA; (FIG. 34b) front part-films (folded head portion) of "CL2" in septum contacting LA; (FIG. 34c) back part films (folded tail portion) of "CL3" in septum contacting RA and (FIG. 34d) front part films (folded head portion) of "CL3" in septum contacting LA.

Figure 34:
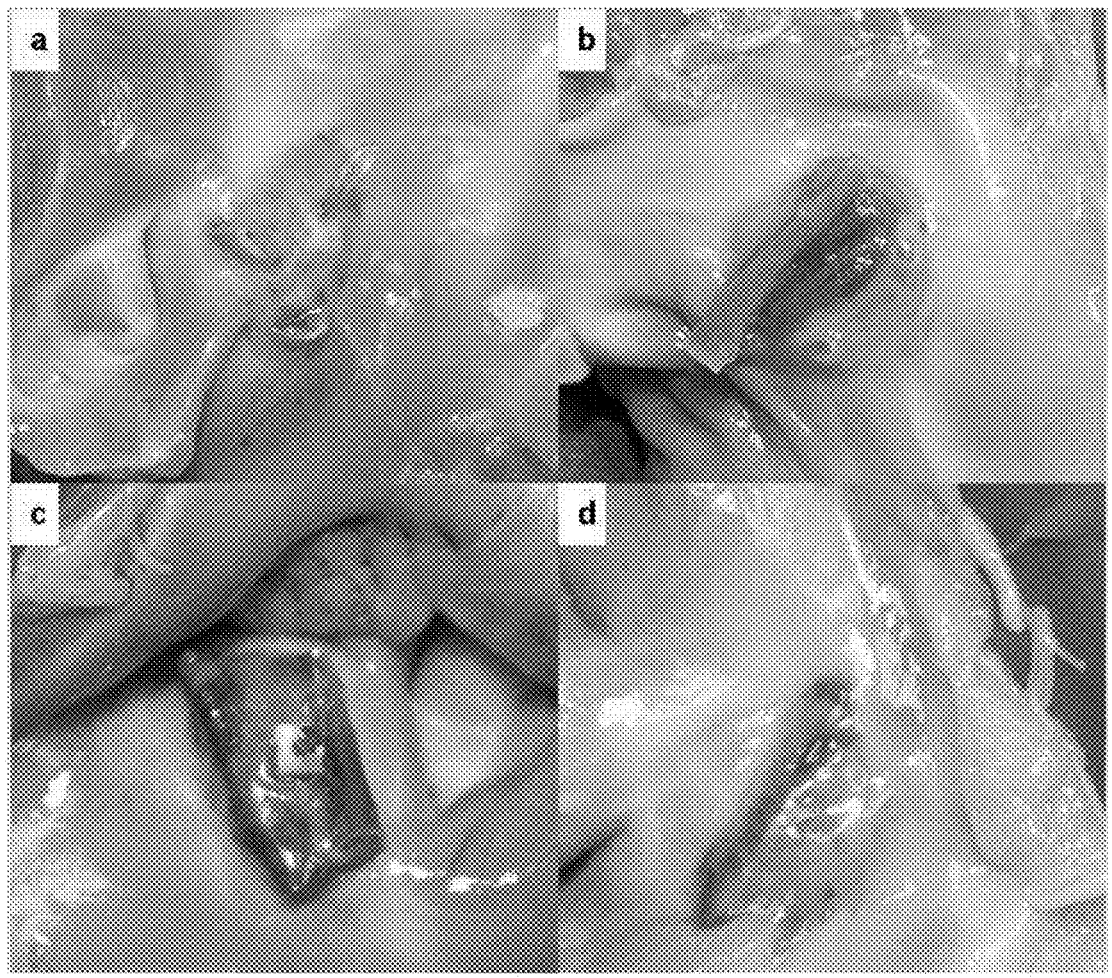
FIGS. 34a-d show a macroscopic examination of occlusion devices implanted: (a) back part films of "CL2" in septum contacting the right atrium (RA); (b) front part films of "CL2" in septum contacting the left atrium (LA); (c) back part films of "CL3" in septum contacting the right atrium (RA) and (d) front part films of "CL3" in septum contacting the left atrium (LA).

Both devices were intact and the PFO was firmly sealed. There were no fractures of the films or the loosening of the lock tubes. For each occluder the one side of folded films (either RA or LA) were completely covered (FIGS. 34a & d) and the other side were at least partially covered in "CL2" (FIG. 34b) or not covered for "CL3" (FIG. 34c). The covering is a glistening surface layer and through which films and tubes can be seen. For the uncovered films, there are some thrombi in the interlining of folded films. Thrombus can also be found in the folded films covered by the surface layer.

Histological Examination

After macroscopic examination, the septum tissues with devices were fixed in alcoholic formaldehyde for 72 hours. The histological sections were taken from the right and left atrial wall having the device and septal myocardium. Tissue samples were embedded in paraffin wax, serially sectioned, and stained with hematoxylin and eosin.

Figure 35:
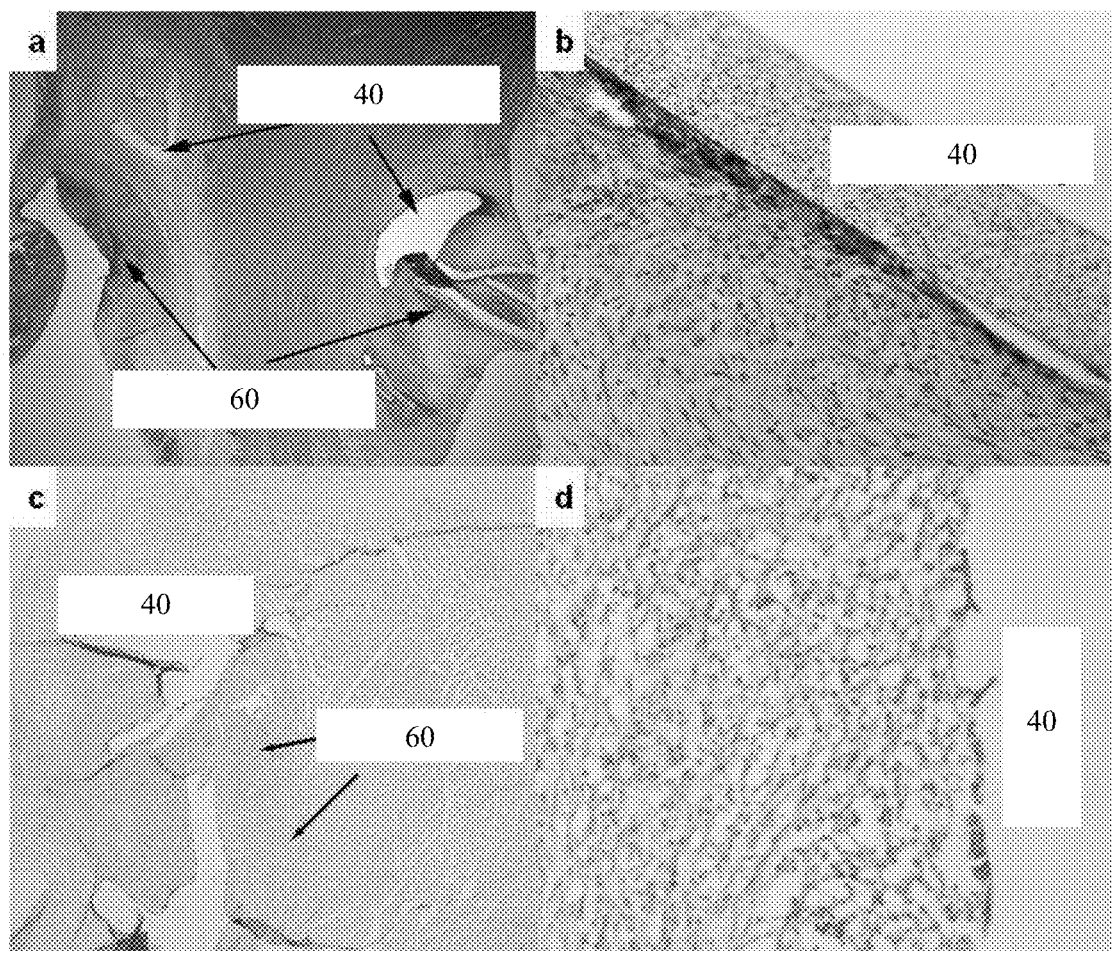
FIGS. 35a-d show the histology of the healing response to the "CL2" (a and b) and "CL3" (c and d) occluders of the present invention.

The healing response of occluders of the first aspect after one month in vivo test is shown in FIGS. 35a & b for "CL2" and in FIGS. 35c & d for "CL3". It can be seen that the occlusion devices (40) stimulated mild growth of inflammatory cells (60) and there are seldom signs of bleeding.

The occluder of the first aspect of the application shows a better healing response than conventional double umbrella-type occluders. The latter design stimulated more and denser inflammatory cells and led to some bleeding. The difference of the healing response may be explained in the closing mechanism of the devices. The design of the occlusion device according to the first aspect has soft folded films to close the ASD/PFO model and the distance between the films in the left and right atria can be adjusted according to the thickness of the septum. So the design of the occlusion device according to the first aspect can reduce to minimum the extra closing force and the stimulation exerted on the septal myocardium. The double umbrella design has a stiffer structure of spoke, which can exert more force on the septal wall and even hurt the wall. The distance between the two discs generally cannot be adjusted so it may increase the force if the septal is thicker than the stem length of the device. So the conventional double umbrella design may have more stimulation on the septal myocardium and led to more inflammatory cells. In contrast thereto, the design of the occlusion device according to the first aspect is self-adjustable to the thickness of the septum because of the specific folding mechanism of the specific occluder design. Therefore, the healing response can be improved with the occluder design of the first aspect.

Degradation Examination of the Films

Microscopic Examination

Figure 36:
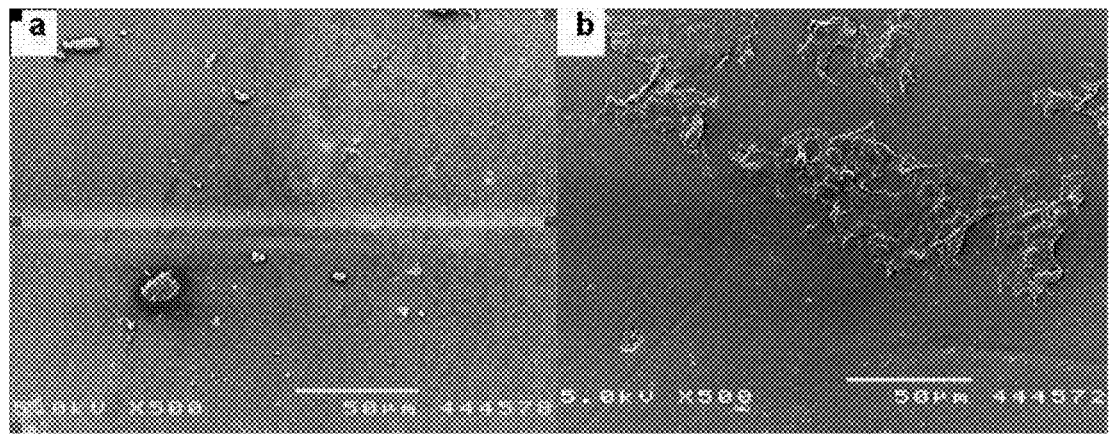
FIGS. 36a and b show photos of scanning electron microscopy (SEM) observation of the starting film (FIG. 36a) and of the film explanted after one month (FIG. 36b) of an embodiment of the occlusion device described herein.

A tiny piece of film was cut from the explanted device after sacrifice. It was cleaned with ethanol followed by deionised water in an ultrasonic bath. Scanning electron microscope (SEM) examination was conducted thereafter for the explanted film with an original starting film as control. FIG. 36 shows scattered $BaSO_4$ on the starting film surface which is relatively rough (FIG. 36a), and the film explanted is smoother and porous, considered to be a consequence of degradation and flushing away of $BaSO_4$ particles (FIG. 36b). The debris on the explanted film could be either blood clots adhered firmly to the film or some partially disintegrated polymer itself.

Example 7

As pure PLA was considered to be too stiff for this application, it was blended into the PLA-PCL copolymer at certain ratios and the Young's moduli were determined by Instron.

Figure 8:
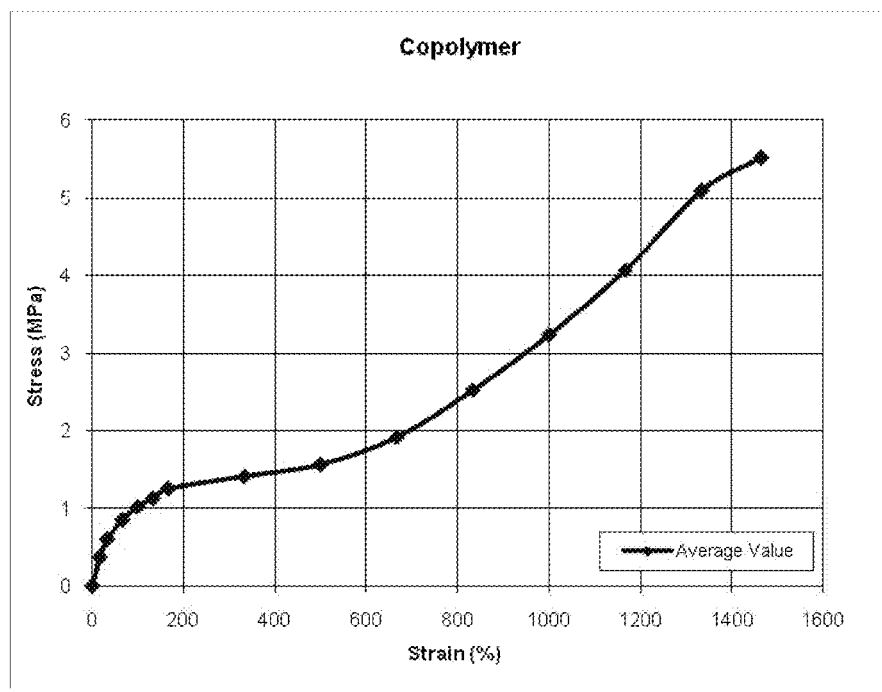
FIG. 8 shows the stress-strain curve of a copolymer of polylactic acid and polycaprolactone (PLA-PCL copolymer) 70/30.

The test was done with a load cell of 100 N at a loading rate of 55 mm/min (fastest equipment limit). The films were cut in 41×5 mm size and gripped with an effective gauge length of 5 mm (to ensure maximum stretching distance). Stress-strain curve was plotted accordingly where the Young's modulus could be obtained for each sample (FIG. 8).

Stress relaxation test was also conducted at 37° C. to study the polymer's mechanical behavior under constant strain. The sample was rapidly stretched to the required length (100% and 200% elongation) and maintained for 10 min, with the stress recorded as a function of time. Young's moduli of different material combinations were calculated and listed as shown in Table 2.

TABLE 2

Young's Moduli of polymers and their blends

| No. | Materials | Young's Modulus (MPa) |
|---|---|---|
| 1 | Pure copolymer | 0.92 |
| 2 | Pure PCL | 166.10 |
| 3 | Copolymer with 30% BaSO$_4$ | 10.55 |
| 4 | Copolymer blend with PLA (80% copolymer/20% PLA) | 5 |
| 5 | Copolymer blend with PLA (60/40) | 66.54 |
| 6 | Copolymer blend with PLGA (80% copolymer/20% PLGA) | 4.21 |
| 7 | Copolymer blend with PLGA (60/40) | 53.47 |

All the films did not break at the maximum elongation limit of the equipment (results not shown). For example, the copolymer film did not reach the breaking point even at the maximum strain rate (55 min/min) when total strain was more than 1200%, displaying an extraordinary flexibility, which is highly desired for the occluder design of the first aspect. PLA-PCL copolymer blend with PLA resulted in highest Young's modulus among all. The increment of modulus also increased tremendously with the increasing amount of PLA. Similar trend is observed among BaSO$_4$ and PLGA blended copolymer. And the excellent stretchability of more than 1200% elongation was still observed among all other blends.

Figure 9A:
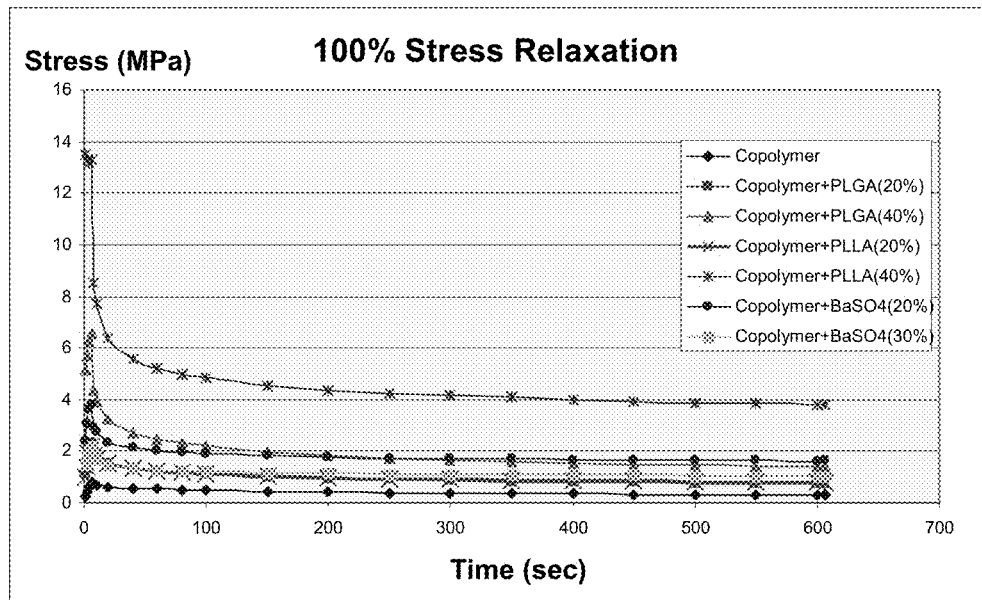
FIGS. 9a and b show the polymer stress relaxation of several copolymer candidates.
Figure 9B:
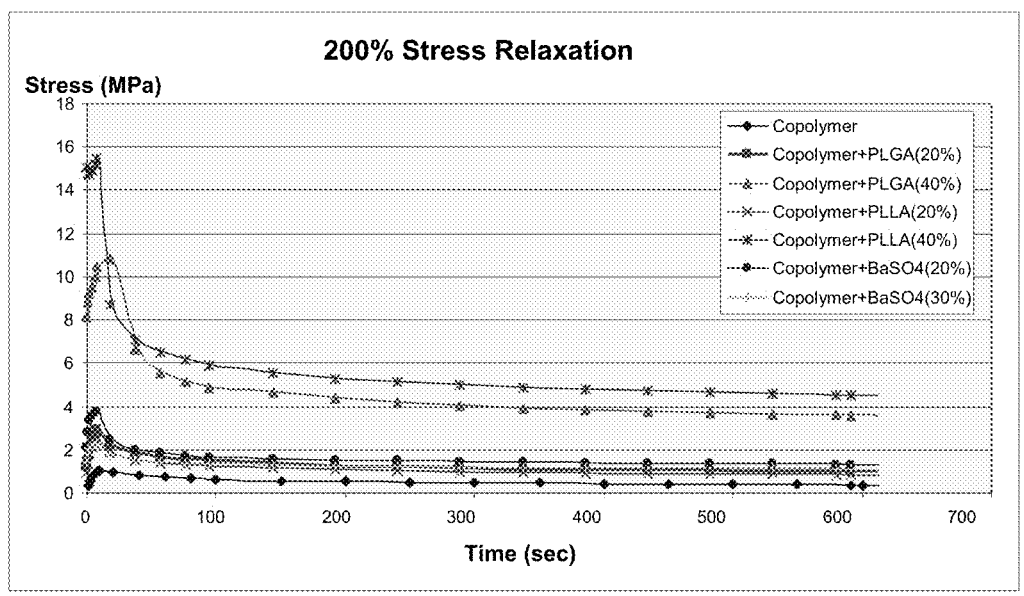

Stress relaxation results are shown in FIG. 9. The results denote that the PLA-PCL copolymer has the least amount of stress relaxation during the test period, while PLA blended copolymer shows the greatest percentage of stress relieved within the first 100 seconds of experiments. So the pure PLA-PCL copolymer resembles an elastomer mechanically among all the candidate polymers, for its low Young's modulus and long relaxation time.

CONCLUSION

The above description and exemplary part of the alternative occluder design of the first aspect of the application shows that the general concept of the present application to replace the current permanent metallic devices was successful. This has been accomplished by utilizing fully biodegradable materials to provide occlusion devices such as ASD/PFO occluders which show a good healing response. The design of occluders of the first aspect also decreases thrombogenicity, increases endothelialization, minimizes the foreign body reactions, and decreases immunological and inflammatory responses compared to conventional double umbrella occluders.

The occluder of the first aspect has moderate thrombi formation and the vast majority of them were in the device structure. For the occlusion device according to the first aspect, the thrombi can be found in the gaps of the folded films. The main reason for these thrombi is that the folded structures can influence the blood fluent dynamics which flew through them and reduce the fluent velocity. So the blood cells and plasma protein can more easily deposit on the surface of the inner structures. Anti-thrombotic agent-containing materials, especially for the film materials, can prevent the formation of thrombi.

The anchoring and the sealing functions have been successfully achieved with the occlusion device according to the first aspect utilizing a pull-fold-mechanism. The specific structural design of the scaffold and the foldable section held the devices in a satisfactory portion and keep them stable as has been shown by the above in vivo tests in animals. The TTE bubble test shows that there are no signs of leakage from the right atria (RA) to the left atria (LA), indicating an adequate sealing of the opening.

The in-vitro degradation studies and post-mortem explantation confirm that the occlusion devices of the first aspect have a good integrity and mechanical strength. Therefore, large defects can be securely sealed with these occlusion devices. Furthermore, the occlusion devices of the first aspect show minor thrombosis and foreign body reaction compared to the current occluders having a metallic structure. The folds between the films at the front side and the back side are areas where blood flow in the tissue is slowed and blood clots have been observed. However, no thrombus was seen where the copolymer was in contact with the tissue, displaying good hemocompatibility.

In addition, the delivery system of the second aspect, the kit of the third aspect and the method of the fourth aspect make it possible to achieve the above-mentioned results with the occlusion device of the first aspect. Moreover, the method of the second aspect allows not only an easy deployment of the occlusion device at the correct position but also the retrieval of the occlusion device, if this would be necessary, for example do to an accidental deployment.

The invention claimed is:

1. An occlusion device for closing an anatomical defect in tissue comprising an opening connecting a front side and a back side of a tissue, wherein the occlusion device is adapted to be included into a sheath of a catheter, and the occlusion device comprises:
   (i) a scaffold comprising:
       a head tube positioned at an anterior end of the scaffold,
       a tail tube positioned at a posterior end of the scaffold;
           wherein the head tube and the tail tube are movable along the direction towards and away from each other, and
       an engaging means connected to the head tube and being adapted to be engagable at the tail tube, and
   (ii) a foldable section comprising:
       a foldable head portion which is connected at one end to the head tube and being adapted to be disposed together with the head tube at the front side of the anatomical defect,
       a foldable tail portion which is connected to one end of the tail tube and being adapted to be disposed together with the tail tube at the back side of the anatomical defect, and
       a waist portion adapted to extend through the opening of the anatomical defect and being arranged between the foldable head portion and the foldable tail portion,
   wherein each of the foldable head portion and the foldable tail portion comprises two arms extending between the head tube and the waist portion and between the tail tube and the waist portion, respectively, wherein each arm consist of at least one sheet-like film having a folding segment at which the arm is foldable such that a part of the arm extending from one side of the folding segment folds over another part of the arm extending from another side of the folding segment,
   wherein the two arms of at least one of the foldable head portion and the foldable tail portion are configured such that, in the folded state when deployed for closing the anatomical defect, surfaces of the two arms facing the tissue extend completely around the anatomical defect, and wherein the folding segment of each arm defines a folding axis and is pre-configured with greater flexibility at the folding axis than said part and said another part of the arm so as to facilitate folding of the arm about the folding axis.

2. The occlusion device according to claim 1, wherein the two arms of the foldable head portion are arranged on each other in a manner that the engaging means is positioned between the two arms.

3. The occlusion device according to claim 1, wherein the two arms of the foldable tail portion are arranged on each other in a manner that the engaging means is positioned between the two arms.

4. The occlusion device according to claim 1, wherein the engaging means is a hollow tube.

5. The occlusion device according to claim 1, wherein the engaging means is integrally provided with the head tube and wherein the engaging means extends from the head tube in the direction of the tail tube and wherein, in an unfolded form of the occlusion device, the engaging means extends over a length in the direction of the tail tube which is half the length between the waist portion and the head tube.

6. The occlusion device according to claim 1, wherein the head tube is hollow and has a threaded interior.

7. The occlusion device according to claim 6, wherein the engaging means is engageable at the tail tube by means of a lock which is a flexible end cap having two crossed slots in its center wherein the end cap is integrally provided at the posterior end of the tail tube.

8. The occlusion device according to claim 1, wherein the foldable head portion is welded to the head tube and/or the foldable tail portion is welded to the tail tube.

9. The occlusion device according to claim 1, wherein the foldable head portion is laminated with the head tube and/or the foldable tail portion is laminated with the tail tube.

10. The occlusion device according to claim 1, wherein the foldable head portion is glued on the head tube and/or the foldable tail portion is glued on the tail tube.

11. The occlusion device according to claim 1, wherein the foldable head portion is sewed to the head tube and/or the foldable tail portion is sewed to the tail tube.

12. The occlusion device according to claim 1, wherein at least one of or all of the head tube, the end tube, the engaging means, or the foldable section are of a polymeric material.

13. The occlusion device according to claim 12, wherein the polymeric material comprises a non-biodegradable or a biodegradable polymer.

14. The occlusion device according to claim 13, wherein the non-biodegradable polymer is selected from the group consisting of polyurethane, poly(ether urethanes), poly(ester urethanes), polyvinylchloride, polyalkylenes, polyethylene terephtalate polyvinylacetate, poly ethylene-co-vinyl acetate and nylon.

15. The occlusion device according to claim 13, wherein the biodegradable polymer is selected from the group consisting of polycaprolactone (PCL), polylactic acid (PLA), polycaprolactone-polylactic acid copolymer (PCL-PLA copolymer), polyglycolide (PLGA), poly-L-lactide (PLLA), poly-D-lactide (PDLA), polygluconate (PGA), polylactide-polygluconate copolymer (PLGA), polylactic acid-polyethylene oxide copolymers, polyhydroxybutyrate, polyanhydride, polyphosphoester, poly(amino acids), polydioxanone, cellulose, collagen and chitosan.

16. The occlusion device according to claim 12, wherein the polymeric material of the foldable section has a modulus range of about 104 to about 107 Pa at 37° C.

17. The occlusion device according to claim 1, wherein the entire occlusion device is made of a polymeric material.

18. The occlusion device according to claim 1, wherein the tail tube has a threaded exterior surface.

19. The occlusion device according to claim 1, wherein one or more elements selected from the head tube, the tail tube, the engaging member and the foldable section comprise a therapeutically active agent.

20. The occlusion device according to claim 19, wherein the therapeutically active agent is selected from the group consisting of a drug, an antibiotic, an anti-inflammatory agent, an anti-clotting factor, a hormone, a nucleic acid, a peptide, a cellular factor, a growth factor, a ligand for a cell surface receptor, an anti-proliferation agent, an anti-thrombotic agent, an antimicrobial agent, an anti-viral agent, a chemotherapeutic agent, and an anti-hyertensive agent.

21. The occlusion device according to claim 1, wherein one or more elements selected from the group of the head tube, the tail tube, the engaging means and the foldable section comprise a radiopacifier deposited at its surface and/or blended in the material the elements comprise.

22. A delivering system for an occlusion device of claim 1 adapted to be included into a sheath of a catheter, comprising:
    at least one first delivering means adapted to push the occlusion device through a sheath and to guide the head portion of the foldable section in a position at the front side of a tissue defect, and
    at least one second delivering means adapted to move the tail tube into the direction of the head tube to allow the tail tube to be moved against the back side of the tissue.

23. The delivering system according to claim 22, wherein the at least one first delivering means is a delivering rod extending through the tail tube towards the head tube of the occlusion device and being removably connected to the head tube.

24. The delivering system according to claim 23, wherein the delivering rod is made of a shape memory metal such as a Ni—Ti alloy like nitinol, Cu—Zn alloy, Fe—Ni—Al alloy or shape memory polymer.

25. The delivering system according to claim 23, wherein the delivering rod has a threaded exterior surface at the end of the delivering rod facing the tail tube wherein the end of the delivering rod is threaded to engage a threaded interior surface of the head tube.

26. The delivering system according to claim 22, wherein the at least one second delivering means is a cylindrical hollow deployment tube.

27. The delivering system according to claim 26, wherein the deployment tube is made of a polymeric material.

28. The delivering system according to claim 26, wherein the deployment tube has a thread at the inner surface of its tip which is adapted to be engaged into the thread of the tail tube.

29. The delivering system according to claim 22, further comprising a sheath adapted to cover at least the occlusion device and the first and second delivering means.

30. A kit comprising an occlusion device of claim 1 and a delivering system for the occlusion device, the delivering system comprising:
    at least one first delivering means adapted to push the occlusion device through the sheath and to guide the head portion of the foldable section in a position at the front side of a tissue defect, and
    at least one second delivering means adapted to move the tail tube into the direction of the head tube to allow the tail tube to be moved against the back side of the tissue.

31. The kit according to claim 30 provided in a sterilized package.

32. A method of closing an anatomical defect in a tissue comprising an opening connecting a front side and a back side of a tissue, comprising the steps of:
- providing a sheath into which an occlusion device according to claim 1 and a delivering system have been inserted, the delivering system comprising:
  - at least one first delivering means adapted to push the occlusion device through the sheath and to guide the head portion of the foldable section in a position at the front side of a tissue defect, and
  - at least one second delivering means adapted to move the tail tube into the direction of the head tube to allow the tail tube to be moved against the back side of the tissue
- pushing the occlusion device through the sheath to the site of the anatomical defect by using a first delivering means of the delivering system,
- pushing a head tube of a scaffold and a foldable head portion of a foldable section of the occlusion device out of the sheath through the defect to the front side of the tissue,
- folding the foldable head portion by moving the head tube of the occlusion device in the direction of the front side of the tissue by means of the first delivering means to close the defect from the front side,
- withdrawing the sheath to release the waist portion and the tail portion of the foldable section of the occlusion device in the opening and at the back side of the tissue, respectively, and
- moving the tail tube of the occlusion device against the back side of the tissue by means of the second delivering means of the delivering system to fold the foldable tail portion of the foldable section of the occlusion device and locking the occlusion device at the anatomical defect from the back side of the tissue.

33. The method according to claim 32, wherein the sheath goes through the opening while the foldable head portion and the head tube are pushed out of the sheath.

34. The method according to claim 32, wherein the sheath is at the front side of the defect while the foldable head portion and the head tube are pushed out of the sheath.

35. The method according to claim 32, further comprising the step of retrieving the delivering system out of the sheath of the catheter.

36. The method according to claim 35, wherein the step of retrieving the delivering system comprises the steps of withdrawing the first delivering means removably connected to the head tube of the occlusion device and removing the second delivering means by withdrawing it out of the catheter.

37. The method according to claim 32, further comprising a re-anchoring step, wherein the sheath is held in position, the first delivering means is moved forward to unfold the folded head portion and then performing re-anchoring by folding the foldable head portion of the foldable section of the occlusion device.

38. The method according to claim 32, further comprising a correction step of the sealing procedure, wherein the first delivering means is held in position and the second delivering means is moved to unfold the entire occlusion device and to move back the foldable tail portion of the occlusion device into the sheath again and repeating the folding procedure.

39. The method according to claim 32, wherein the anatomical defect in a tissue is a septal defect or shunt in the heart or the vascular system.

40. The method according to claim 39, wherein the septal defect is an atrial septal defect, ventricular septal defect, patent ductus arteriosus, or patent foramen ovale.

* * * * *